United States Patent
Wong et al.

(10) Patent No.: US 8,939,766 B2
(45) Date of Patent: Jan. 27, 2015

(54) DENTAL TOOLS FOR PHOTO-CURING OF DENTAL FILLINGS

(71) Applicants: Alan Wong, Federal Heights, CO (US); Howard Steven Rosen, Denver, CO (US)

(72) Inventors: Alan Wong, Federal Heights, CO (US); Howard Steven Rosen, Denver, CO (US)

(*) Notice: Subject to any disclaimer, the term of this patent is extended or adjusted under 35 U.S.C. 154(b) by 7 days.

(21) Appl. No.: 13/751,033

(22) Filed: Jan. 25, 2013

(65) Prior Publication Data
US 2013/0137058 A1  May 30, 2013

Related U.S. Application Data

(63) Continuation-in-part of application No. 13/293,948, filed on Nov. 10, 2011, now abandoned, which is a continuation-in-part of application No. 13/086,057, filed on Apr. 13, 2011, now abandoned, which is a continuation-in-part of application No. 12/763,159, filed on Apr. 19, 2010, now abandoned.

(51) Int. Cl.
*A61C 5/04* (2006.01)
*A61C 13/15* (2006.01)
*A61C 3/08* (2006.01)
*G02B 6/36* (2006.01)

(52) U.S. Cl.
CPC .............. *A61C 5/045* (2013.01); *A61C 19/004* (2013.01); *A61C 3/08* (2013.01); *G02B 6/3624* (2013.01)
USPC ........................................... 433/226; 433/29

(58) Field of Classification Search
USPC .................... 433/29, 141, 164, 215, 229, 226
See application file for complete search history.

(56) References Cited

U.S. PATENT DOCUMENTS

| | | | | |
|---|---|---|---|---|
| 2,606,366 A * | 8/1952 | Stevens | .......................... | 433/166 |
| 3,646,677 A * | 3/1972 | Saupe et al. | .................. | 433/127 |
| 3,751,176 A * | 8/1973 | Von Hollen | .................... | 408/144 |
| 4,050,895 A * | 9/1977 | Hardy et al. | ................... | 436/527 |
| 4,109,384 A * | 8/1978 | Dorian | .......................... | 433/147 |
| 4,233,493 A * | 11/1980 | Nath | ............................... | 606/16 |
| 4,483,678 A * | 11/1984 | Nishio et al. | ................ | 433/201.1 |
| 4,736,743 A * | 4/1988 | Daikuzono | ...................... | 606/28 |
| 5,098,292 A * | 3/1992 | Lazarof | .......................... | 433/141 |
| 5,139,495 A * | 8/1992 | Daikuzono | ...................... | 606/17 |
| 5,359,911 A * | 11/1994 | Kruesi | .............................. | 81/436 |
| 5,388,987 A * | 2/1995 | Badoz et al. | .................... | 433/29 |
| 5,554,029 A * | 9/1996 | Kowalyk et al. | .............. | 433/215 |
| 5,616,141 A * | 4/1997 | Cipolla | ........................... | 606/15 |
| 5,782,638 A * | 7/1998 | Warren et al. | ................. | 433/206 |
| 5,797,740 A * | 8/1998 | Lundvik | ......................... | 433/29 |
| 5,971,755 A * | 10/1999 | Liebermann et al. | ........... | 433/29 |
| 6,290,502 B1 * | 9/2001 | Hugo | ............................. | 433/215 |
| 7,074,040 B2 * | 7/2006 | Kanca | ............................ | 433/29 |
| 2011/0256497 A1* | 10/2011 | Wong et al. | ..................... | 433/29 |
| 2012/0196427 A1* | 8/2012 | Nakano et al. | ................ | 438/463 |

* cited by examiner

*Primary Examiner* — Cris L Rodriguez
*Assistant Examiner* — Hao D Mai
(74) *Attorney, Agent, or Firm* — Roger A. Jackson

(57) ABSTRACT

A dental tool for use in photo-cured filling processes. The dental tool includes a tool tip formed from a material that allows the transmission of ultraviolet and visible light wavelengths through the tool tip without significant distortion or reflection. The material is also relatively high strength so not to shatter or break during use. The fill material will also not easily adhere to the tool. The material of a preferred embodiment is sapphire. The tool is able to continue to compact and shape the fill material while the composite polymer fill material is undergoing photo-curing. The light beam used for photo-curing is able to safely pass through the tool without the risk of damage to the surrounding tissue from reflection or distortion of the light beam.

8 Claims, 47 Drawing Sheets

DENTAL TOOLS FOR PHOTO-CURING OF DENTAL FILLINGS

RELATED APPLICATIONS

This is a continuation in part (CIP) patent application of U.S. patent application Ser. No. 13/293,948 filed on Nov. 10, 2011 by Alan Wong et al. of Federal Heights, Colo., U.S., that is a continuation in part (CIP) patent application of U.S. patent application Ser. No. 13/086,057 filed on Apr. 13, 2011 by Alan Wong et al. of Federal Heights, Colo., U.S. that is a continuation in part (CIP) patent application of U.S. patent application Ser. No. 12/763,159 filed on Apr. 19, 2010 by Alan Wong of Federal Heights, Colo., U.S.

TECHNICAL FIELD

The present invention generally relates to filling cavities in teeth for the dental arts. More particularly, the present invention is a dental tool having a light transmittable tip portion to accommodate the transmission of light used for photo curing a composite filling while the dental tool tip portion concurrently forms the composite into a desired position simultaneously with the curing light transmitted therethrough the dental tool tip portion to allow the composite curing to be a more controlled process for the desired forming of the composite in relation to the tooth.

BACKGROUND OF INVENTION

Dental fillings have been commonly used for centuries to fill cavities in teeth. Traditionally, amalgam fillings were commonly used as dental fillings for decades. Amalgam fillings include two or more metals of which one is mercury usually in the range of 40-50 percent. While these fillings have been in common use for over 150 years, there are a number of concerns with the use of mercury. Mercury, while generally considered safe for use in dental amalgams, does raise safety concerns both in use and in disposal later. Also, amalgam fillings permanently weaken the brittle crystalline structure of the tooth as the void left by cavity preparation is a permanent removal of integral material strength for the tooth, wherein the amalgam filling does not replace the void with a structurally integral element as the amalgam does not bond with the tooth as it must be retained with features to hold it in the tooth, further amalgam tends to discolor over time as well as being undesirably noticeable or visible, being typically bright silver in color that is in stark contrast to the near white tooth enamel color.

Composite fillings have become more popular replacing amalgam fillings as being much more structurally sound when disposed within the prepared cavity of the tooth, as the composite bonds as against the prepared cavity surfaces, thus helping to restore the structural integrity of the tooth that is lost to the prepared cavity to nearly that of a non cavity tooth. Composite fillings are typically a mixture of acrylic resins and glass-like powders. These fillings can be self hardening, that can require the mixing of substances-increasing the chances for undesirable air pocket porosity in the filling mixture, thus the use of a composite that doesn't require mixing is preferred, however, requiring to be cured with the use of ultraviolet light rays.

Composite fillings can be matched closely with the color of existing teeth, thus desirably rendering them practically invisible in relation to the tooth they are disposed in; further composite fillings are relatively durable and moderate in price. However, negatives are that the placement of the composite fillings into the cavities of the tooth can be difficult in order to eliminate any air pocket porosity or other voids where bacteria might be able to grow, or causing increased tooth hot and cold sensitivity, and further causing weakness in the combined tooth/composite structure.

Other types of tooth fillings include resin-reinforced glass ionomer fillings, porcelain fillings, ceramics, cast gold, and others. These fillings have a variety of problems associated with them and typically are not as commonly used as composites which are becoming the de-facto preferred standard tooth filling.

The process of filling a cavity with a composite filling requires initial preparation of the cavity by removing any decay, then cleaning and completely drying the cavity. Then thin layers of the composite filler material, being approximately one millimeter in thickness, are applied repeatedly with photo curing of each layer prior to the application of the next layer. Once the cavity has been filled with the layers of composite filling polymer, the final layer is shaped to the desired result in substantially conforming to the tooth outer surface, any excess composite material is trimmed and the final result is polished to achieve a smooth transition from the composite filling surface to the native tooth enamel surface.

The layers of composite polymer are each hardened within the prepared tooth cavity through photo-polymerization via the application of external energy, i.e. typically in the form of light. This process entails the use of a focused beam of light, usually ultraviolet or visible light. Typically, an ultraviolet light beam is focused on the applied layer of composite polymer which activates the resin causing the layer to harden. The composite polymer will shrink some during the photo-polymerization process, being typically about 2-6% which is undesirable in increasing the risk of air pocket porosity in the composite and weakened bonding as between the composite and the prepared tooth cavity. Since voids in the cavity can lead to bacteria growth, or causing increased tooth hot and cold sensitivity, and further causing weakness in the combined tooth/composite structure, thus it is critical to eliminate any such voids.

This results in the need for multiple thin layers of the composite polymer. Also, the polymer must be manipulated into the prepared cavity which is typically difficult to reach and relatively small in volume to ensure that no voids are created in the filling, all of which requires about 50% more time usually in completing the tooth filling with composites as compared to the prior art amalgam fillings that typically require less time to complete the tooth filling. Skilled dentists can ensure that the composite polymer material is properly applied by the feel of the dental tools in applying and manipulating the polymer material in the cavity as well as by visual inspection of the site.

The composite filling material curing light optimally should be positioned as close as possible to the composite material for maximum effectiveness, being a difficult task as the composite material is usually in a hard to reach location. Further, most conventional dental tools are formed from stainless steel or plastic materials and these materials reflect or otherwise interfere with the ultraviolet or visible light rays used to cure the composite filling material that not only causes inappropriate curing, but can also create damage to surrounding tissue in the mouth. Thus, conventional dental tools are typically not able to be used during the actual photo-curing process, resulting in the conventional dental tool and the curing light having to be used independently of one another, resulting in composite forming and curing having to be done as two separate operations, wherein if the dental tool could simultaneously form the composite to the prepared cavity while curing the chance of voids in the composite would be reduced along with less time being required via performing the two operations of forming and curing at the same time.

Another problem that often occurs with the conventional dental tool stainless steel and plastic materials is the adhesion of composite fill material to those materials while trying to form the composite filling material into layers within the prepared cavity. This creates additional problems in attempting to compact and shape the fill material not only during the curing process but even before the cure process. The adhesion of the composite fill material to the tool causes ripping of the material from the cavity and the creation of voids in the fill, often resulting in a greater chance of undesirable air pocket porosity and added time to complete the composite filling of the tooth. Furthermore, an added wetting agent is used to reduce the composite from tending to stick to the dental tool, however, this being undesirable due to the wetting agent interfering with the desired dry prepared cavity for composite bonding and again the added time to deal with the wetting agent as being an added step in the composite tooth filling process.

In the prior art in U.S. Pat. No. 4,666,405 to Ericson disclosed is a method and apparatus for polymerizing light-hardening dental fillings of class II type material, wherein a light transmitting frustroconical tip is screwed or pressed onto a fiber optic hand piece. Wherein the frustroconical tip in Ericson pushes the dental filling down into the dental filling as against a matrix band, see FIG. 3, and as the frustroconical tip is formed from an inverted cone shape with the narrow tip facing downward, the tip can be more easily removed from the dental filling and the matrix band. Again referring to FIG. 3 in Ericson, in can be seen that only downward pressure can be applied from the hand piece toward the tip, wherein Ericson does not teach forceful omnidirectional manipulation of the dental filling with the tip, as Ericson only teaches a single downward force movement of the tip into the dental filling.

Continuing in the prior art in U.S. Pat. No. 6,940,659 to McLean et al., disclosed is a cone shaped lens having increased forward light intensity and associated kits, wherein the lens forms a protective cover for the dental light curing device, with the primary goal of the lens is to minimize refraction of the light to help the light to have a higher intensity to cure the light curable dental filling. The McLean lens is of necessity thin in its cross sectional wall to aid in minimizing the light refraction and has a snap fit to the light device as shown in FIG. 3, further due to the broad or shallow cone shape, McLean does not come into contact with the dental filling composite material, as FIG. 4 shows the lens is at best only proximate to the dental filling composite material and also due to the thin wall thickness of the lens and broad based cone configuration, the lens is not taught to forceably manipulate the dental filling composite or even come into contact with it.

Further, in the prior art in United States patent application publication number 2008/0014546 to Sundstrom et al., disclosed is a tool for making a dental filing using a light transmitting tip configuration similar to McLean et al., wherein the tip is flexible having a loose fit over a light guide, see FIGS. 3, 10a, and 10b, thus allowing the easy changing of different tips on the light guide. Thus also as in McLean et al., in referring to FIG. 1 of Sundstrom et al., only downward force can be applied to the dental filling as against a matrix band due to the loose fit of the tool to the light guide and the flexible nature of the tool would teach against the forceable omnidirectional manipulation the dental filling via the tool.

SUMMARY OF INVENTION

The present invention provides dental tools that can be safely used to manipulate and compact composite polymer fillings not only prior to the curing process but during the curing process. The dental tool does not distort or reflect the transmission of ultraviolet or visible light used to cure the polymers in the cavity. The ability on the dental tool to be used during the photo-curing process enables the composite polymer to be compacted and shaped as the polymer shrinks during curing-being about in the range of 2-6%, thus minimizing the occurrence of voids in the filling and weakened bonding between the composite and the prepared tooth cavity. This increases the efficiency of the process, reducing the time the patient must endure the filling process and minimizing the possibility of bacteria growth and infections.

The dental tool of a preferred embodiment of the present invention uses a tool tip that has at least a portion formed from a material that allows the transmission of ultraviolet wavelengths (200-400 nm) and visible wavelengths (380-760 nm) through the portion of the tool tip without distortion or reflection of the wavelengths. This reduces the risk of damage to the tooth or surrounding tissue. The material also has a relatively high tensile strength so not to break or shatter during use. The entire tool tip may be formed from this material, or only the working portion of the tool tip may be formed from this material.

In one preferred embodiment, the tool tip of the dental tool is formed from sapphire. Sapphire has a high degree of transmission of wavelengths in the 150-800 nm range. Sapphire also has a relatively high tensile strength (275-400 MPa) compared to most optical materials, so that it is durable and resistant to shattering or breaking during use. While sapphire ($Al_2O_3$) is found naturally, it is also able to be produced artificially at a reasonable cost. It may also be grown, formed or machined into different shapes as well. The entire tool tip may be formed from sapphire or only the working area of the tool tip may be formed from sapphire.

The dental tool of a preferred embodiment provides a plurality of tool tips that may be attached to a gripping member. This enables the tool tips to be selected for particular uses while other tool tips have other uses. It also enables the tool to be used with opaque tool tips when a photo-curing process is not being used. The tool may also include tool tips on opposing ends of the tool so that the tool can simply be reversed when another tool tip is needed.

The dental tool of a preferred embodiment is used during a photo-curing filling process. For example, the cavity of a tooth is prepared for filling by removing decay and shaping the cavity. Then a thin layer of composite polymer fill material is applied to the cavity by the dental tool (or another dental tool). A light beam of ultraviolet (or visible light) wavelength is then directed to the fill material in the cavity. The dental tool is then used to further compact and shape the fill material as the fill material shrinks during the photo-curing process. The light beam is able to safely pass through the tool tip with only minimal distortion or reflection. Previously, the fill material would shrink and create voids in the fill material as it was unsafe to use existing tools. Then the dentist would attempt to fill the voids with additional fill material and to further shape the fill material. The tool of the present invention enables the fill material to be compacted and shaped while it is curing and shrinking. This provides a much more efficient process and one that minimizes the occurrence of voids in the fill material and provides better bonding between the composite and the prepared tooth cavity.

The tool of the preferred embodiment increases the efficiency of the cavity filling process. The ability to compact, manipulate and shape the fill material before and during the photo-curing process to eliminate voids from occurring while the material shrinks during the curing process greatly speeds up the fill process. Previous tools could not be used during the curing process so that voids would occur when the fill material shrank. The fill material would then have to be applied to the voids and cured, which could result in more voids occurring. This increases the time necessary to fill the cavity, decreasing the productivity of the dentist and increasing the discomfort to the patient. The tool of the present invention decreases the amount of time necessary to fill the cavity by allowing the fill material to be compacted and shaped during the photo-curing process. The ability of the tool to shed the fill material also increases the efficiency since the fill material will remain in place in the cavity.

These and other objects of the present invention will become more readily appreciated and understood from a consideration of the following detailed description of the exemplary embodiment(s) of the present invention when taken together with the accompanying drawings, in which;

REFERENCE NUMBERS IN DRAWINGS

Figure 1:
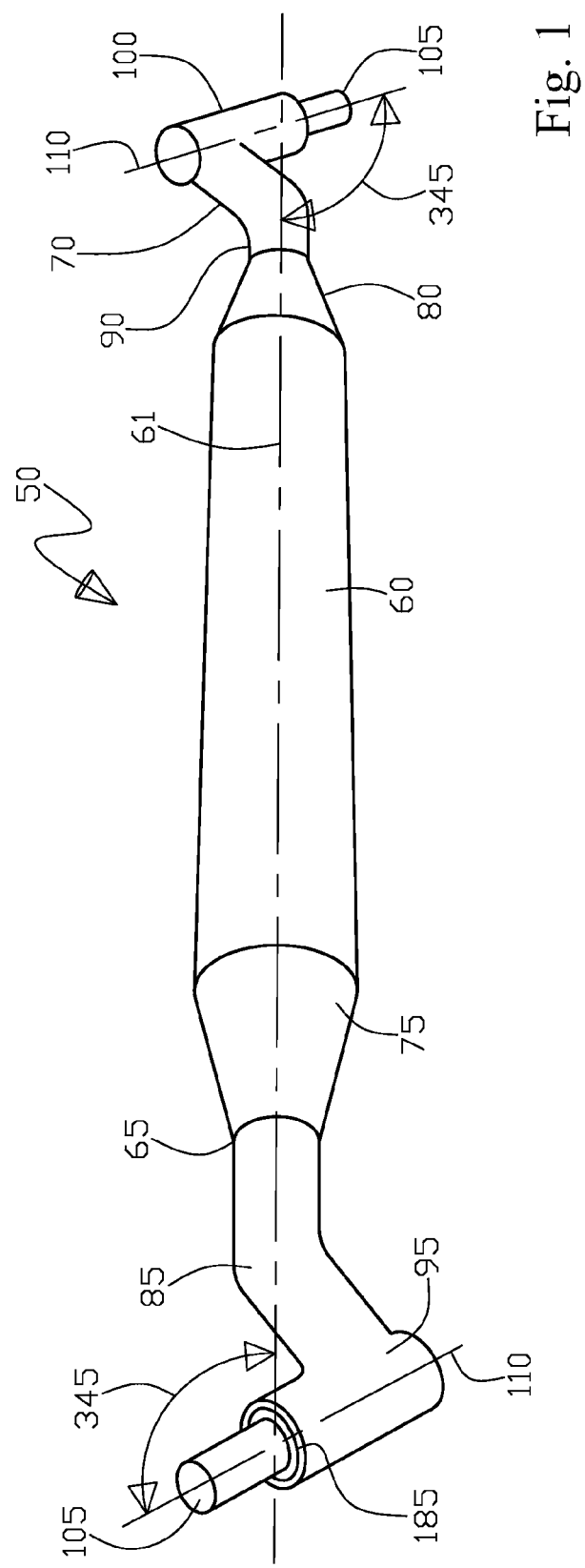
FIG. 1 is a perspective view of the dental tool of a preferred embodiment of the present invention.

50 Dental tool assembly
55 Dental tool assembly with integral photo curing light apparatus
56 Proximal portion of dental tool assembly 55
60 Gripping member of the dental tool assembly 50 or 55
61 Longitudinal axis of the gripping member 60
65 First tool end portion of the dental tool assembly 50 or 55
70 Opposing second tool portion end of the dental tool assembly 50 or 55
75 Extended first end
80 Opposing extended second end
85 First portion
90 Opposing second portion
95 First extension end portion
100 Second extension end portion
101 Receiving void cavity or bore for the cantilever beam extension portion 105 in the first and/or second extension end portions 95 or 100 wherein the cantilever beam extension 105 has a portion disposed within the receiving void 101 completely leaving an exposed cantilever beam extension portion 107
102 Depth of receiving bore 101
103 Diameter of receiving bore 101
105 Rigid tool tip extension portion in the form of a rigid cantilever beam extension
106 Diameter of the exposed 107 tip portion 105
107 Exposed cantilever beam extension portion of the tip extension portion 105
110 Lengthwise axis of the tip portion 105
115 Hammer head type tip for the tip portion 105
120 Anvil type tip for the tip portion 105
125 Parallelepiped type tip for the tip portion 105
130 Cylindrical type tip for the tip portion 105
135 Cylindrical type tool tip with a semi spherical tip for the tip portion 105
140 Cylindrical type tool tip with a wedge or chisel end portion tip for the tip portion 105
145 Cylindrical type tool tip with a radius point conical end portion tip for the tip portion 105
150 Cylindrical type tool tip with a skewed wedge end portion tip for the tip portion 105
155 Cylindrical type tool tip with an arcuate segment end portion tip for the tip portion 105
160 Cylindrical type tool tip with a full spherical end portion tip for the tip portion 105
165 Cylindrical type tool tip with a teardrop end portion tip for the tip portion 105
170 Cylindrical type tool tip with a rectangular parallelepiped end portion tip for the tip portion 105
175 Cylindrical type tool tip with a widened rectangular parallelepiped end portion tip for the tip portion 105
180 Dual cylindrical type portion tip for the tip portion 105
185 Receiving void in the form of a collet chuck
190 Inner sleeve of the collet chuck 185
195 Outer sleeve of the collet chuck 185
200 Detent of the collet chuck 185

205 Slip fit or radial clearance of tip 105 to receiving bore 101 on the second portions 95 or 100
210 Adhesive forming an interface
215 Surface treatment
250 Photo curing light apparatus
251 Removable engagement of the dental tool assembly 55 and the photo-curing light 250
260 Light transmission pathway or communication from the light apparatus 250
300 Patient
305 Mouth of patient
310 Prepared tooth with cavity of patient 300
315 Composite filler material
316 Porosity or voids in the composite material 315
317 Layers of the composite filler material 315 in the prepared cavity 310
318 Shrinkage of the composite filler material 315 during curing in going from a pliable non-hardened state to a cured hardened state
320 Dentist or dental practitioner
325 Cylindrical type tool tip with a right angled planar extension in the form of a hoe shape
330 Cylindrical type tool tip with a right angled planar extension that is tapered in the form of a hoe shape
335 Cylindrical type tool tip with an extended conical end portion
340 Cylindrical type tool tip with a light diffusing outer surface
345 Obtuse angle as between the longitudinal axis 61 and the lengthwise axis 110 positioned adjacent to the cantilever beam extension 105
350 Surface undulation width on the exposed cantilever beam extension
355 Surface undulation length on the exposed cantilever beam extension
360 Surface undulation diameter on the exposed cantilever beam extension
365 Omnidirectional forces or converted into a pressure on the cantilever beam extension 105 in relation to the lengthwise axis 110
370 Force or converted into a pressure on the cantilever beam extension 105 in relation to the lengthwise axis 110
375 Atmosphere or environment
380 Free area of composite filler material 315 exposed to atmosphere 375, wherein composite filler material 315 is not in contact with prepared tooth 310 or rigid tool tip extension 105
385 Uncontrolled flowing of composite filler material 315 in free area 380
390 Conventional prior art dental tool tip that is not transparent and typically constructed of stainless steel
395 Prior art tool tip 390 interface with composite filler material 315
396 Transparent tool tip 105 interface with composite filler material 315
400 Pullback force direction for tool tip 395
405 Pullback force effect on uncured composite filler material 315 from pullback force 400 due to stickiness as tool tip interface 395 causing an undesirable void 316, wherein typically a non-stick wetting agent is used at interface 395 to prevent the pullback force effect 405, however, the non-stick wetting agent can contaminate and weaken the desired prepared tooth 310 and composite filler material 315 bonding
410 Initial layer of a selected conical shaped configuration of composite filler material 315 layer as created by tool tip 335
411 Second layer of a selected conical shaped configuration of composite filler material 315 layer as created by tool tip 335
412 Third layer of a selected conical shaped configuration of composite filler material 315 layer as created by tool tip 335
415 Initial layer of a selected wedge shaped configuration of composite filler material 315 layer as created by tool tip 150
416 Second layer of a selected wedge shaped configuration of composite filler material 315 layer as created by tool tip 150
417 Third layer of a selected wedge shaped configuration of composite filler material 315 layer as created by tool tip 150
418 Fourth layer of a selected wedge shaped configuration of composite filler material 315 layer as created by tool tip 150
419 Fifth layer of a selected wedge shaped configuration of composite filler material 315 layer as created by tool tip 150
420 Non-hardened pliable sate of the composite filler material 315
425 Hardened cured state of the composite filler material 315

DETAILED DESCRIPTION

Figure 2:
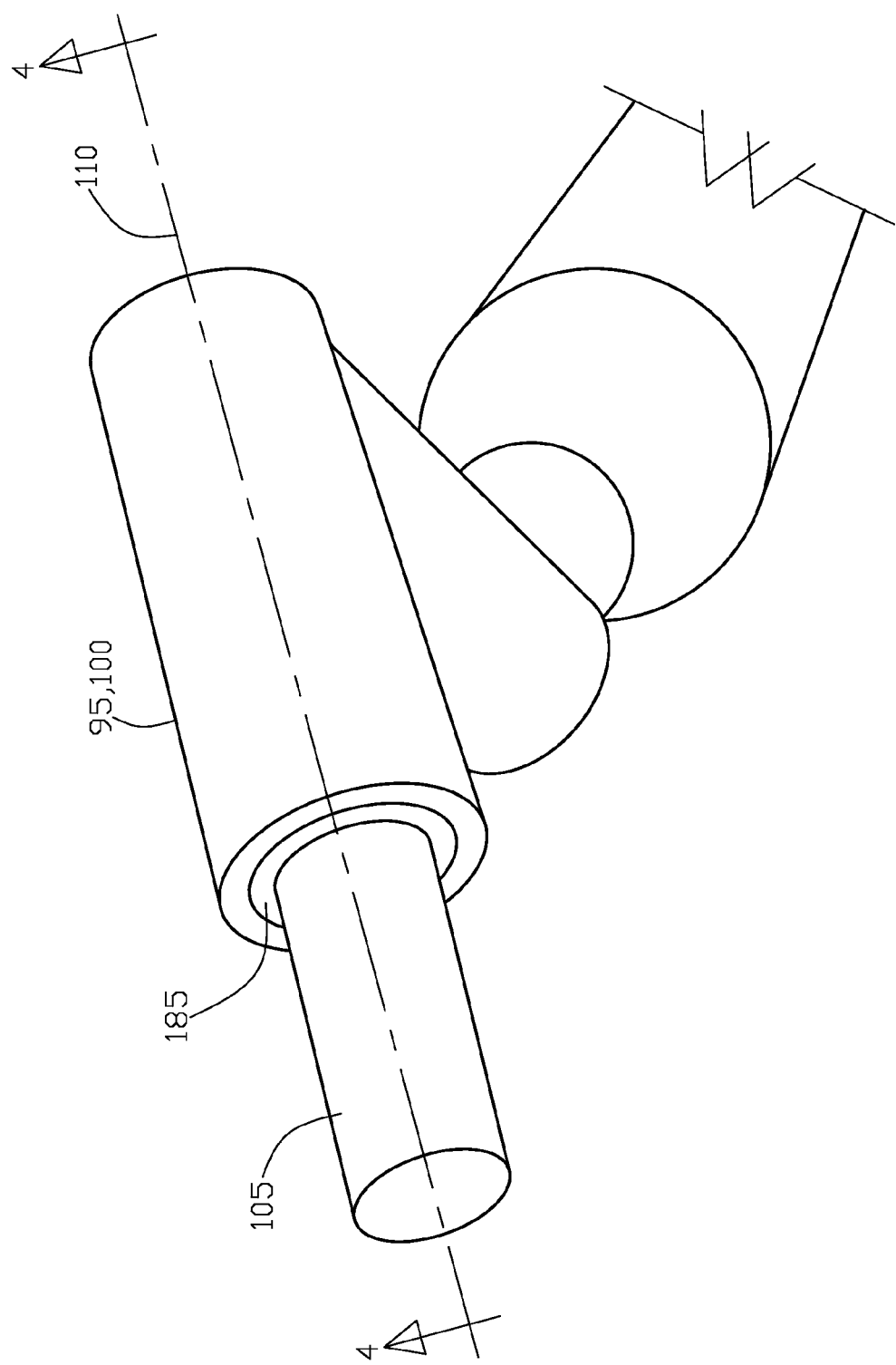
FIG. 2 is an expanded detail view of the tool tip of the tool of FIG. 1.
Figure 3:
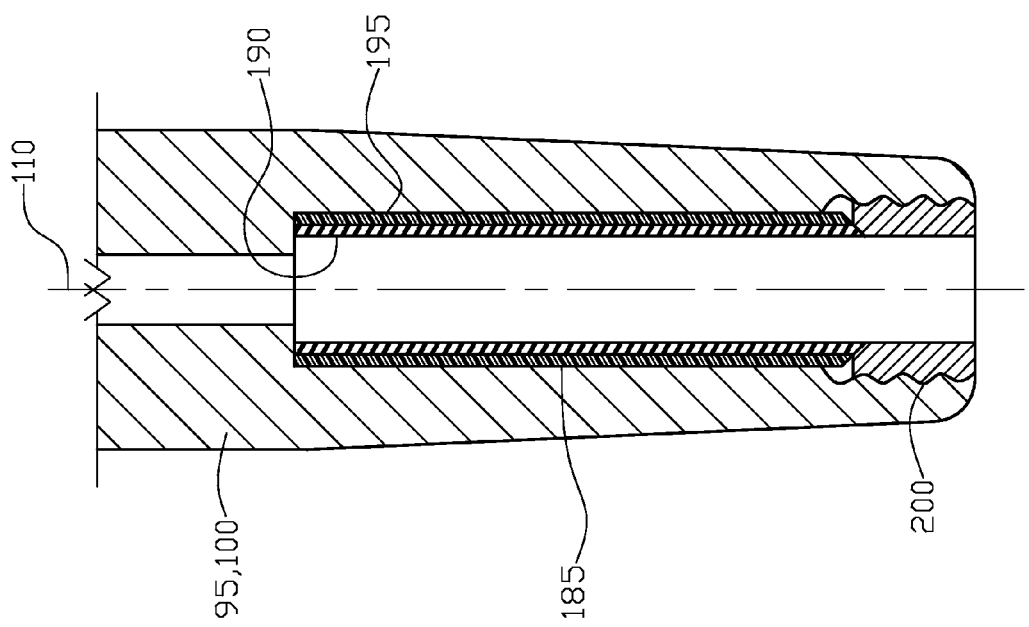
FIG. 3 is a cross sectional detail view of a dental tool collet chuck.
Figure 4:
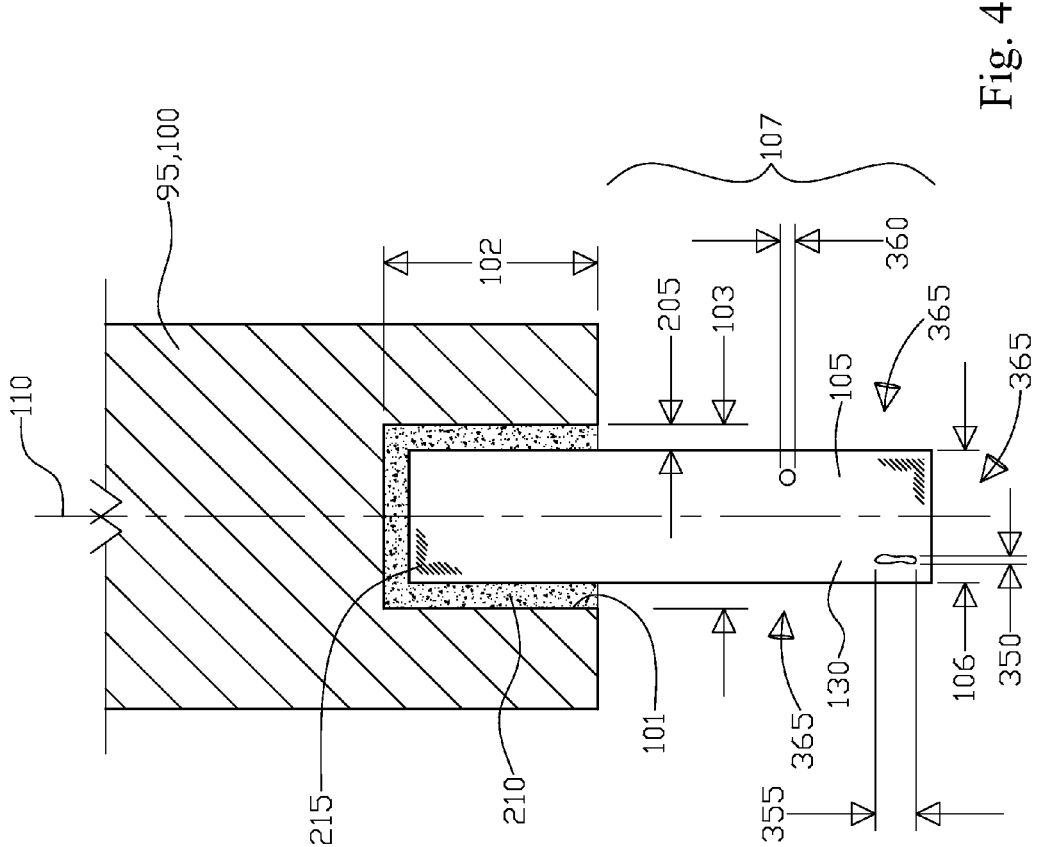
FIG. 4 is a cross sectional detail view 4-4 of FIG. 2 being of the dental tool and tip portion adhesive interface.
Figure 5:
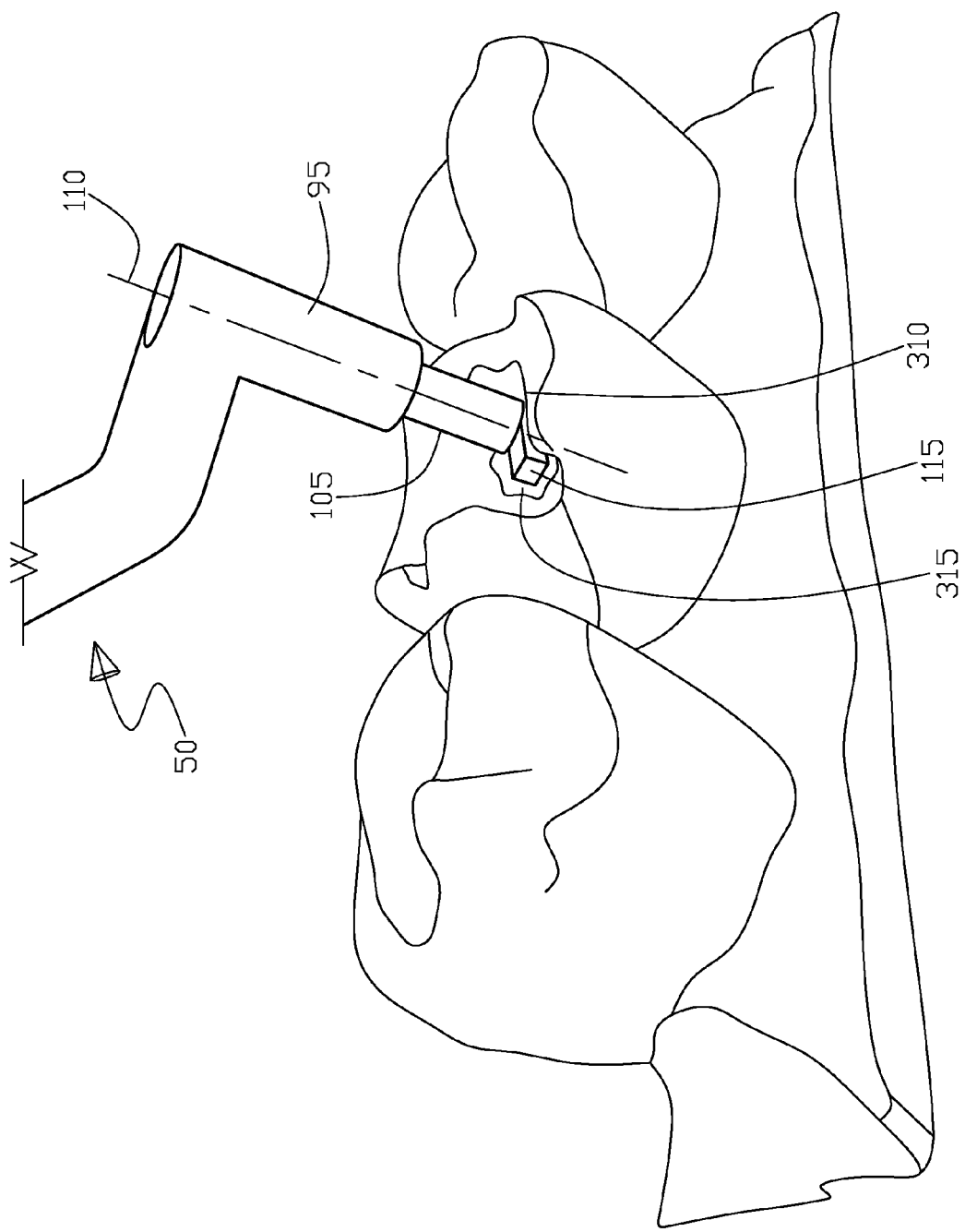
FIG. 5 is a view of the dental tool in use with a hammer head type tool tip configuration.
Figure 6:
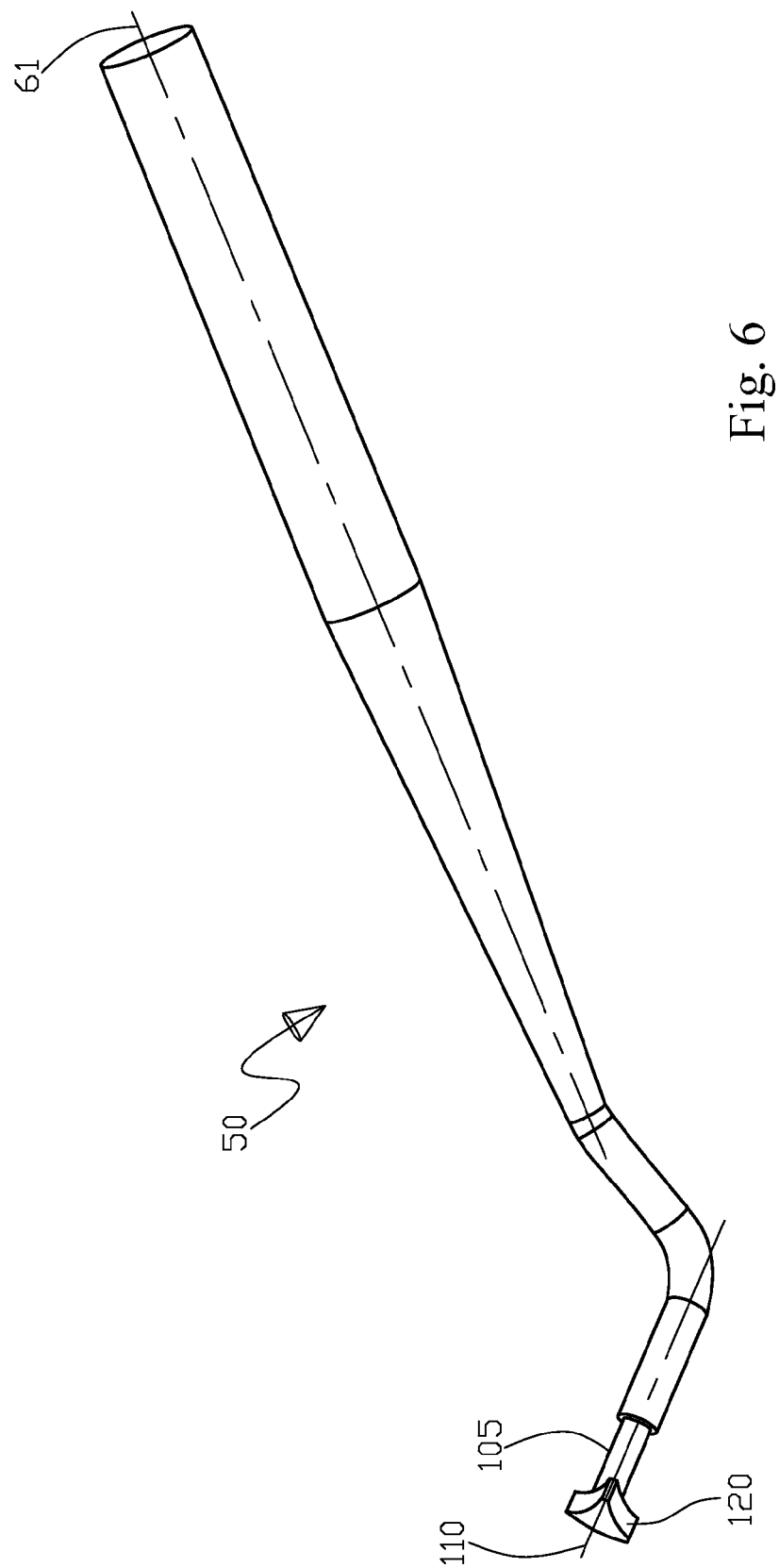
FIG. 6 is a perspective view of the dental tool with an anvil type tool tip configuration.

Starting with FIG. 1 is a perspective view of the dental tool assembly 50 of the preferred embodiment of the present invention, next FIG. 2 is an expanded detail view of the tool tip 105 of the tool assembly 50 of FIG. 1, and FIG. 3 is a cross sectional detail view of a dental tool collet chuck 185 for either the dental tool assembly 50 or 55. Continuing, FIG. 4 is a cross sectional detail view 4-4 of FIG. 2 being of the dental tool 50 or 55 and tip portion 105 adhesive interface 210, FIG. 5 is a view of the dental tool assembly 50 in use with a hammer head 115 type tool tip 105 configuration, and FIG. 6 is a perspective view of the dental tool 50 or 55 with an anvil type 120 tool tip 105 configuration.

Figure 7:
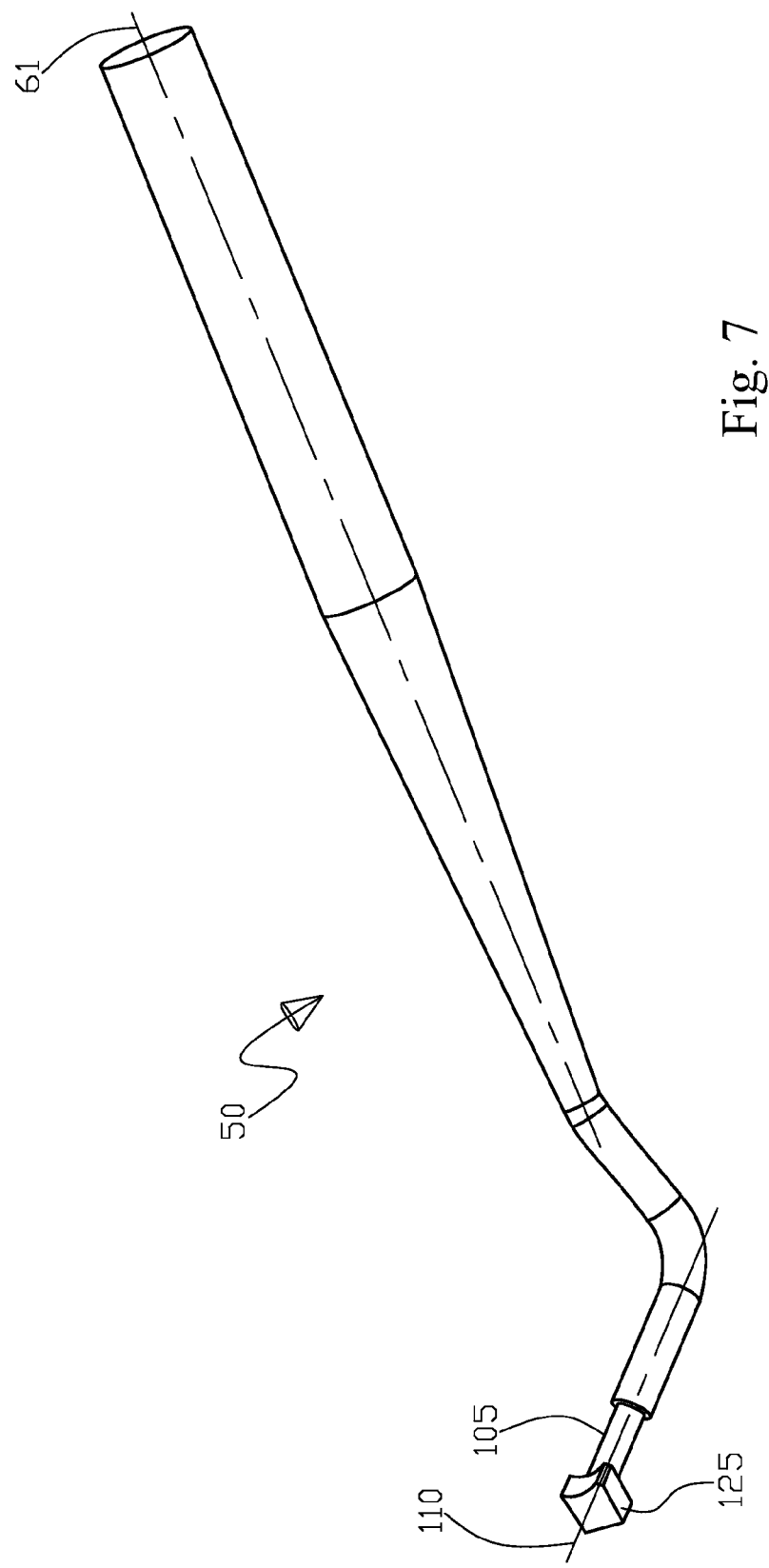
FIG. 7 is a perspective view of parallelepiped type tool tip configuration.
Figure 8:
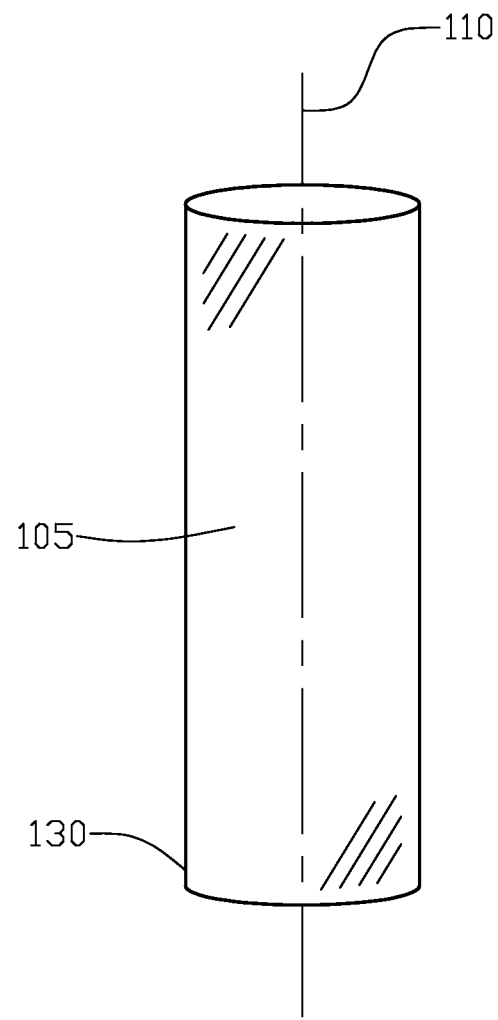
FIG. 8 is a perspective view of a cylindrical type tool tip.
Figure 9:
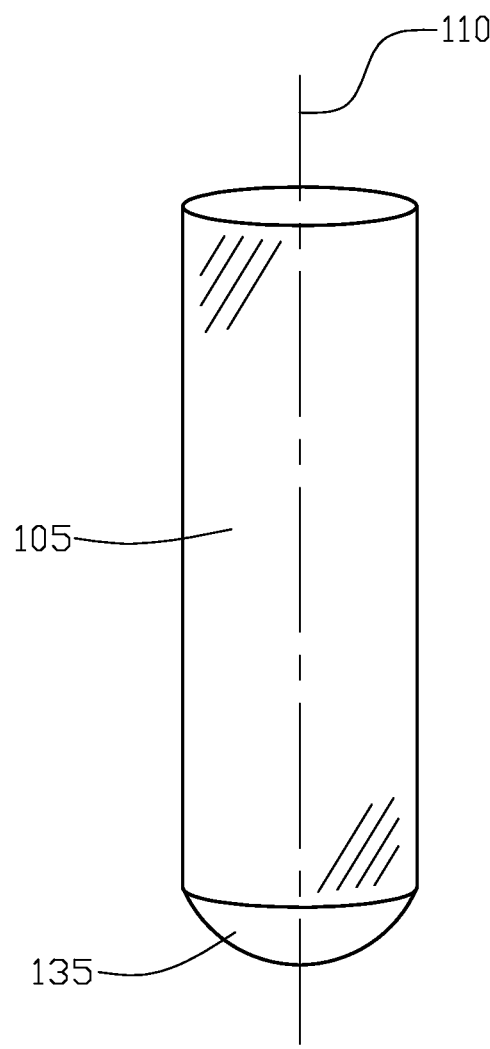
FIG. 9 is a perspective view of a cylindrical type tool tip with a semi-spherical end portion.
Figure 10:
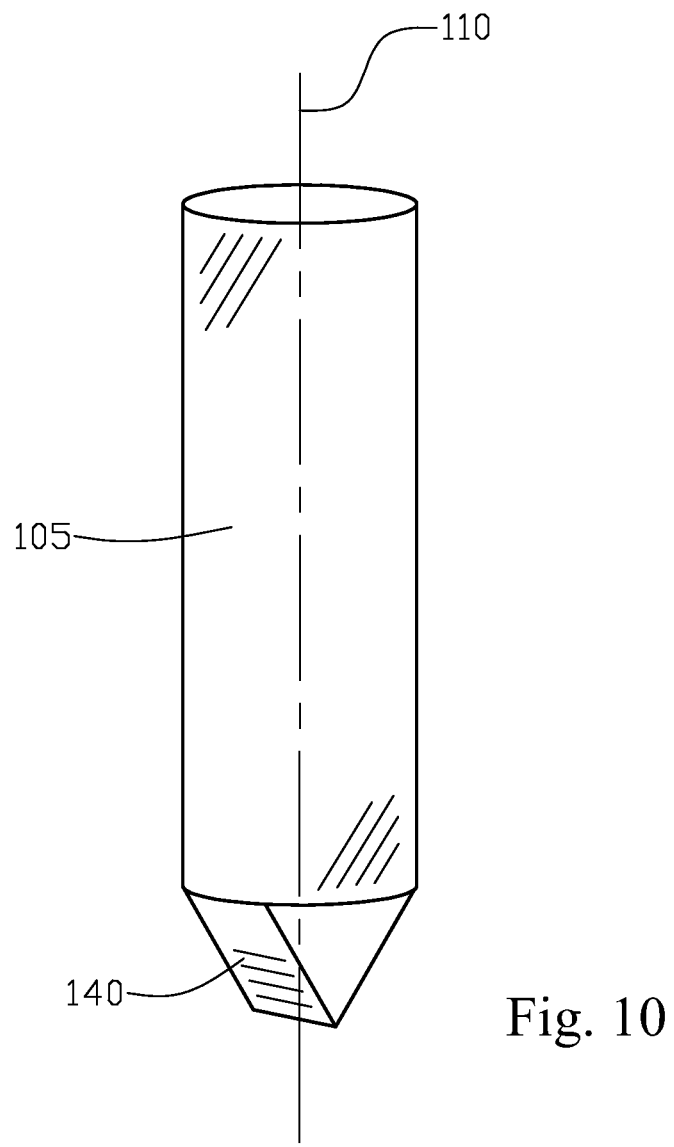
FIG. 10 is a perspective view of a cylindrical type tool tip with a wedge end portion.
Figure 11:
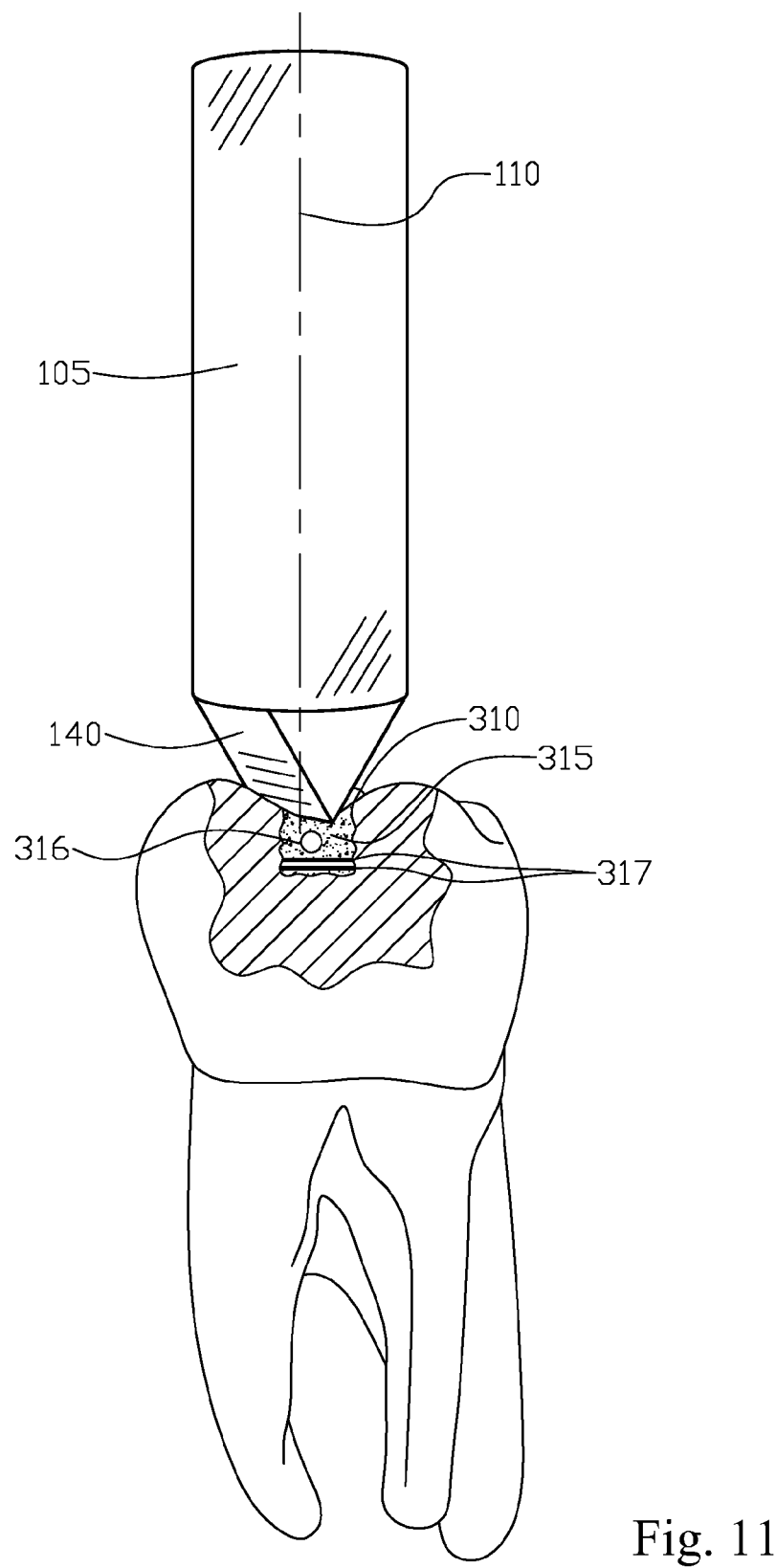
FIG. 11 is a perspective view of a cylindrical type tool tip with a wedge end portion shown in use, wherein the prepared cavity of the tooth is shown in cross section with the composite filler material, layers, and voids or porosity.
Figure 12:
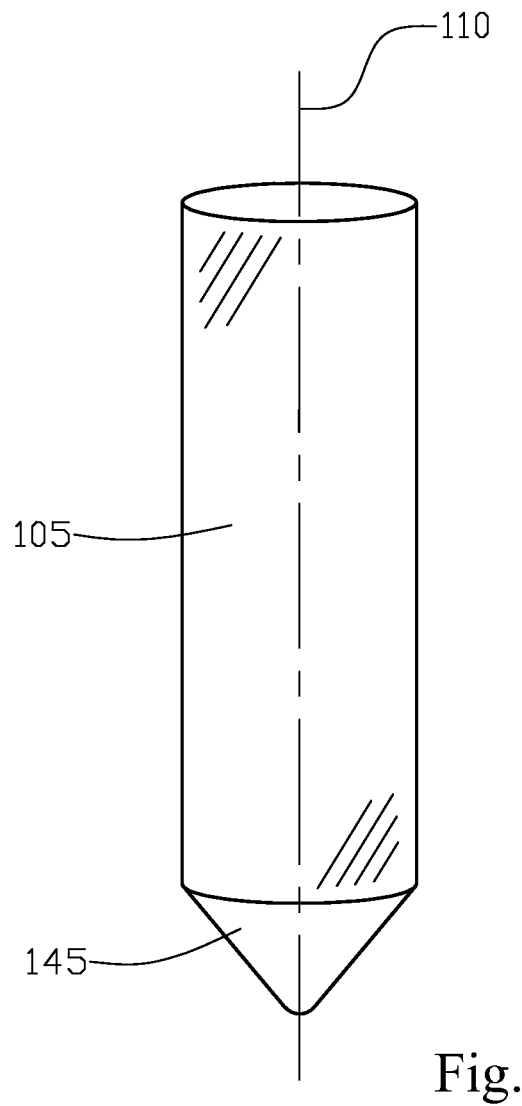
FIG. 12 is a perspective view of a cylindrical type tool tip with a radius point conical end portion.
Figure 13:
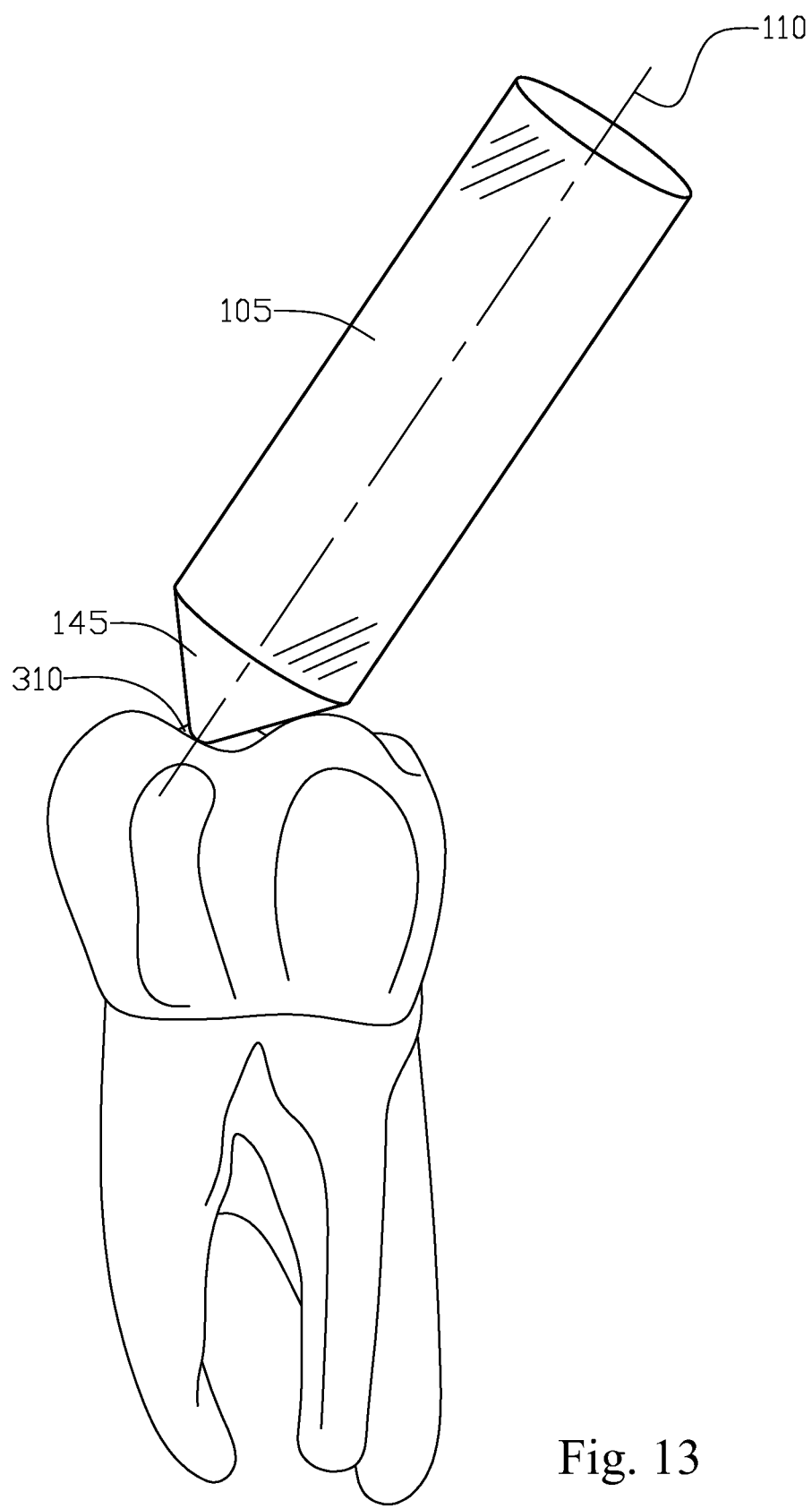
FIG. 13 is a perspective view of a cylindrical type tool tip with a conical end portion shown in use.
Figure 14:
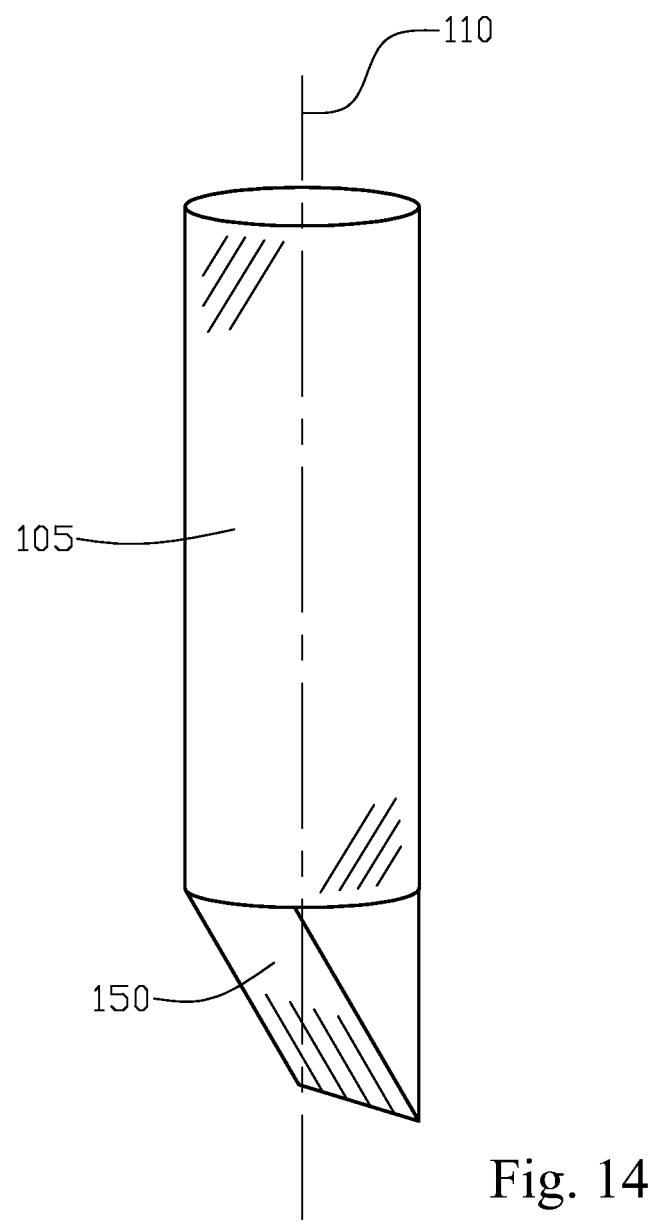
FIG. 14 is a perspective view of a cylindrical type tool tip with a skewed wedge end portion.
Figure 15:
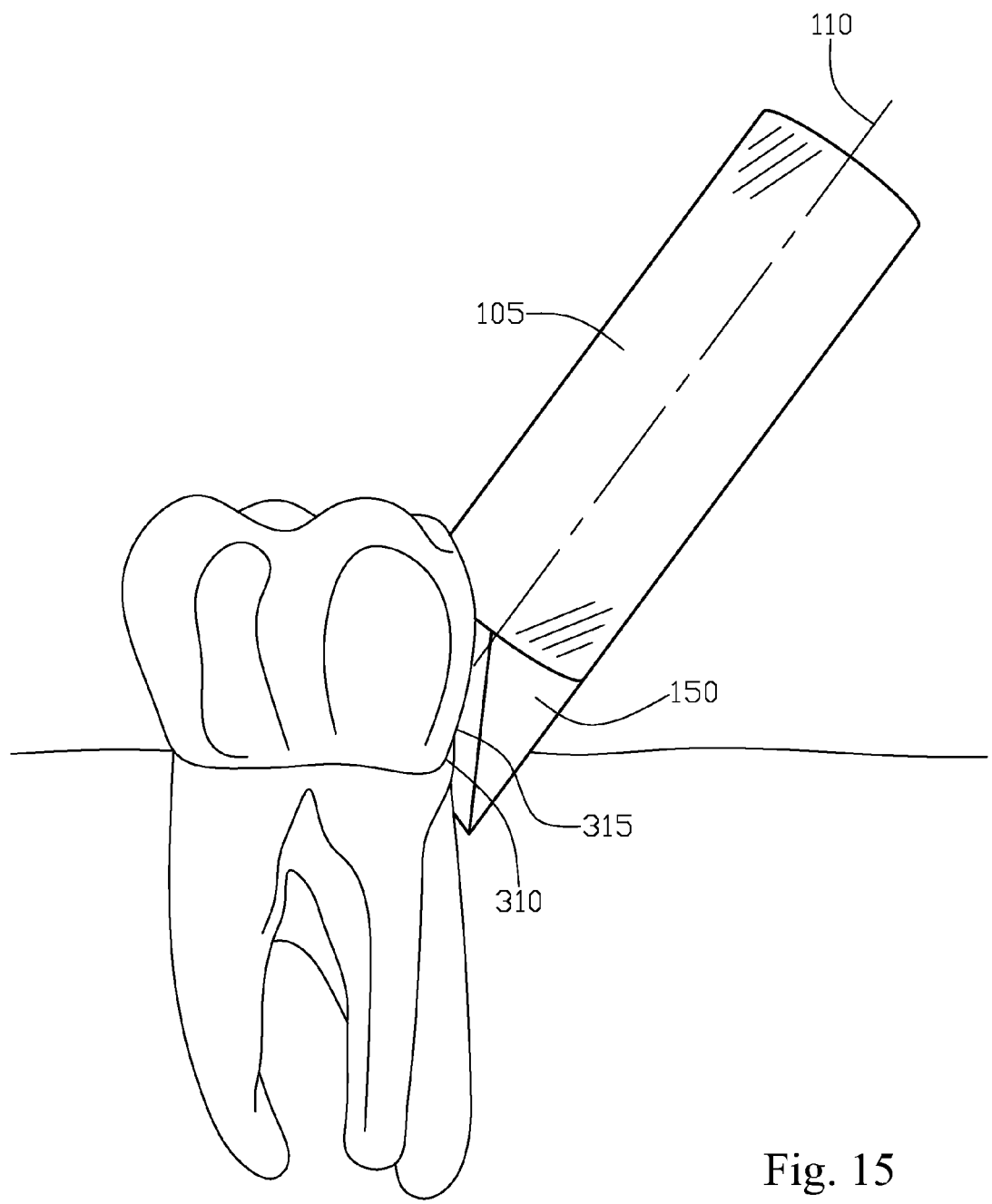
FIG. 15 is a perspective view of a cylindrical type tool tip with a skewed wedge end portion shown in use for a class I-V tooth restoration.

Further, FIG. 7 is a perspective view of parallelepiped type 125 tool tip 105 configuration, FIG. 8 is a perspective view of a cylindrical type 130 tool tip 105, and FIG. 9 is a perspective view of a cylindrical type tool tip with a semi-spherical end 135 portion. Next, FIG. 10 is a perspective view of a cylindrical type tool tip with a wedge end portion 140, FIG. 11 is a perspective view of a cylindrical type tool tip with a wedge end portion 140 shown in use, wherein the prepared cavity 310 of the tooth is shown in cross section with the composite filler material 315, layers 317, and voids 316 or porosity 316 and FIG. 12 is a perspective view of a cylindrical type tool tip with a radius point conical end portion 145. Continuing, FIG. 13 is a perspective view of a cylindrical type tool tip with the radius point conical end portion 145 shown in use, FIG. 14 is a perspective view of a cylindrical type tool tip with a skewed wedge end 150 portion, and FIG. 15 is a perspective view of a cylindrical type tool tip with a skewed wedge end 150 portion shown in use for a class I-V tooth restorations.

Figure 16:
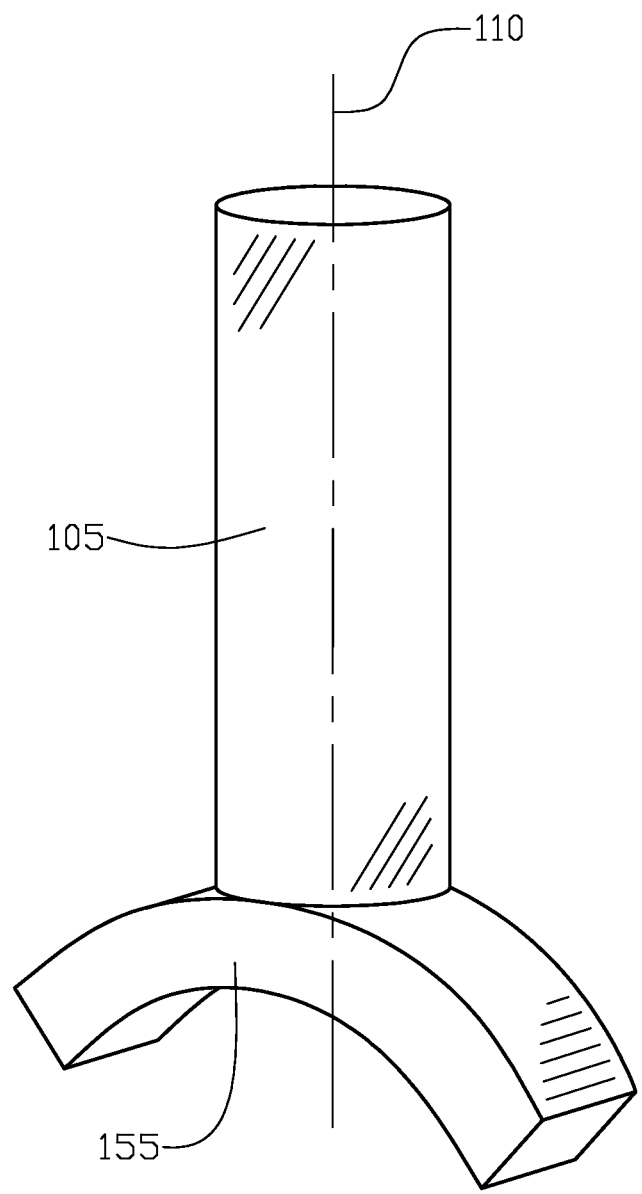
FIG. 16 is a perspective view of a cylindrical type tool tip with an arcuate segment end portion.
Figure 17:
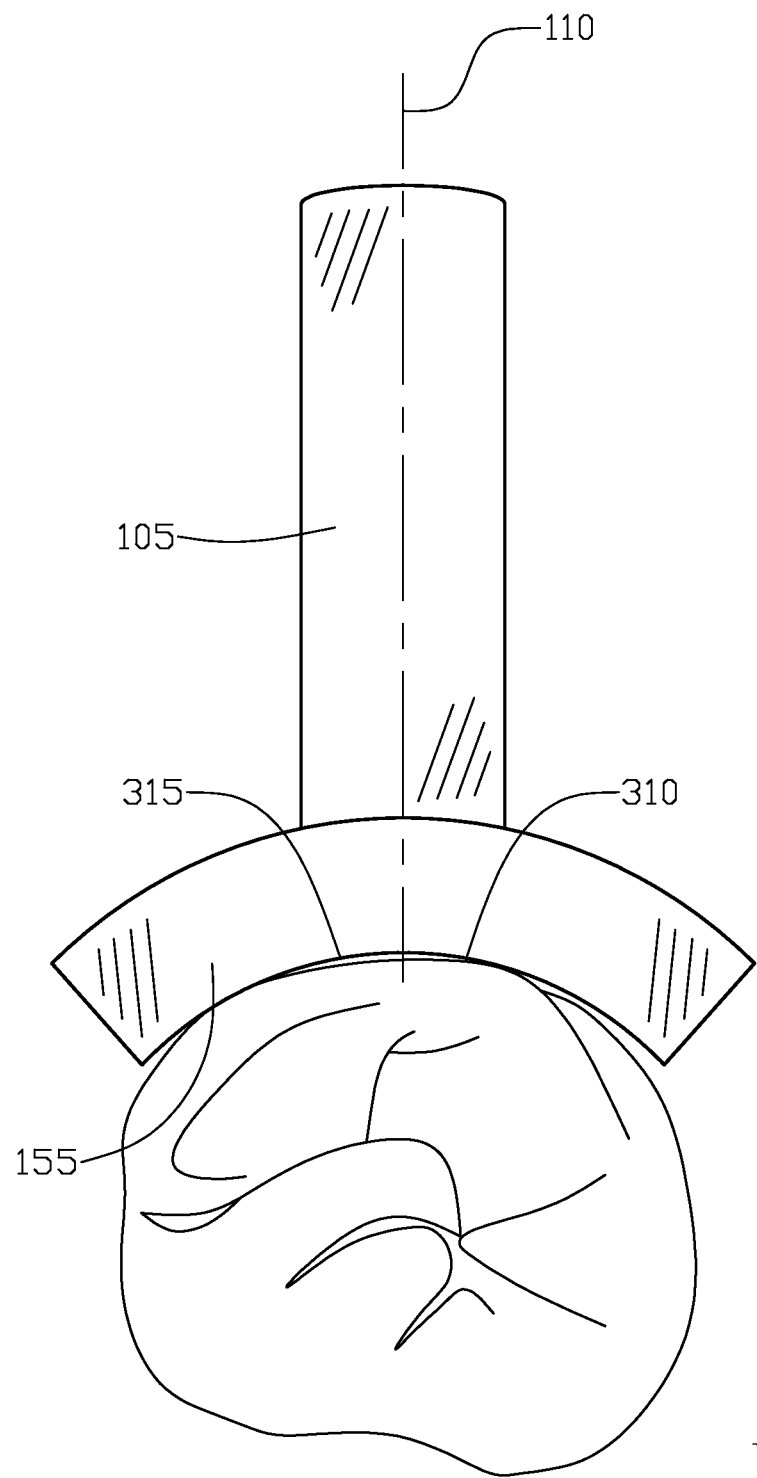
FIG. 17 is a perspective view of a cylindrical type tool tip with an arcuate segment end portion shown in use for a class I-V tooth restoration.
Figure 18:
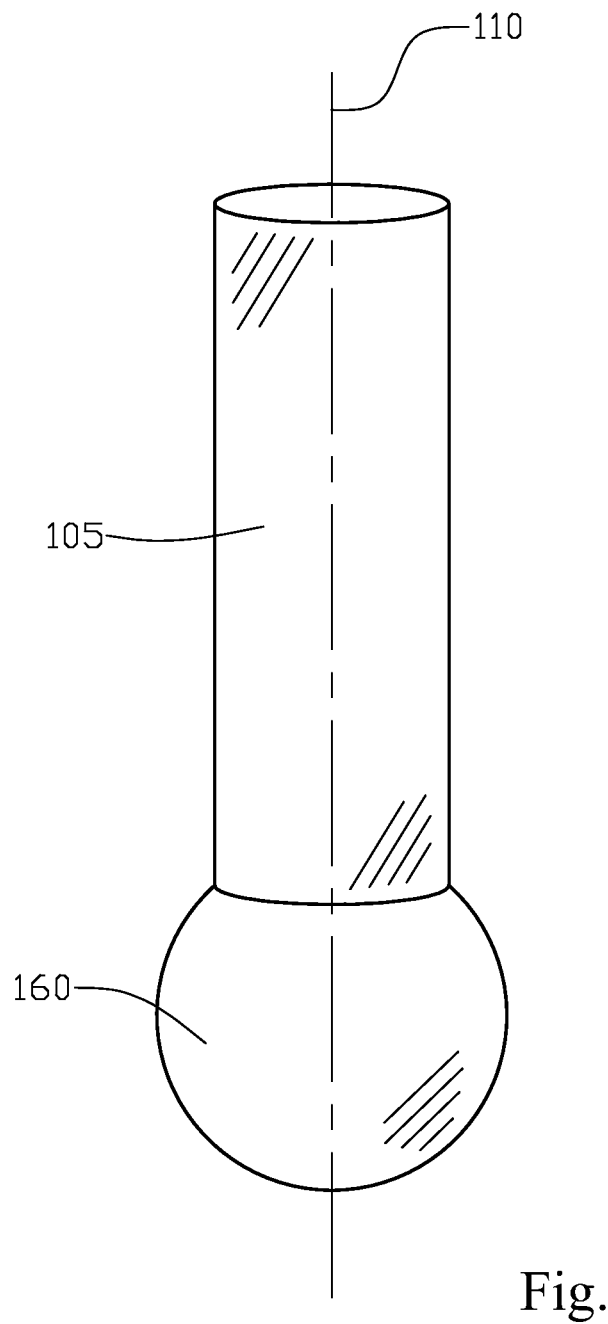
FIG. 18 is a perspective view of a cylindrical type tool tip with a full-spherical end portion.
Figure 19:
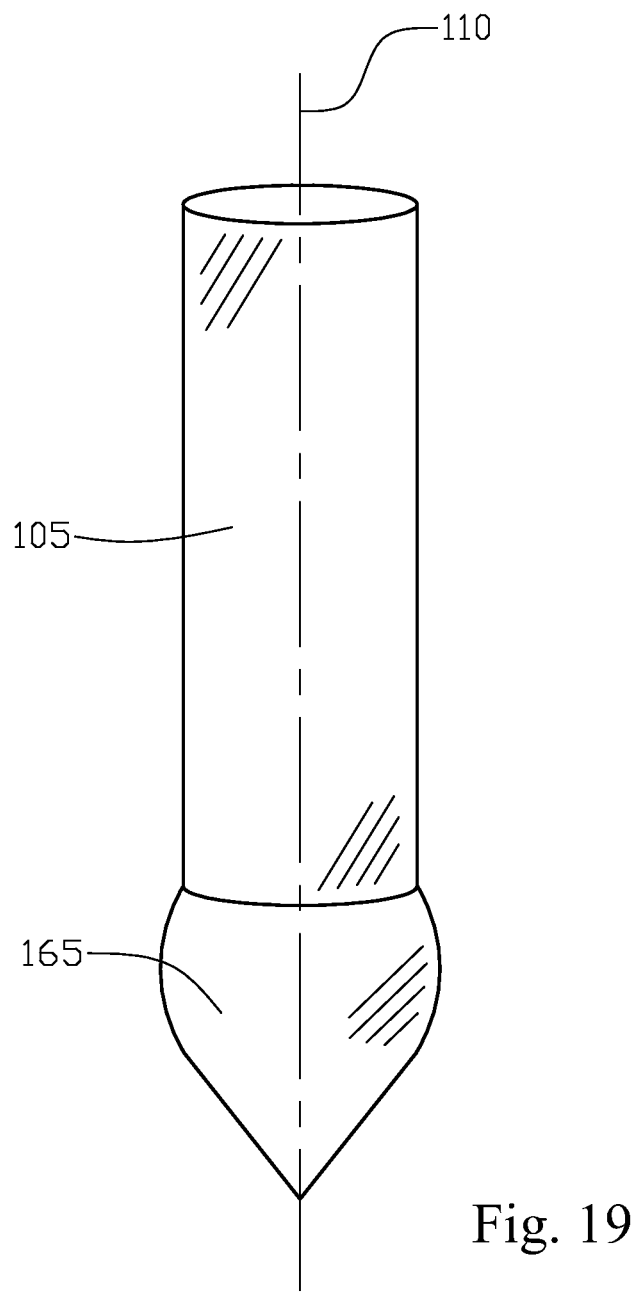
FIG. 19 is a perspective view of a cylindrical type tool tip with a teardrop end portion.
Figure 20:
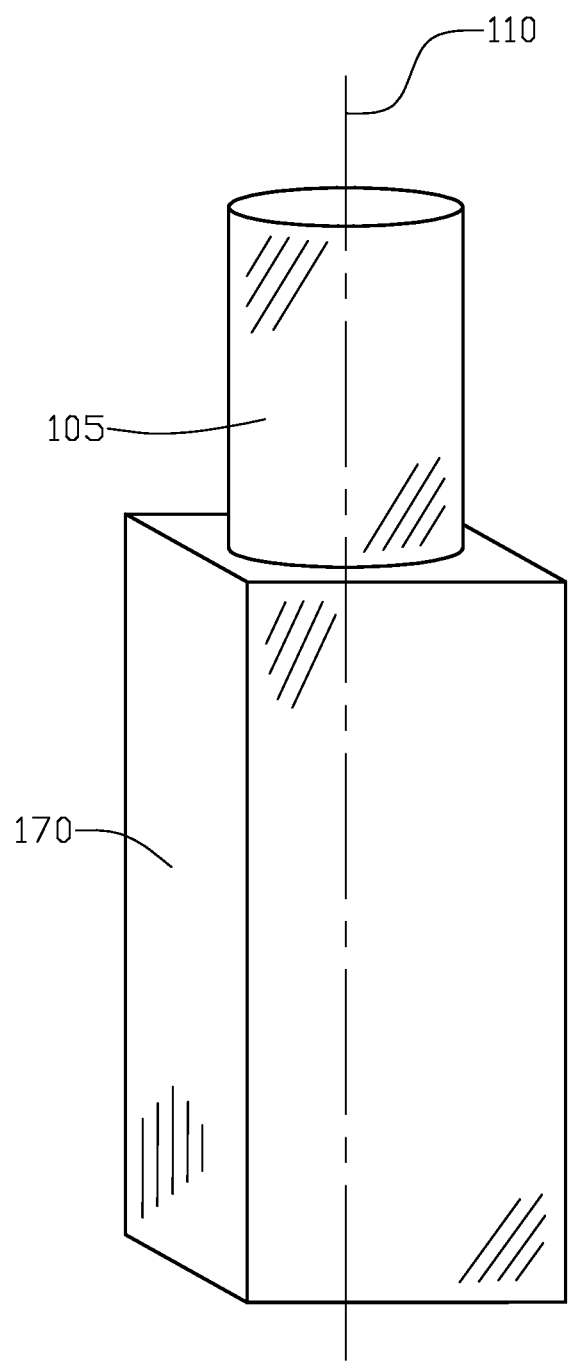
FIG. 20 is a perspective view of a cylindrical type tool tip with a rectangular parallelepiped end portion.
Figure 21:
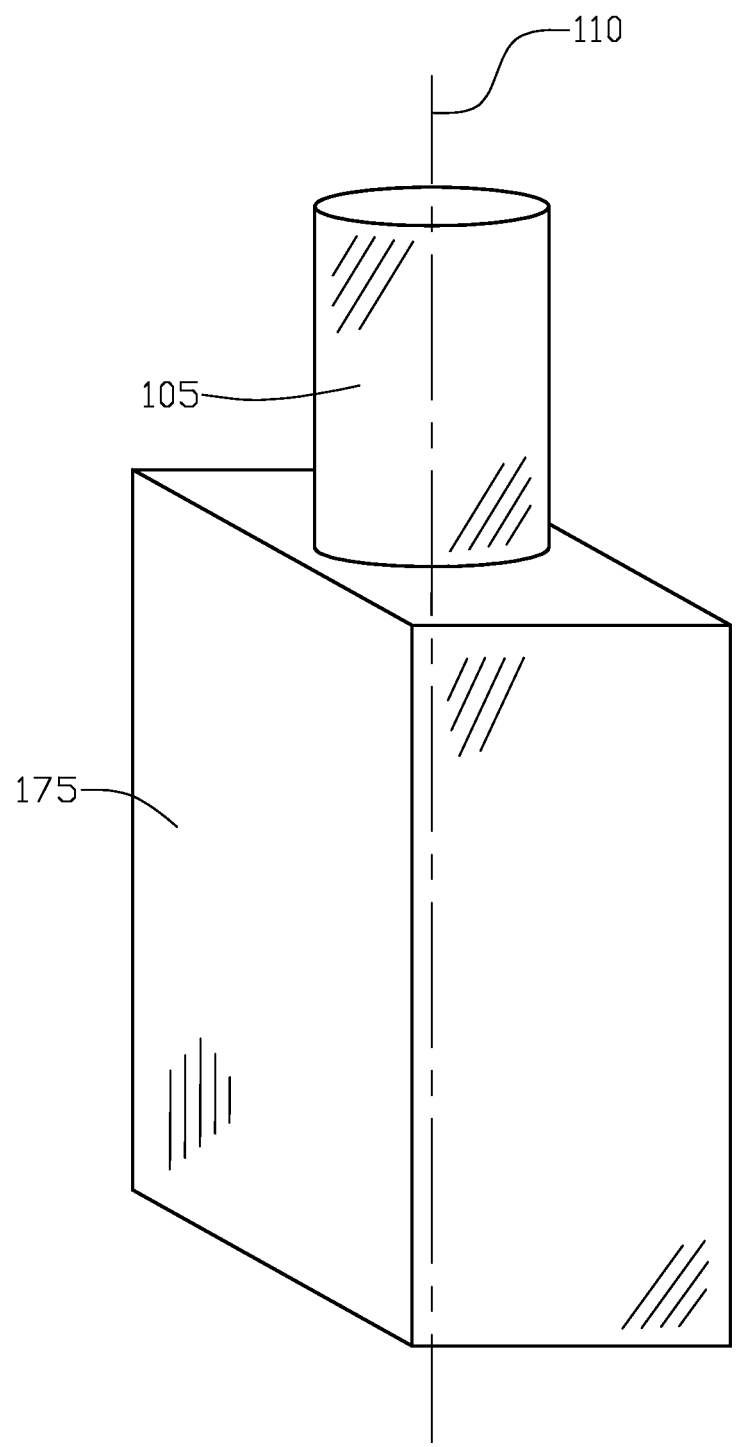
FIG. 21 is a perspective view of a cylindrical type tool tip with a widened rectangular parallelepiped end portion.

Moving onward, FIG. 16 is a perspective view of a cylindrical type tool tip with an arcuate segment end 155 portion, FIG. 17 is a perspective view of a cylindrical type tool tip with an arcuate segment end 155 portion shown in use for a class I-V tooth restorations, and FIG. 18 is a perspective view of a cylindrical type tool tip with a full-spherical end 160 portion. Further, FIG. 19 is a perspective view of a cylindrical type tool tip with a teardrop end portion 165, FIG. 20 is a perspective view of a cylindrical type tool tip with a rectangular parallelepiped end 170 portion, and FIG. 21 is a perspective view of a cylindrical type tool tip with a widened rectangular parallelepiped end 175 portion.

Figure 22:
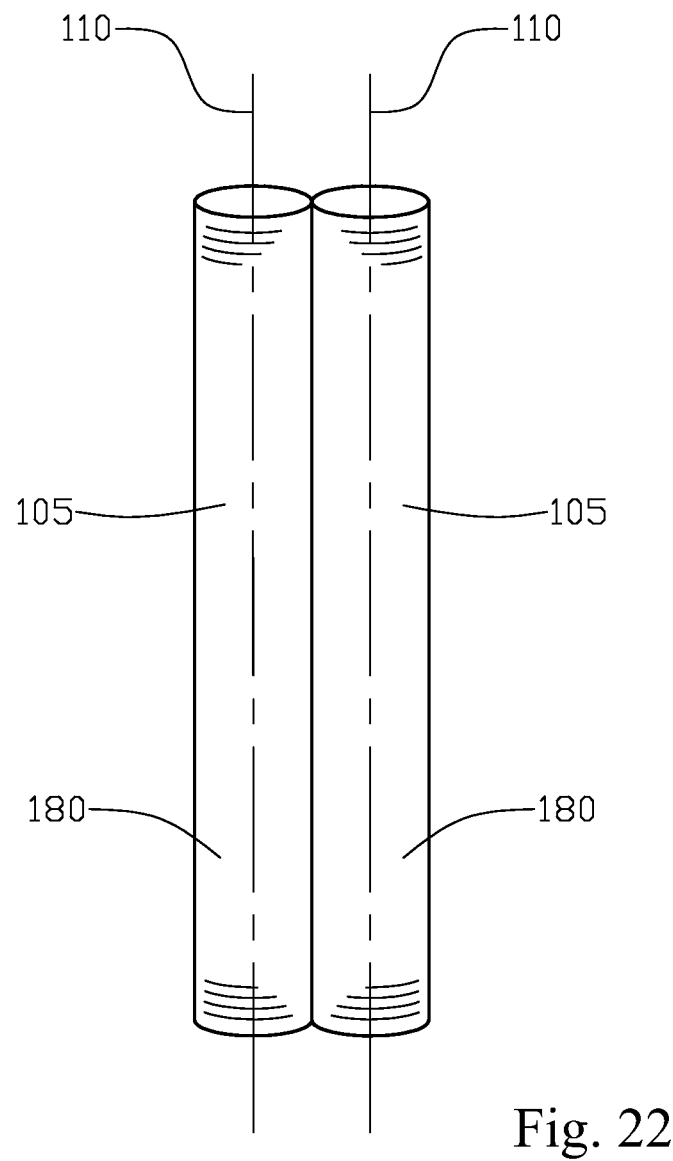
FIG. 22 is a perspective view of a dual cylindrical type tool tip.
Figure 23:
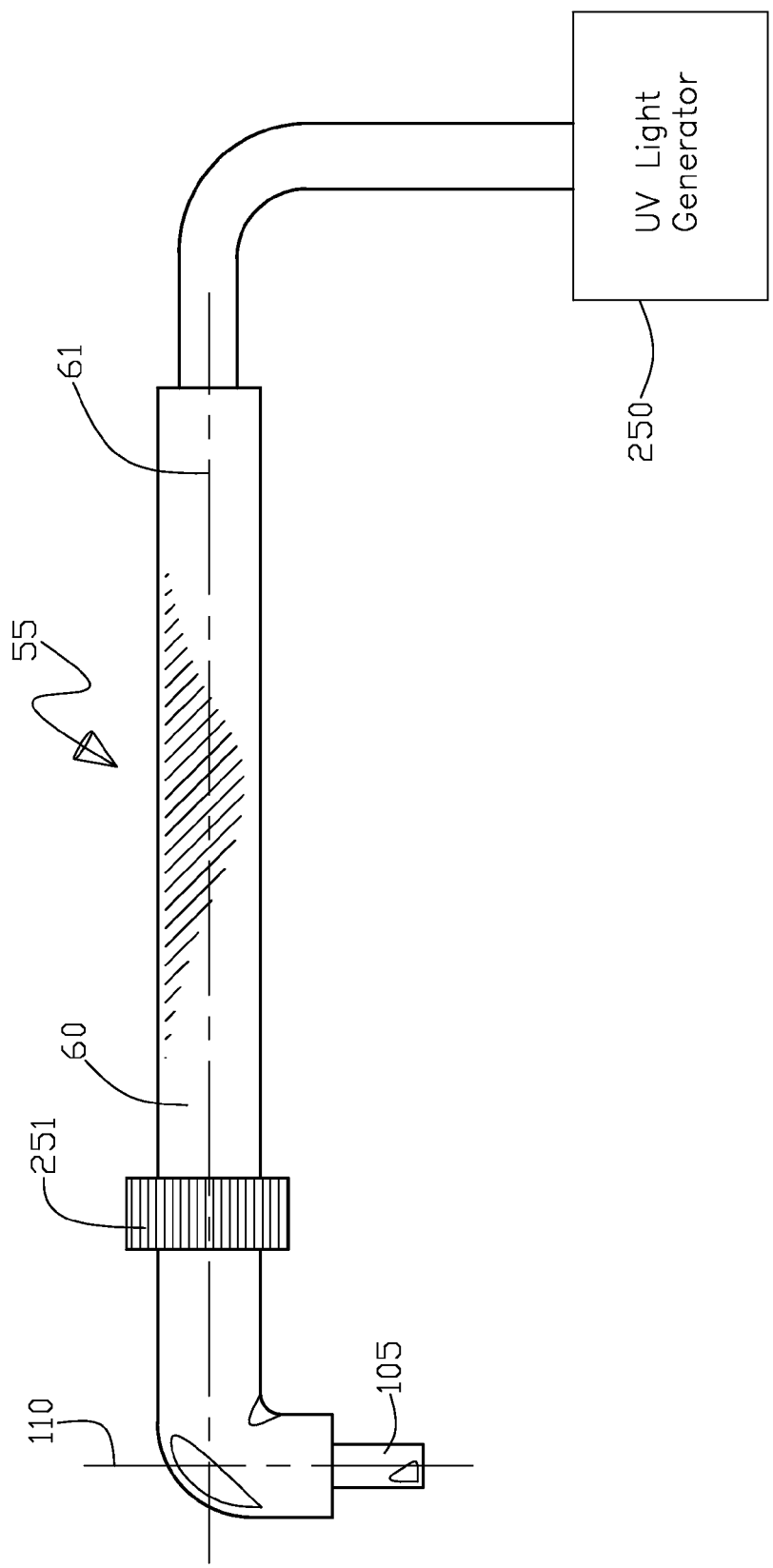
FIG. 23 shows a side elevation view of an alternative embodiment of the present invention including a combination of the dental tool tip portion of the present invention and a photo-polymerization light curing apparatus, wherein the curing light communicates within the dental tool and through the light transmittable tip portion.
Figure 24:
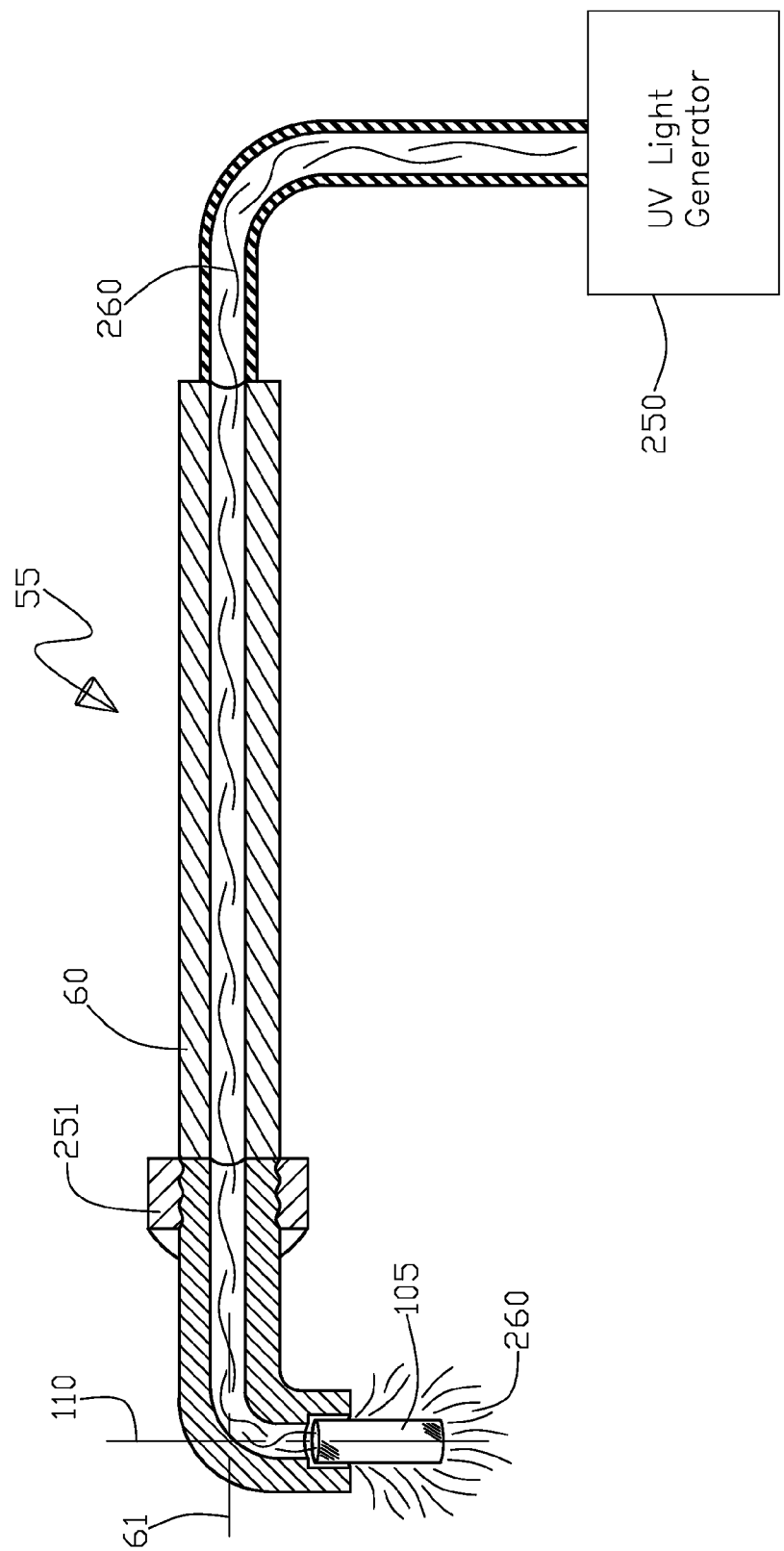
FIG. 24 shows a side elevation cross sectional view of FIG. 23 for the alternative embodiment of the present invention including a combination of the dental tool tip portion of the present invention and a photo-polymerization light curing apparatus, wherein the curing light communicates within the dental tool and through the light transmittable tip portion, wherein the tool tip portion and the photo-polymerization light curing apparatus are detachable adjacent to the tool tip portion.

Continuing, FIG. 22 is a perspective view of a dual cylindrical type tool tip 180 and FIG. 23 shows a side elevation view of an alternative embodiment 55 of the present invention including a combination of the dental tool tip portion 105 of the present invention 50 and a photo-polymerization light curing apparatus 250, wherein the curing light communicates 260 within the dental tool 55 grip 60 and through the light transmittable tip portion 105. Next, FIG. 24 shows a side elevation cross sectional view of FIG. 23 for the alternative embodiment 55 of the present invention including a combination of the dental tool tip portion 105 of the present invention 50 and a photo-polymerization light curing apparatus 250, wherein the curing light communicates 260 within the dental tool 55 grip 60 and through the light transmittable tip portion 105, wherein the tool tip portion 105 and the photo-polymerization light curing apparatus 250 are detachable 251 adjacent to the tool tip portion 105.

Figure 25:
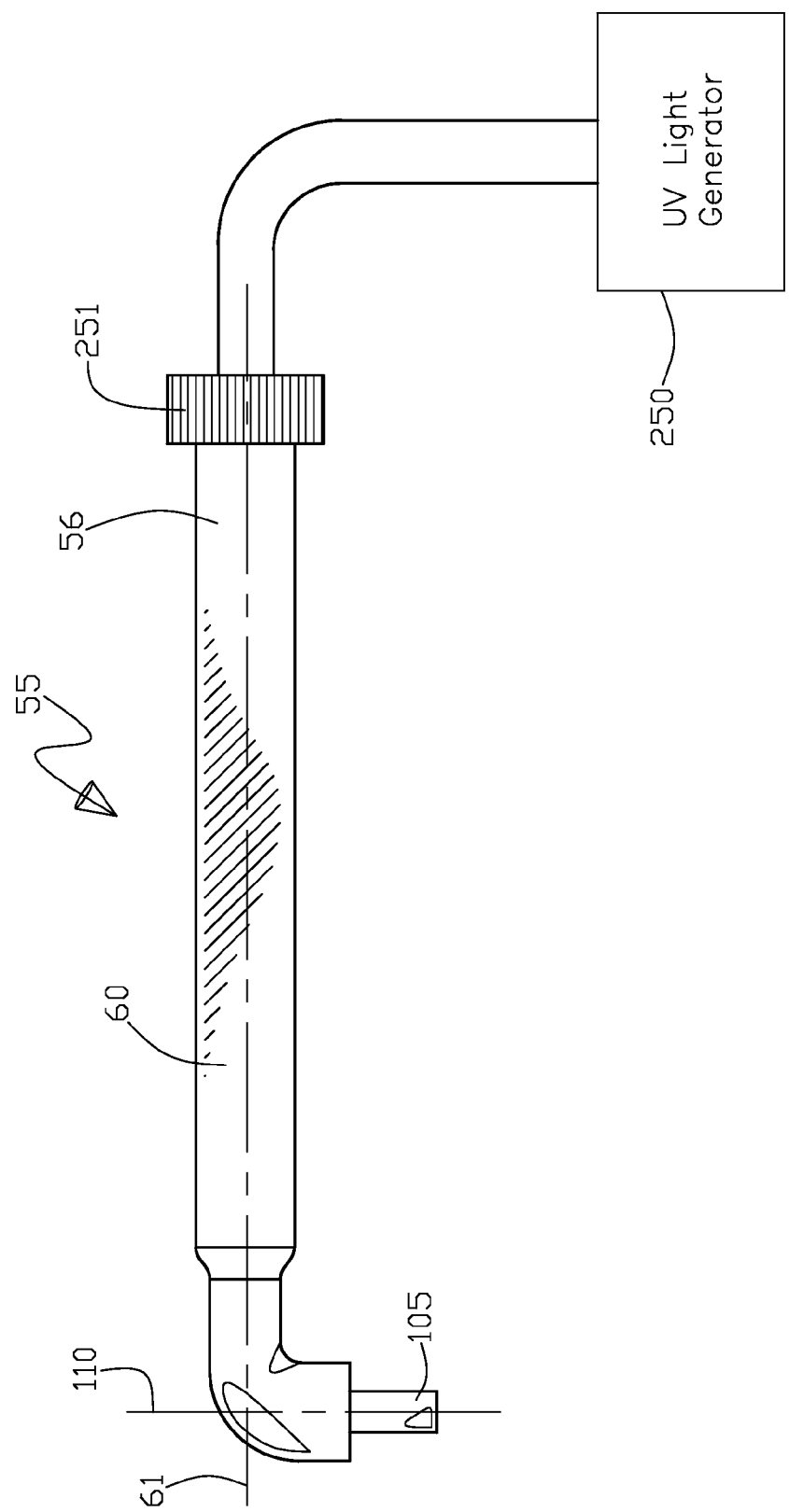
FIG. 25 shows a side elevation view of an alternative embodiment of the present invention including a combination of the dental tool tip portion of the present invention and a photo-polymerization light curing apparatus, wherein the curing light communicates within the dental tool and through the light transmittable tip portion.
Figure 26:
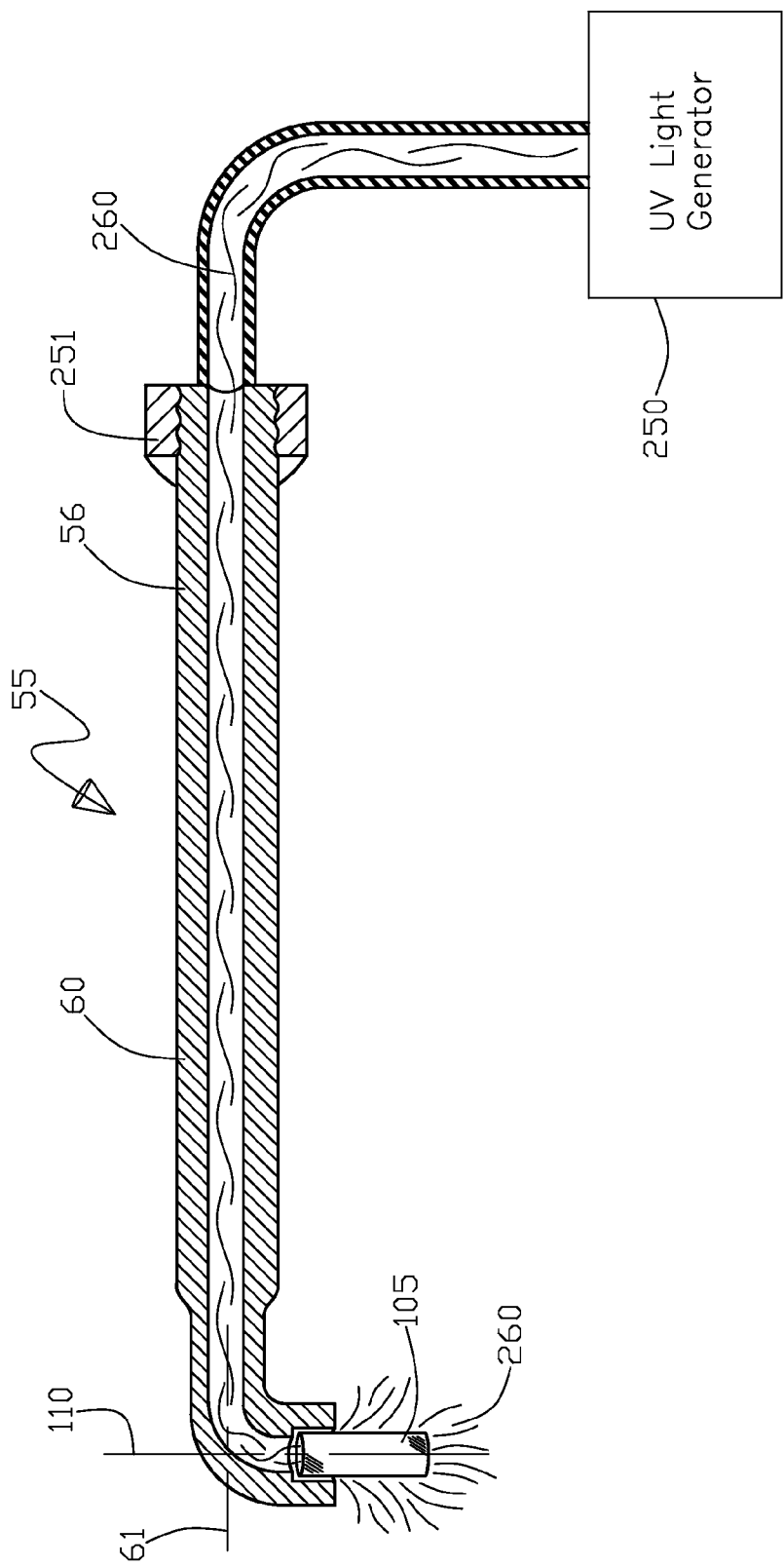
FIG. 26 shows a side elevation cross sectional view of FIG. 25 for the alternative embodiment of the present invention including a combination of the dental tool tip portion of the present invention and a photo-polymerization light curing apparatus, wherein the curing light communicates within the dental tool and through the light transmittable tip portion, wherein the tool tip portion and the photo-polymerization light curing apparatus are detachable adjacent to the proximal tool portion.

Further, FIG. 25 shows a side elevation view of an alternative embodiment 55 of the present invention including a combination of the dental tool tip portion 105 of the present invention 50 and a photo-polymerization light curing apparatus 250, wherein the curing light communicates 260 within the dental tool 55 grip 60 and through the light transmittable tip portion 105. Next, FIG. 26 shows a side elevation cross sectional view of FIG. 25 for the alternative embodiment 55 of the present invention including a combination of the dental tool tip portion 105 of the present invention 50 and a photo-polymerization light curing apparatus 250, wherein the curing light communicates 260 within the dental tool 50 grip 60 and through the light transmittable tip portion 105, wherein the tool tip portion 105 and the photo-polymerization light curing apparatus 250 are detachable 251 adjacent to the proximal tool portion 56.

Figure 27:
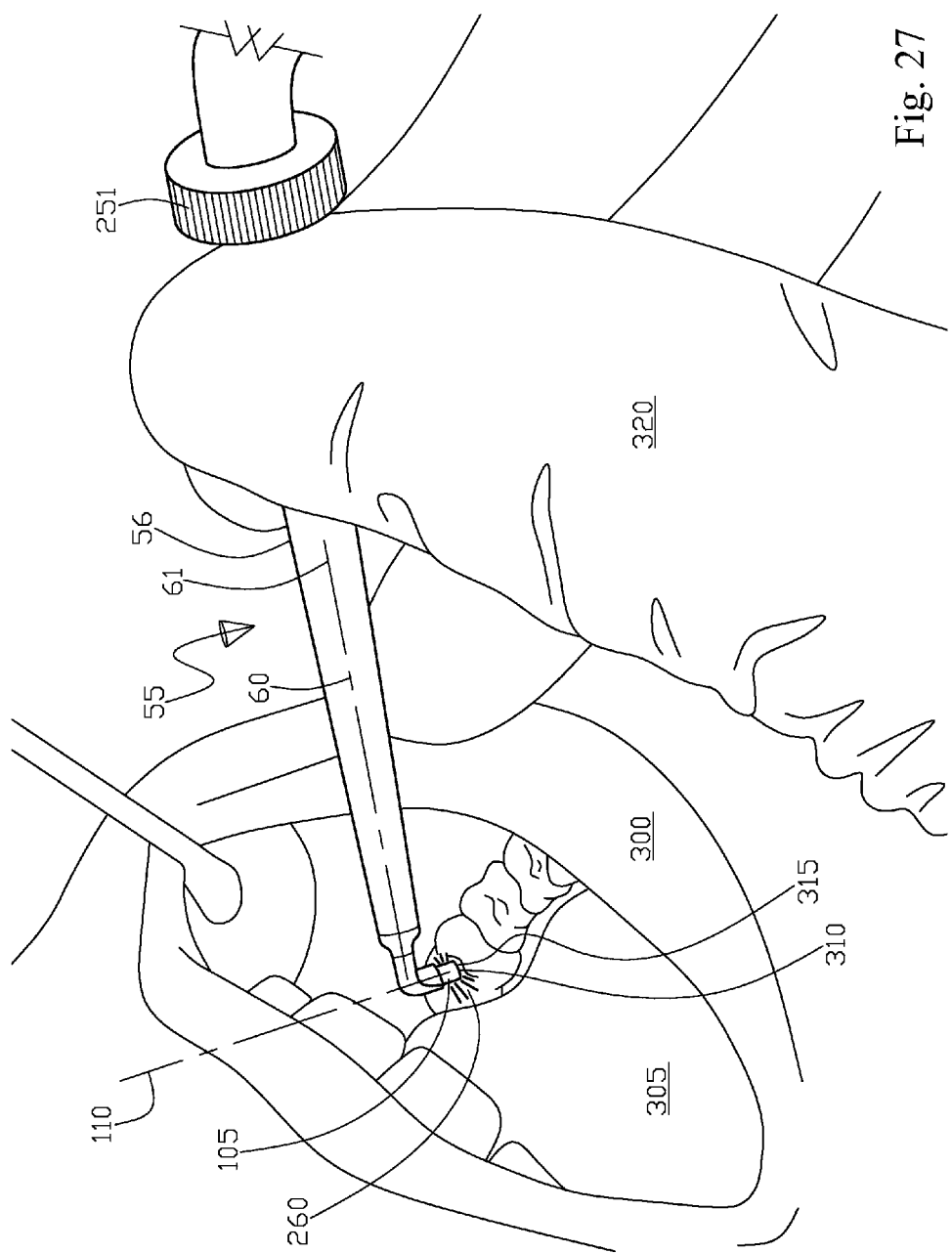
FIG. 27 shows a perspective use view of the combined dental tool tip portion of the present invention and the photo-polymerization light curing apparatus being either from FIG. 23 or 25.
Figure 28:
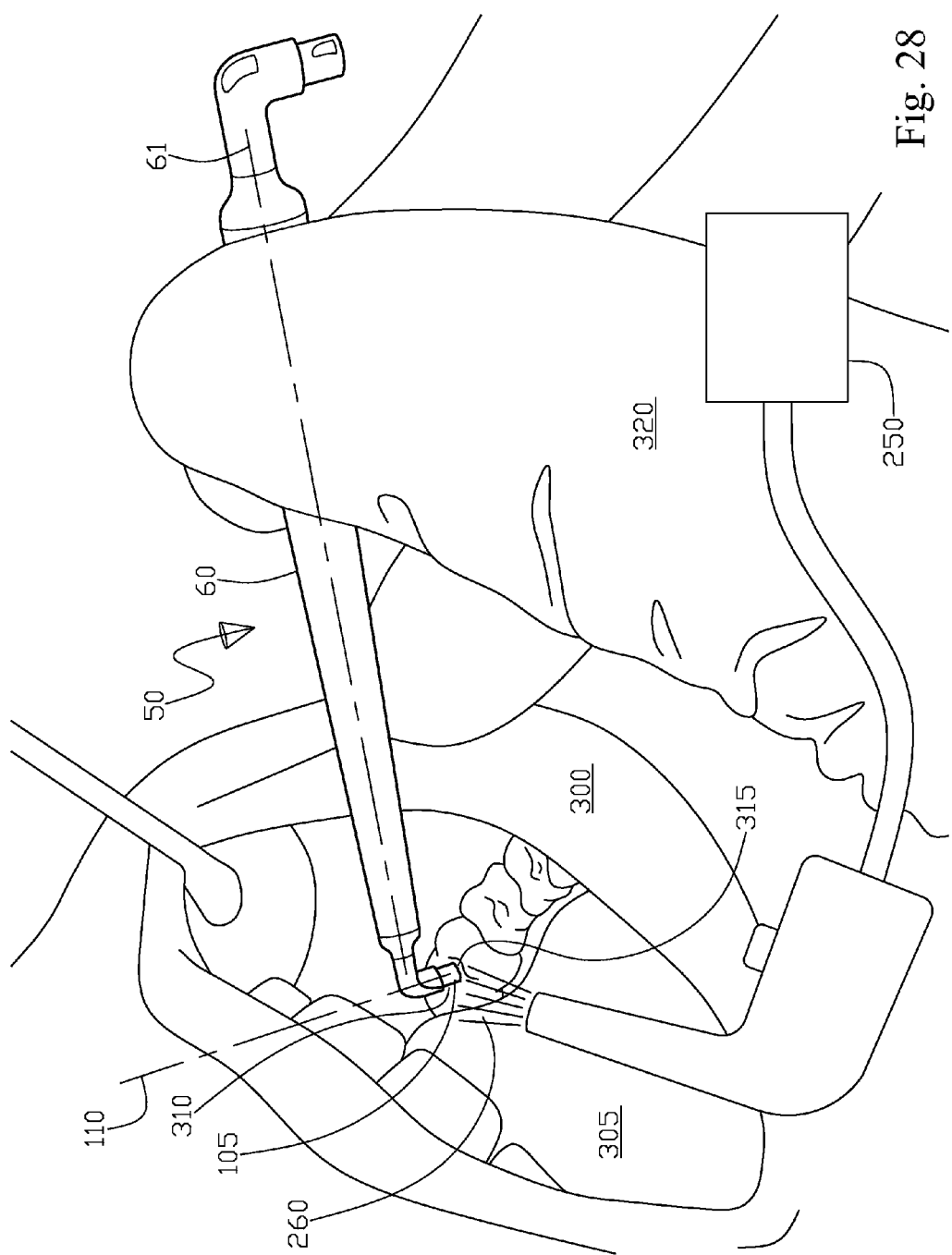
FIG. 28 shows a perspective use view of the separate dental tool tip portion of the present invention and the independently employed photo-polymerization light curing apparatus.
Figure 29:
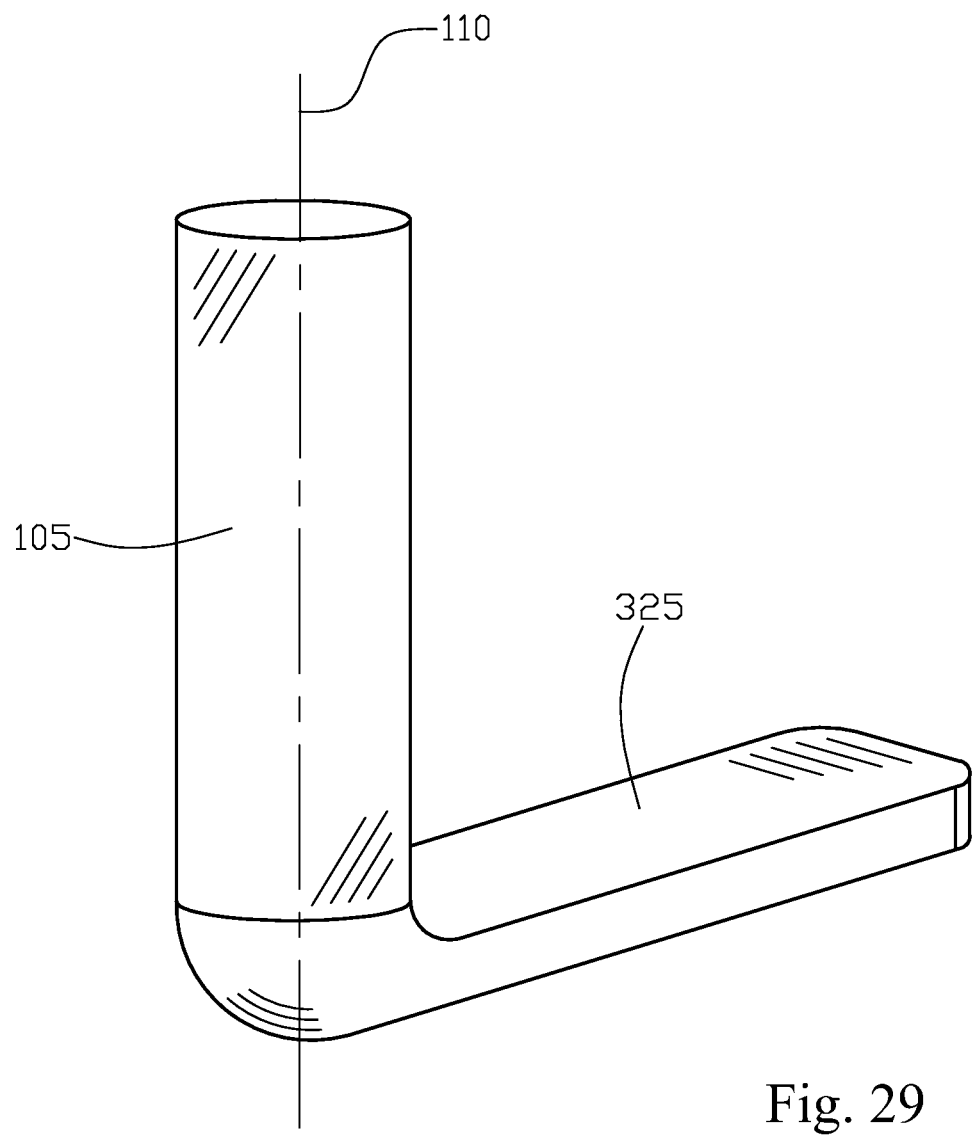
FIG. 29 shows a perspective view of a tool tip with a right angled planar extension in the form of a hoe shape.
Figure 30:
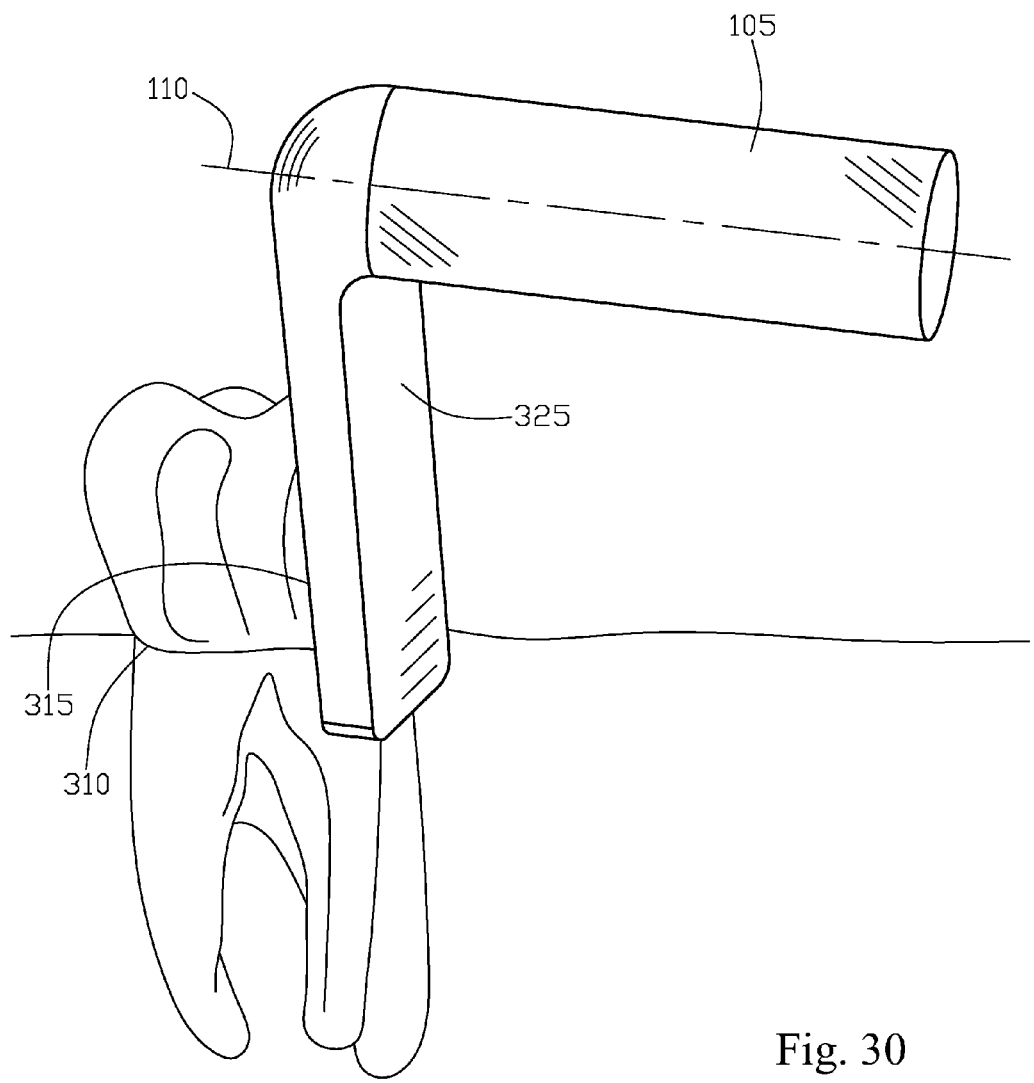
FIG. 30 shows a use perspective view of the tool tip with the right angled planar extension in the form of a hoe shape being used on the side of the tooth at the gum line
Figure 31:
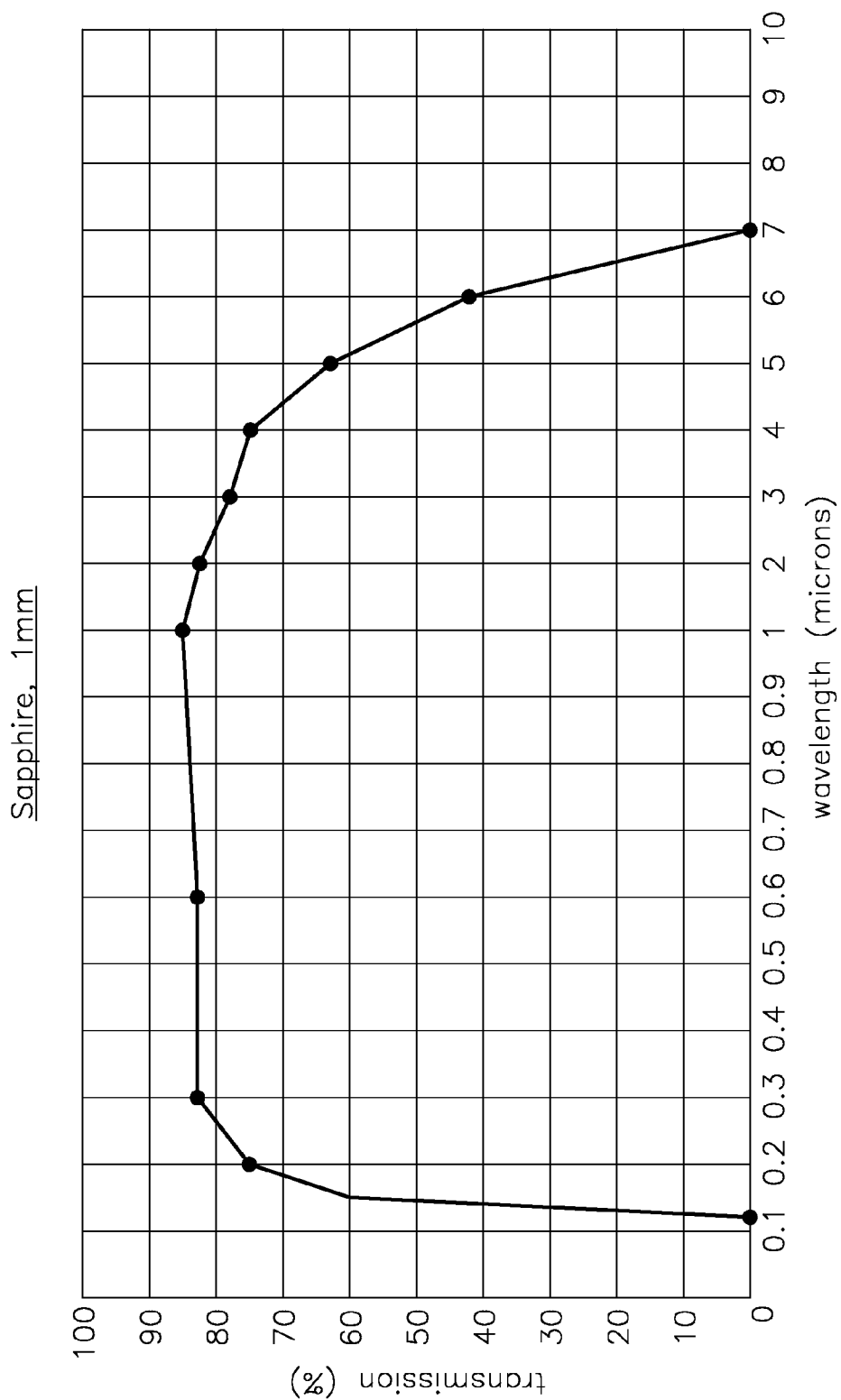
FIG. 31 shows a Sapphire percentage light transmission chart for a one millimeter section of Sapphire material over a range of wavelengths.
Figure 32:
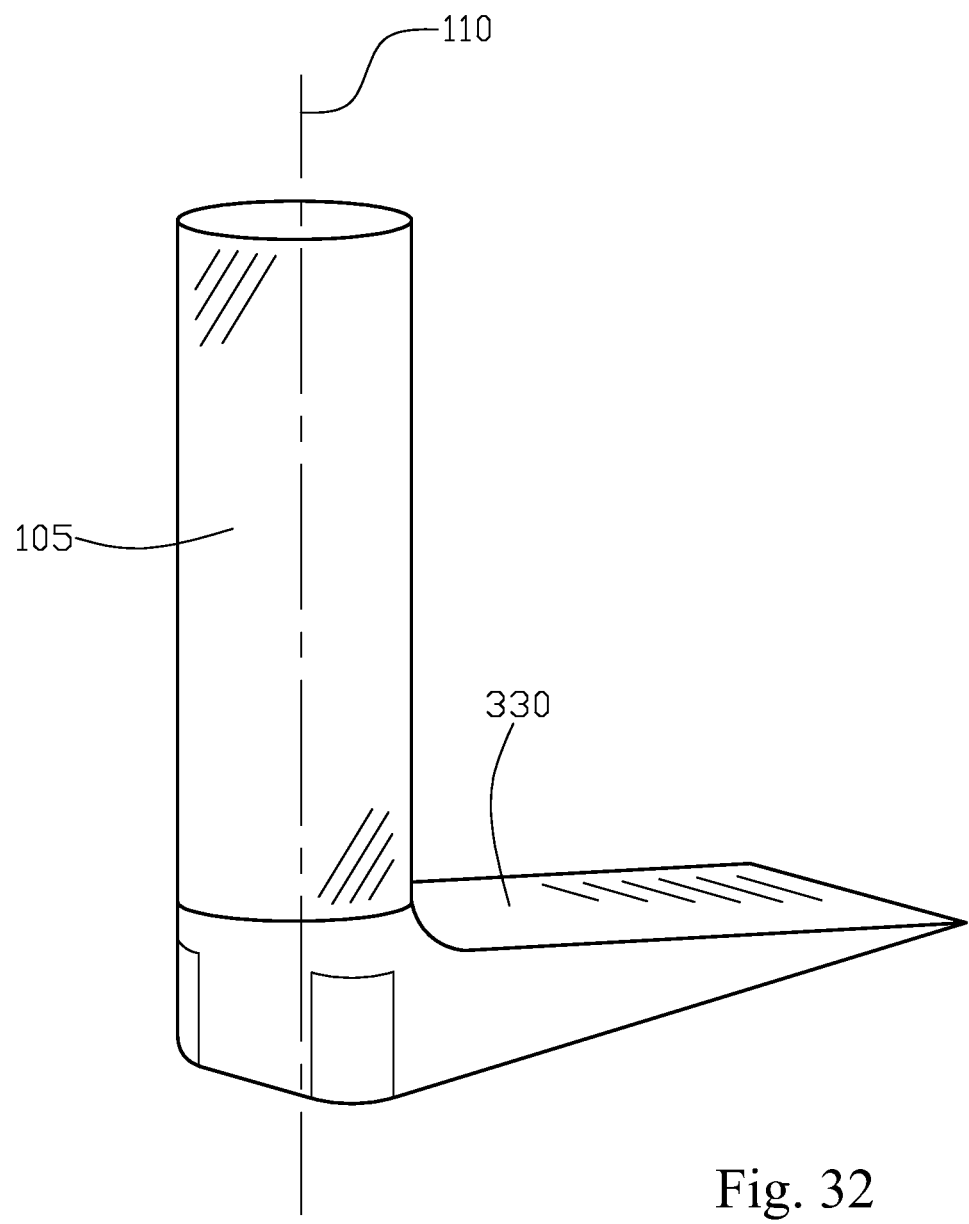
FIG. 32 shows a perspective view of a tool tip with a right angled planar extension that is tapered in the form of a hoe shape.
Figure 33:
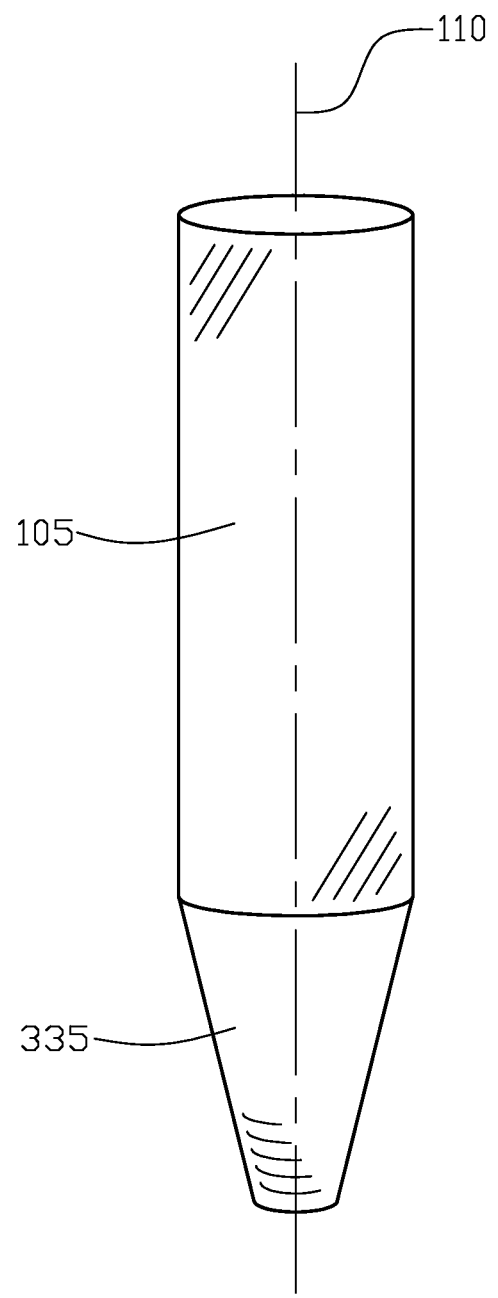
FIG. 33 shows a perspective view of a tool tip with a with an extended conical end portion.
Figure 34:
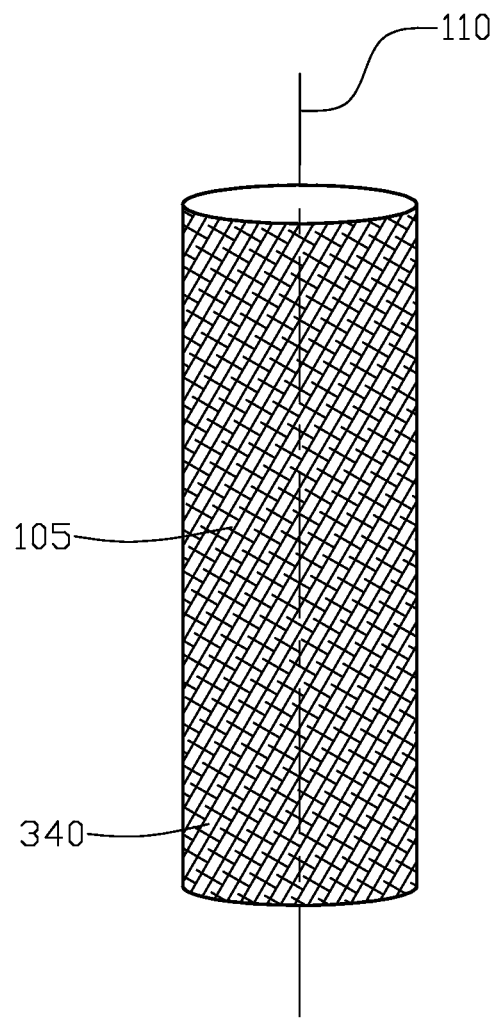
FIG. 34 shows a perspective view of a cylindrical tool tip with a light diffusing outer surface.

Continuing, FIG. 27 shows a perspective use view of the combined dental tool 55 tip portion 105 of the present invention 50 and the photo-polymerization light curing apparatus 250 being either from FIG. 23 or 25 and FIG. 28 shows a perspective use view of the separate dental tool tip portion 105 of the present invention 50 and the independently employed photo-polymerization light curing apparatus 250. Further FIG. 29 shows a perspective view of a tool tip 105 with a right angled planar extension in the form of a hoe shape 325, and FIG. 30 shows a use perspective view of the tool tip 105 with the right angled planar extension in the form of a hoe shape 325 being used on the side of the tooth 310 at the gum line to hold the composite filler material 315 in place while curing. Next, FIG. 31 shows a Sapphire material percentage light transmission chart for a one millimeter section of Sapphire material over a range of wavelengths and FIG. 32 shows a perspective view of a tool tip 105 with a right angled planar extension in the form of a hoe shape that is tapered 330. Continuing, FIG. 33 shows a perspective view of a tool tip 105 with a with an extended conical end portion 335 and FIG. 34 shows a perspective view of a cylindrical tool tip 105 with a with a light diffusing outer surface 340.

Figure 35:
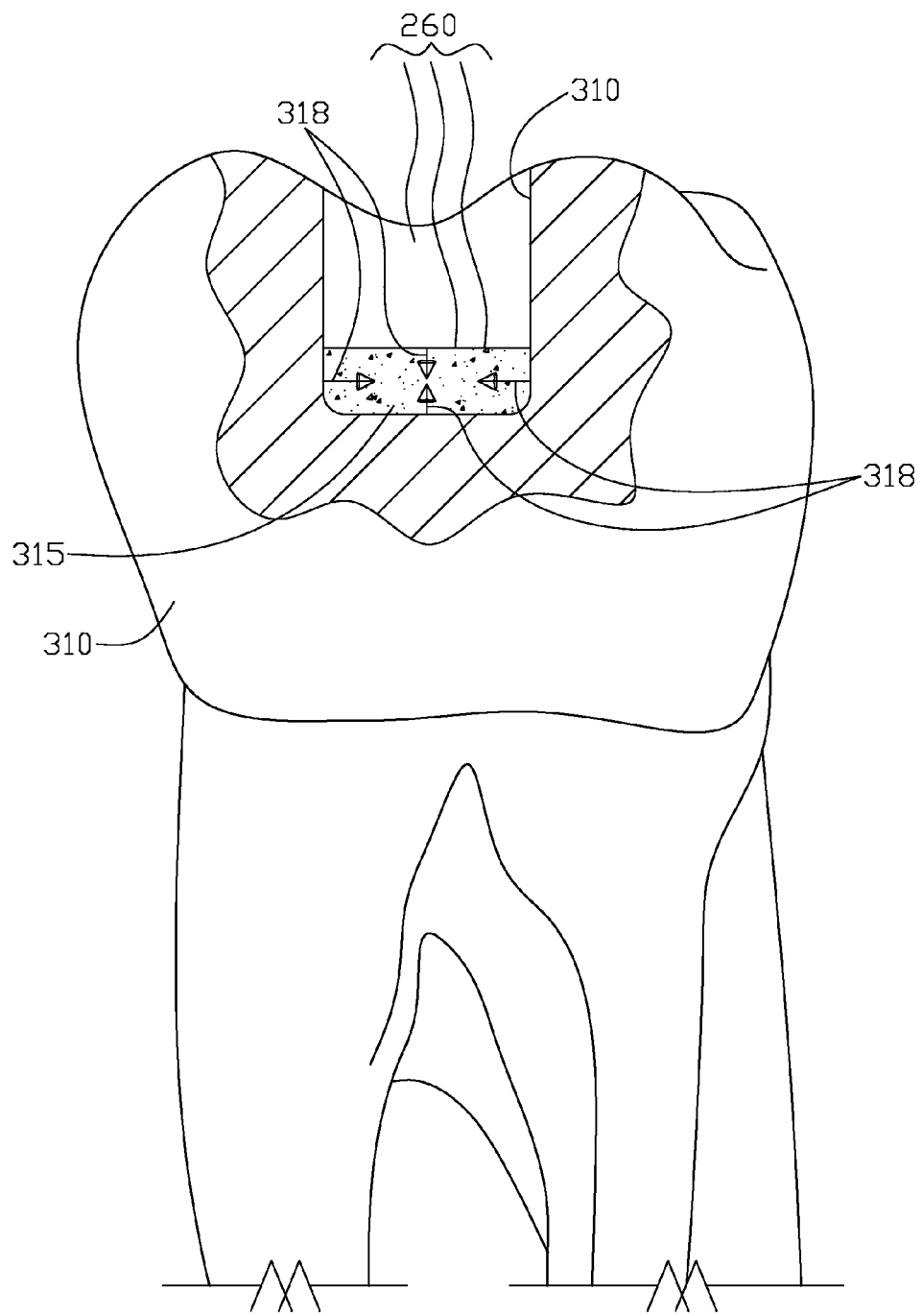
FIG. 35 shows an expanded tooth cross section with the prepared tooth cavity, being the prior art version with the composite filler material in a single layer without a tool tip present, the shrinkage movement of the composite filler material in the curing phase in going from a pliable non-hardened state to a hardened state via the prior art curing light transmission pathway.

Next, FIG. 35 shows an expanded tooth cross section with the prepared tooth cavity 310, being the prior art version with the composite filler material 315 in a single initial layer without a dental tool tip present, the shrinkage movement 318 of the composite filler material 315 in the curing phase is shown in going from a pliable non-hardened state through curing to a hardened state via the prior art curing light transmission pathway 260. Wherein the use of a typical prior art dental tool 390 that is constructed of stainless steel must be removed prior to the application of the curing light transmission 260 as the stainless steel dental tool 390 will block the curing light transmission 260 and interfere with the proper curing of the composite 315. Notably, prior to the application of the curing light transmission 260, the prior art stainless steel dental tool 390 is used to shape and form the composite 315 layer within the prepared tooth cavity 310 (as the composite 315 has a paste like viscosity), however, another significant issue is that the composite 315 being paste like sticks to the prior art stainless steel dental tool 390, causing problems as shown and described in FIG. 37.

Figure 36:
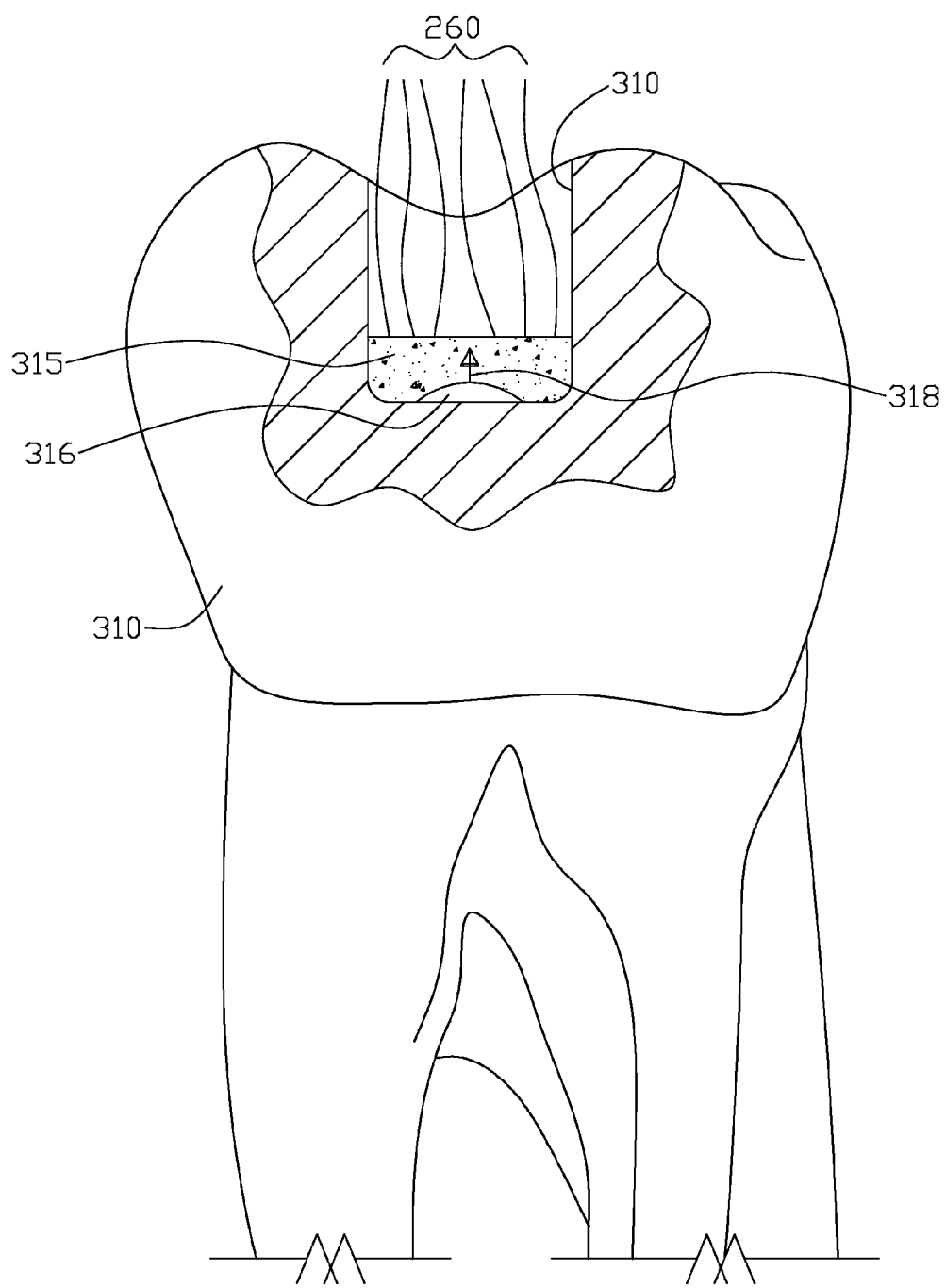
FIG. 36 shows an expanded tooth cross section with the prepared tooth cavity, being the prior art version with the composite filler material in a single layer without a tool tip present, the shrinkage movement of the composite filler material in the curing phase in going from a pliable non-hardened state to a hardened state via the prior art curing light transmission pathway, wherein the formation of an undesirable hidden void occurs from the composite filler material shrinkage.

The composite 315 shrinkage 318 in the art is about up to 3.0% assumed to be roughly omni-directionally by volume during the light transmission 260 curing phase in going from paste like and pliable 420 to hardened 425 to form a part of the parent tooth, thus as subsequently explained the use of force or pressure 365, 370 on the tool tip 105 as against the composite 315 during the composite 315 curing or hardening 420 to 425 process attempts to compensate for the shrinkage 318 thus minimizing the formation of voids 316 within the composite 315 during hardening or voids 316 or partial adhesion of the composite 315 to the prepared tooth 310. Continuing, FIG. 36 shows an expanded tooth cross section with the prepared tooth cavity 310, being the prior art version with the composite filler material 315 in a single initial layer without a dental tool tip present, the shrinkage movement 318 of the composite filler 315 material in the curing phase in going from a pliable non-hardened state 420 to a hardened state 425 via the prior art curing light transmission pathway 260, wherein the formation of an undesirable hidden void 316 occurs from the composite filler material 315 shrinkage 318. Wherein the void 316 that is shown in FIG. 36 can weaken the adherence of the composite 315 to the parent tooth material 310 plus weaken the structure of the composite 315 itself via having an air pocket void 316 that will allow the composite 316 to "flex" and possibly crack by not having a solid integral material cross section as between tooth 310 and composite 315.

Figure 37:
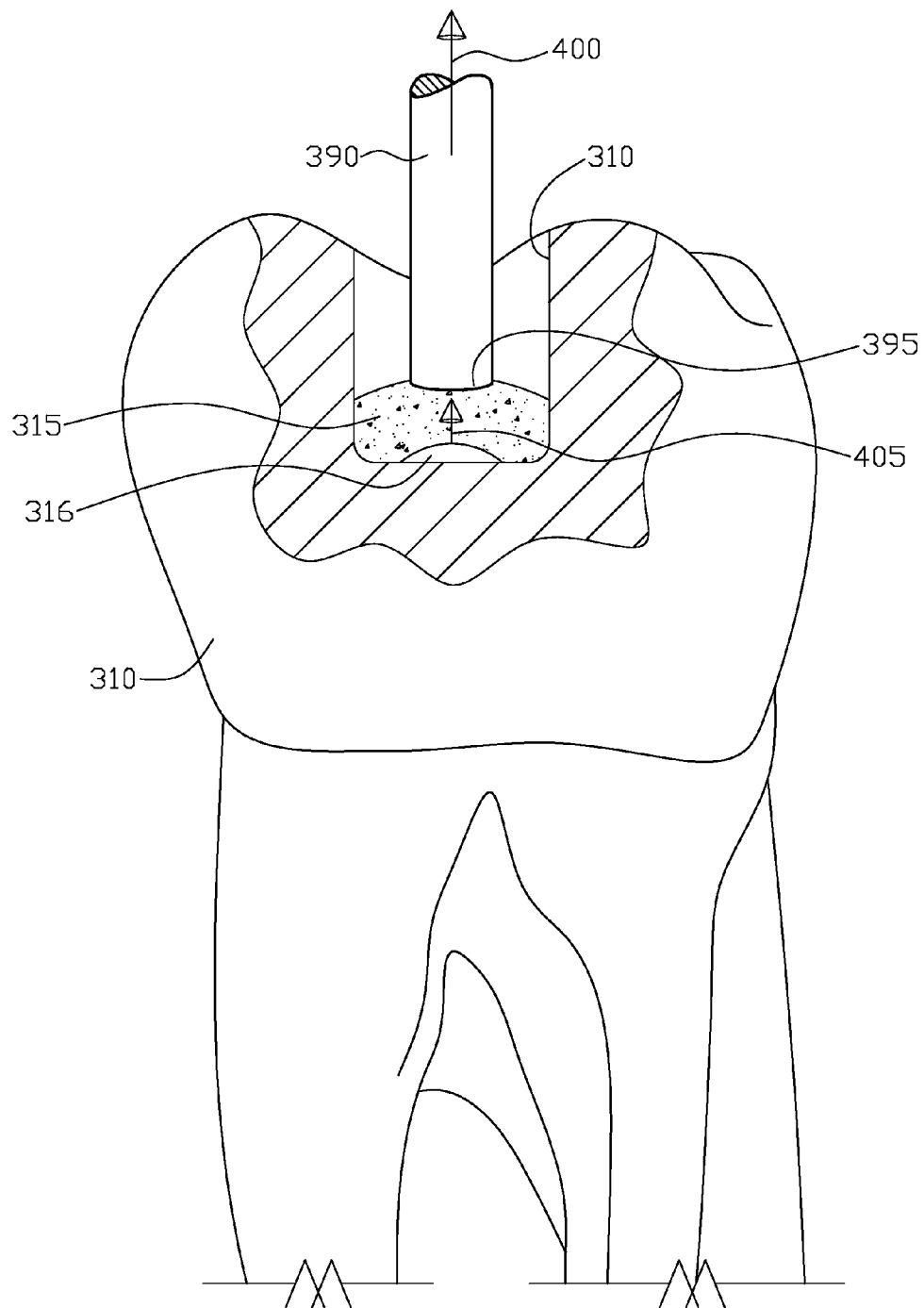
FIG. 37 shows an expanded tooth cross section with the prepared tooth cavity, being the prior art version with the composite filler material in a single layer with a conventional stainless steel tool tip present that is used to place the composite filler material, wherein an added method of formation of an undesirable hidden void occurs from the composite filler material sticking to the tool tip at an interface as between the stainless steel tool tip and the composite filler material due to the paste like stickiness of the composite filler material, this is termed "pull back" of the composite filler material with the tool tip, wherein to remedy this a no-stick wetting agent is placed at the interface to prevent sticking at the interface, however, the no-stick wetting agent can interfere with the bonding to the composite filler material to the prepared tooth cavity and to the subsequent layer of the composite filler material.

Continuing, FIG. 37 shows an expanded tooth cross section with the prepared tooth cavity 310, being the prior art version with the composite filler material 315 in a single initial layer with a conventional prior art dental tool 390 with a stainless steel tool tip 390 present that is used to place and position the composite filler material 315 within the prepared tooth cavity 310, usually in multiple layers of about 1.0 to 2.0 millimeters in thickness, wherein an added undesirable method of formation of an undesirable hidden void 316 occurs from the composite filler 315 material sticking to the tool tip 390 at an interface 395 as between the stainless steel tool tip 390 and the composite filler material 315 due to the paste like stickiness of the composite filler material 315 when it is in its pliable non-cured or non-hardened state 420. This undesirable problem is termed "pull back" being force direction 405 and 400 of the composite filler material 315 with the tool tip 390, i.e. when the tool tip 390 is being moved or removed from the prepared cavity 310—which can result in the composite 315 being cured or hardened to what is shown in FIG. 36 with all of the previously identified undesirable consequences.

This is why with the present invention tool tip 105 remaining in force full contact 365, 370 with the composite 315 during the curing and hardening 420 to 425 light transmission process 260 is important to minimize the chance of undesirable voids 316 forming in the composite 315 either from shrinkage 318 during the hardening process or forming a permanent void 318 in the hardened composite 315. Wherein to remedy this "pull back" situation with the use of a prior art dental tool constructed of stainless steel 390, a no-stick wetting agent (as is known in the art) is placed at the interface 395 to prevent the undesirable sticking as between the composite filler material 315 and the tool tip 390 at the interface 395, as is shown in FIG. 37. However, in addition the no-stick wetting agent can interfere with the desired dry bonding of the composite filler material 315 to the prepared tooth cavity 310 and to the subsequent layer of the composite filler material 315 thus undesirably weakening the integrity and strength of the composite 315 to composite 315 bond as between layers and the composite 315 to prepared tooth cavity 310 bond.

Figure 38:
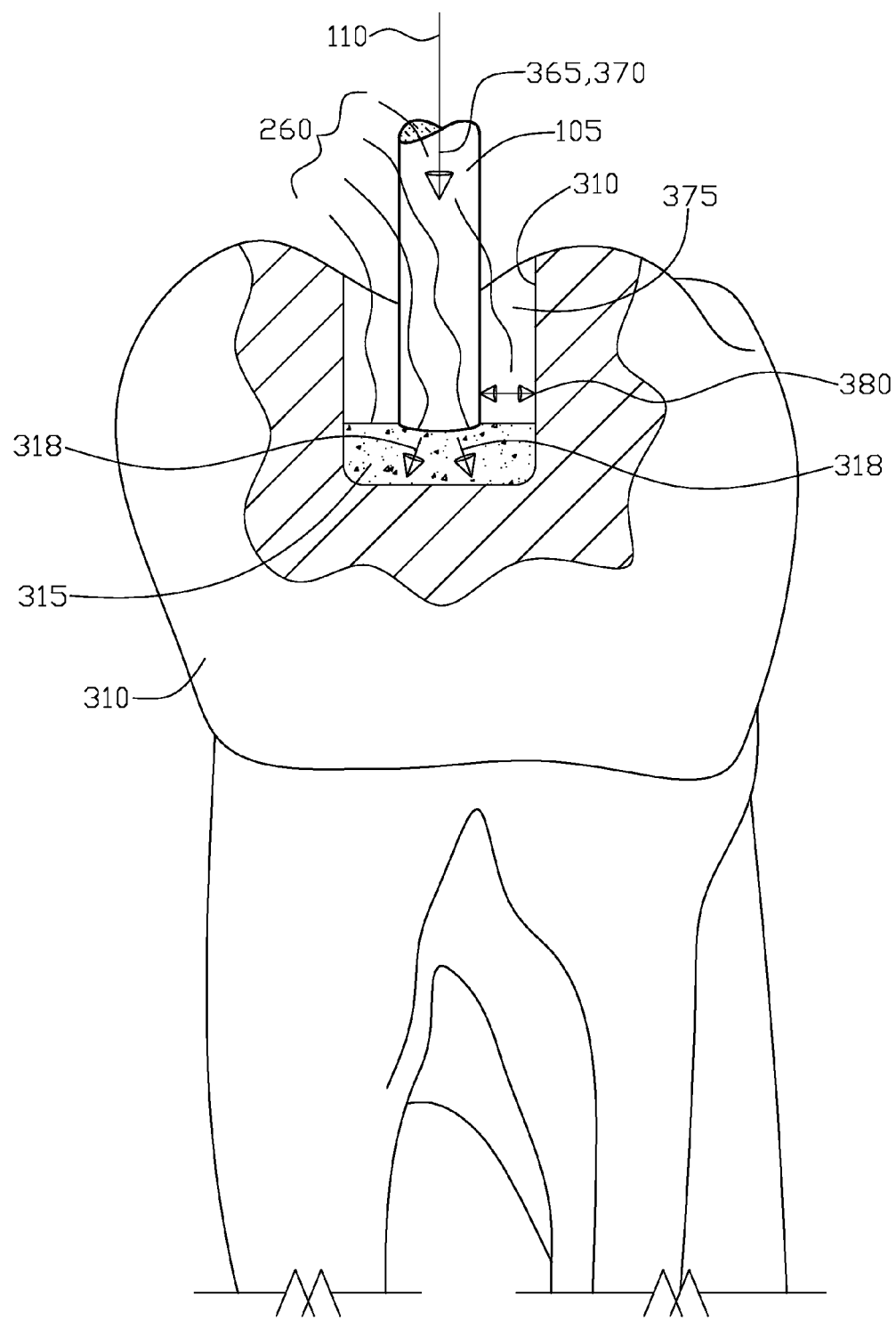
FIG. 38 shows an expanded tooth cross section with the prepared tooth cavity, with the composite filler material in a single layer with the present invention dental tool transparent tip present that is used to condense and compact the composite filler material layer, wherein the transparent tip maintains a selected amount of pressure upon the composite during the curing process to help compensate for composite shrinkage during the curing process from the light transmission to help prevent undesirable voids from forming as between the composite and the parent tooth material or within the composite material itself, as the tool tip is shown slightly depressed into the composite material from the selected amount of pressure with an added goal of minimizing a free area of the composite surface that is neither in contact with the parent tooth material or the tool tip such that the composite free area is uncontrolled during composite curing.

Further, FIG. 38 shows an expanded tooth cross section with the prepared tooth cavity 310, with the composite filler material 315 in a single initial layer with the present invention dental tool transparent tip 105 present that is used to condense and compact the composite filler material 315 layer. Wherein, as shown in FIG. 38 the transparent tip 105 maintains a selected amount of pressure 365, 370 upon the composite 315 during the curing process to help compensate for composite shrinkage 318 during the curing process from the light transmission 260 to help prevent undesirable voids 316 (not shown-however, previously discussed) from forming as between the composite 315 and the parent tooth material 310 or within the composite material 315 itself. In FIG. 38 the tool tip 105 is shown slightly depressed (however, not over depressed) into the composite material 315 from the selected amount of pressure identified as a specific force 365, 370 that is preferably from experimental testing in the range of about one-half (0.5) pounds force with an added goal of minimizing a free area 380 of the composite 315 surface that is neither in contact with the parent tooth material 310 or the tool tip 105 such that the composite free area 380 is uncontrolled during composite 315 curing 420 to 425 via being exposed to the atmosphere 375.

Thus, in FIG. 38 the use of the present invention tool tip 105 is in its correct form for the initial layer of composite filler material 315 via having continuous force/pressure 365, 370 upon the composite 315 from the tool tip 105 being simultaneous with the light transmission 260 curing process in taking the composite 315 from the uncured pliable non-hardened state 420 to the cured hardened state 425 to substantially reduce the occurrence of voids 316 (as shown in FIGS. 36 and 37). Noting also in FIG. 38 that the transparent tool tip 105 while immersed into the composite 315 does not stick to the composite 315 which can cause undesirable voids 316 as shown in FIG. 37 or require the undesirable use of a wetting agent at interface 395, wherein the wetting agent can contaminate and lessen the adherence of the composite 315 to the parent tooth material 310 or also contaminate and lessen the adherence of the composite 315 to its own subsequent layers.

Figure 39:
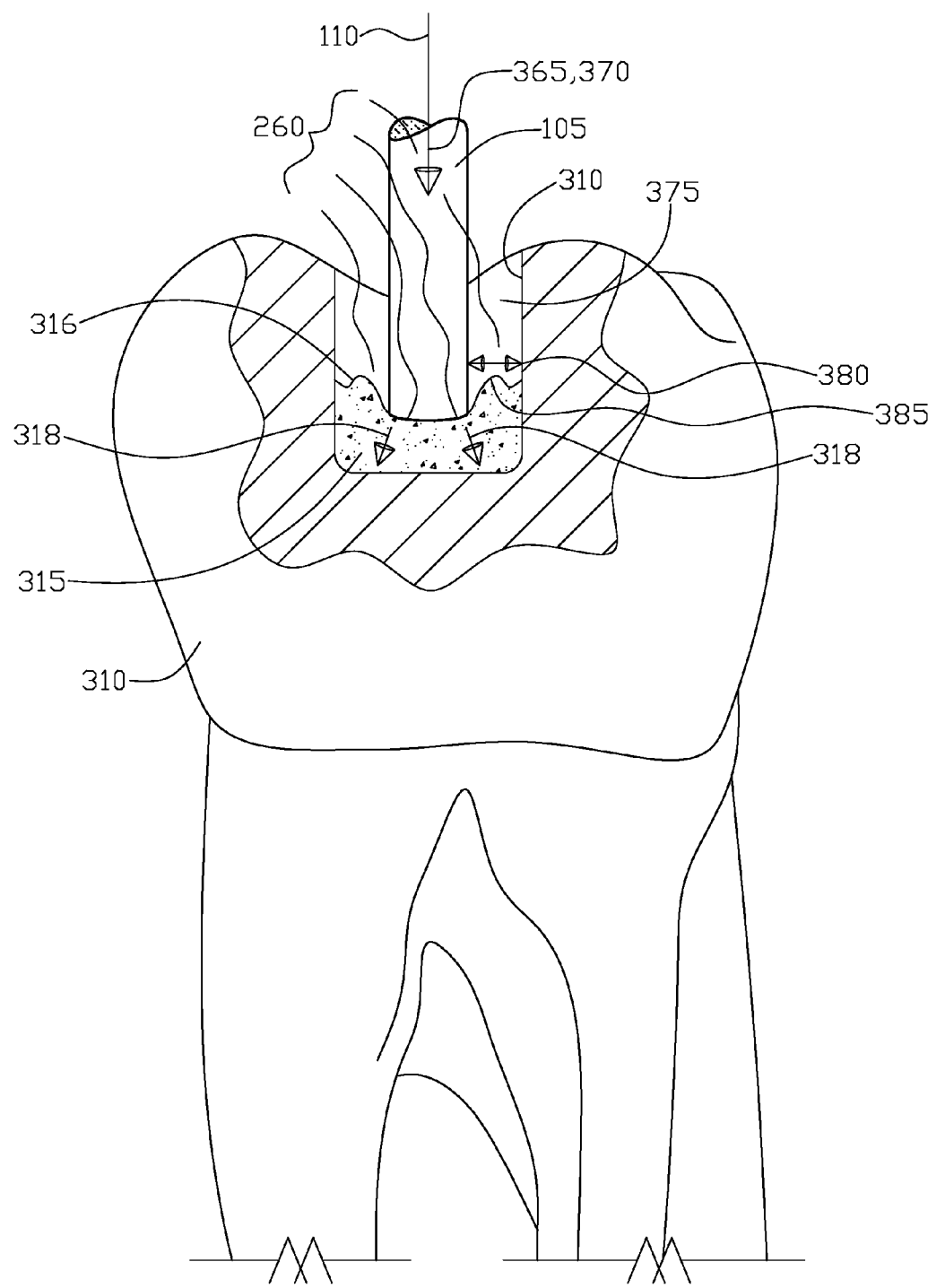
FIG. 39 shows an expanded tooth cross section with the prepared tooth cavity, with the composite filler material in a single layer with the present invention dental tool transparent tip present that is used to condense and compact the composite filler material layer, wherein what is shown is the transparent tip maintaining an excessive amount of pressure upon the composite during the curing process from the light transmission to help compensate for composite shrinkage during the curing process to help prevent undesirable voids from forming as between the composite and the parent tooth material or within the composite material itself, as the tool tip is shown significantly depressed into the composite material wherein the free area of the composite surface is flowing uncontrollably upward an excessive amount that is neither in contact with the parent tooth material or the tool tip such that the composite free area is uncontrolled during composite curing resulting in a higher probability of forming undesirable voids and an uneven surface at the flowing area that will be more difficult to integrate with subsequent layers on composite or to finish smooth with the tooth top contour.

Continuing, FIG. 39 shows an expanded tooth cross section with the prepared tooth cavity 310, with the composite filler material 315 in a single initial layer with the present invention dental tool transparent tip 105 present that is used to condense and compact the composite filler material 315 layer, wherein what is shown is the transparent tip 105 maintaining an excessive amount of pressure or force 365, 370 being greater than the preferred value of about one-half (0.5) pounds force placed upon the composite 315 during the curing process from the light transmission 260 to help compensate for composite 315 shrinkage 318 during the curing process to help prevent undesirable voids 316 from forming as between the composite 315 and the parent tooth material 310 or within the composite material itself 315.

In FIG. 39, the tool tip 105 is shown significantly depressed into the composite material 315 wherein the free area 380 of the composite 315 surface is flowing uncontrollably 385 upward an excessive amount that is neither in contact with the parent tooth material 310 or the tool tip 105. Such that as shown in FIG. 39 the composite free area 380 is uncontrolled during composite 315 curing resulting in a higher probability of forming undesirable voids 316 and an uneven surface 385 at the flowing free surface area 380 being totally exposed to the atmosphere 380 that will be more difficult to integrate with subsequent layers of composite 315 as this uneven surface 385 takes a permanent form after curing in being hardened 425 moving away from desirable homogeneous (or void 316 free) structure of multiple layers of composite 315.

Therefore the amount of force or pressure 365, 370 is somewhat of an art to determine, as too little force or pressure 365, 370 could result in voids 316 forming in the composite 315 as FIG. 36 would indicate with zero force or pressure 365, 370, and in an opposing manner excessive force or pressure 365, 370 will result in what is shown in FIG. 39 with the attendant problems previously identified. From testing it was shown that by minimizing the uncontrolled area 380, the negative effects from excessive pressure or force 365, 370 are lessened with less uneven surface 385 and less voids adjacent to the uneven surface 385, as the goal of the present invention composite 315 layers process is to apply pressure or force 365, 370 to compensate for composite 315 shrinkage 318 during the curing or hardening process of the composite 315 in order to minimize the permanent formation of voids 316 in the hardened and cured 425 composite 315.

Figure 40:
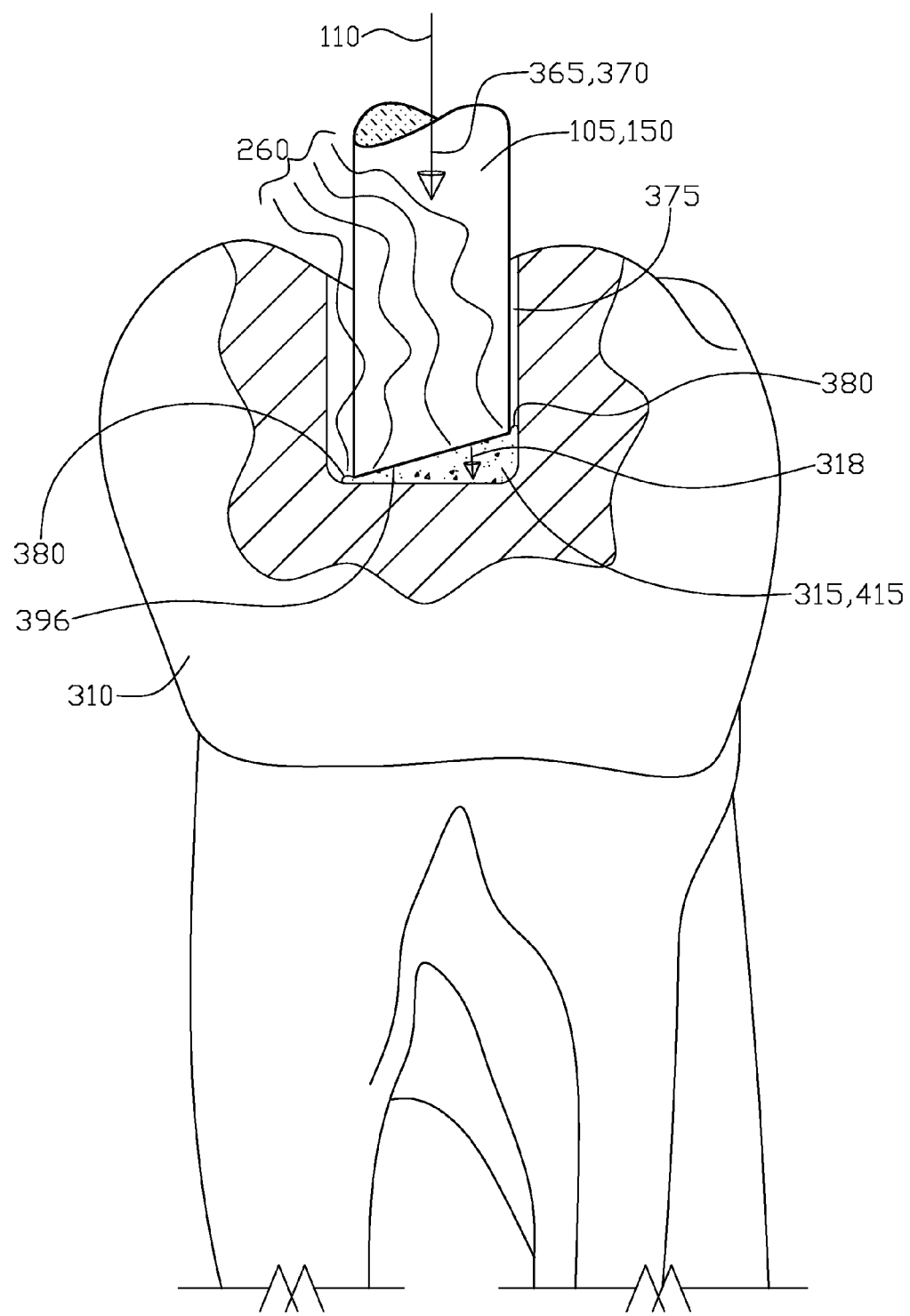
FIG. 40 shows an expanded tooth cross section with the prepared tooth cavity, with the composite filler material in a selected wedge shaped configuration initial single layer with the present invention dental tool transparent tip that is also in a wedge shaped configuration that is used to condense and compact the wedge shaped composite filler material layer, wherein the transparent tip maintains a selected amount of pressure upon the composite during the curing process from the light transmission to help compensate for composite shrinkage during the curing process to help prevent undesirable voids from forming as between the composite and the parent tooth material or within the composite material itself, as the tool tip is shown slightly depressed into the composite material with an added goal of minimizing a free area of the composite surface that is neither in contact with the parent tooth material or the tool tip such that the composite free area is uncontrolled during composite curing.

Next, FIG. 40 shows an expanded tooth cross section with the prepared tooth cavity 310, with the composite filler material 315 in a selected wedge shaped configuration initial single layer 415 with the present invention dental tool transparent tip 105 that is also in a selected wedge shaped configuration 150 that is used to condense and compact the wedge shaped composite filler initial material layer 415. Wherein in FIG. 40, the transparent tip 150 maintains a selected amount of pressure 365, 370 as previously indicated upon the composite 315 during the curing process from the light transmission 260 to help compensate for composite 315 shrinkage 318 during the curing process to help prevent undesirable voids 316 from forming as between the composite 315 and the parent tooth material 310 or within the composite material 315 itself, as part of an interlocking "jigsaw" of subsequent composite 315 layers 415, 416, 417, and 418 shown in FIGS. 41, 42, and 43.

As the tool tip 150 in FIG. 40 is shown slightly depressed into the composite material 315 with an added goal of minimizing a free area 380 of the composite 315 surface that is neither in contact with the parent tooth material 310 or the tool tip 150 such that the composite free area 380 is minimized as it is uncontrolled during composite 315 curing as being exposed to the atmosphere 375. Thus FIGS. 40, 41, 42, and 43 show that with selected custom tool tips 105 utilizing transparent material, any number of special composite 315 layering configurations can be facilitated as the custom tool tips 105 make for much more control of the pliable forming and hardening of the composite 315 via condensing and compacting the composite 315 with the tool tip 105, with the decision on which of numerous disclosed or equivalent selected tool tip 105 exposed 107 specific geometry types is chosen by the dental practitioner 320 based upon the configuration of the prepared dental tooth cavity 310.

Figure 41:
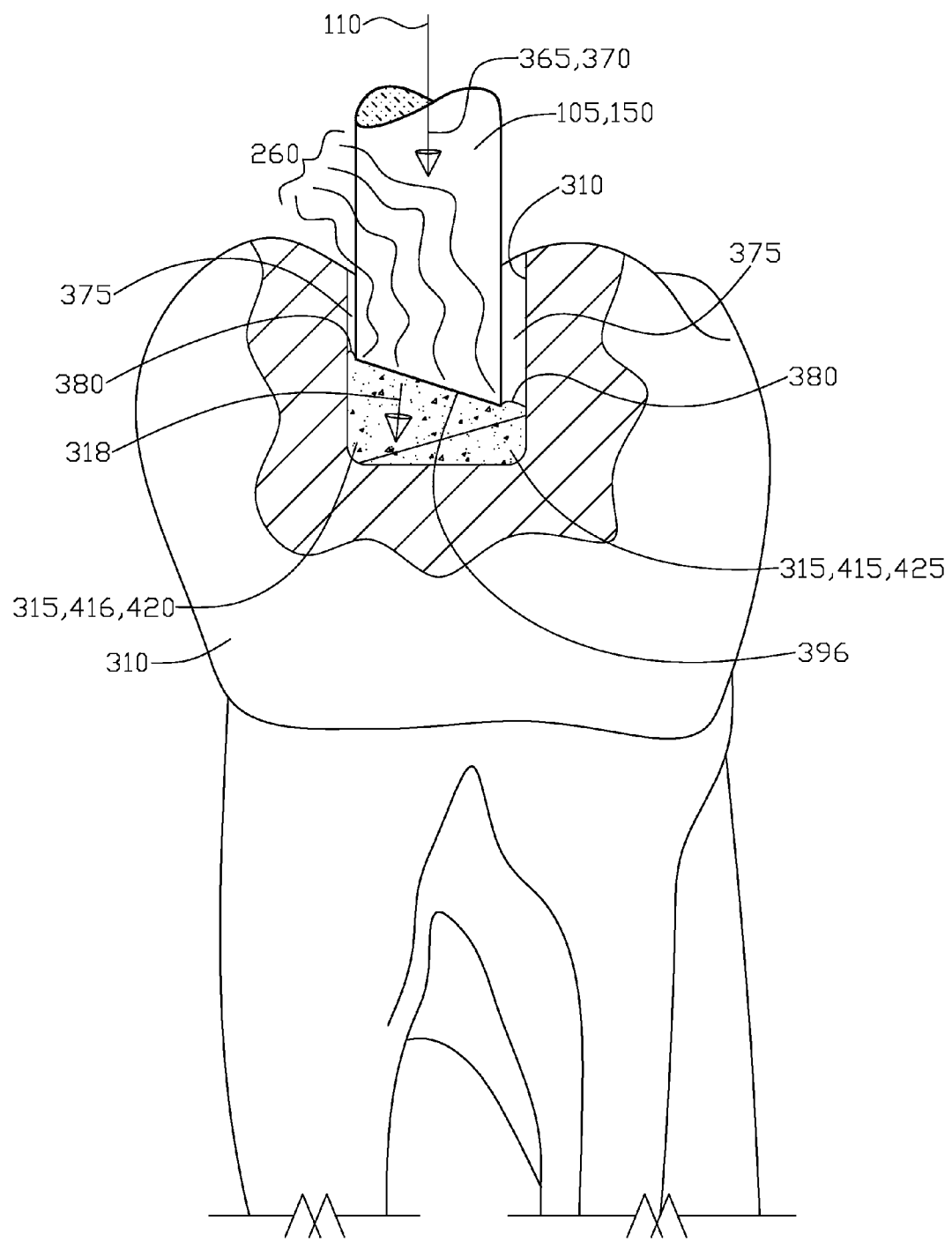
FIG. 41 shows an expanded tooth cross section with the prepared tooth cavity, with a second composite filler material layer in a selected wedge shaped configuration layer added to the initial wedge shaped layer in FIG. 40, with the present invention dental tool transparent tip that is also in a wedge shaped configuration that is used to condense and compact the second wedge shaped composite filler material layer, wherein the transparent tip maintains a selected amount of pressure upon the second wedge shaped composite layer during the curing process from the light transmission to help compensate for composite shrinkage in the second layer during the curing process to help prevent undesirable voids from forming as between the composite and the parent tooth material or within the composite material itself, as the tool tip is shown slightly depressed into the second composite material layer with an added goal of minimizing a free area of the composite surface that is neither in contact with the parent tooth material or the tool tip such that the composite free area is uncontrolled during composite curing.

Further, FIG. 41 shows an expanded tooth cross section with the prepared tooth cavity 310, being a continuation of FIG. 40 for the subsequent composite 315 layering, with a second composite filler material 315 layer in a selected wedge shaped configuration layer 416 added to the initial already cured and hardened 425 wedge shaped layer 415 in FIG. 40. Thus in FIG. 41, with the present invention dental tool transparent tip 105 that is also in a wedge shaped configuration 150 is used to condense and compact the second wedge shaped composite filler material layer 416, wherein the transparent tip 150 maintains a selected amount of pressure 365, 370 as previously described upon the second wedge shaped composite layer 416 during the curing process from the light transmission 260 to help compensate for composite shrinkage 318 in the second layer 416 during the curing process to help prevent undesirable voids 316 from forming as between the composite 315 and the parent tooth material 310 or within the composite material 315 itself. As the tool tip 150 in FIG. 41 is shown slightly depressed into the second composite material layer 416 with an added goal of minimizing a free area 380 of the composite 315 surface that is neither in contact with the parent tooth material 310 or the tool tip 150 such that the composite free area 380 is uncontrolled during composite 315 curing.

Figure 42:
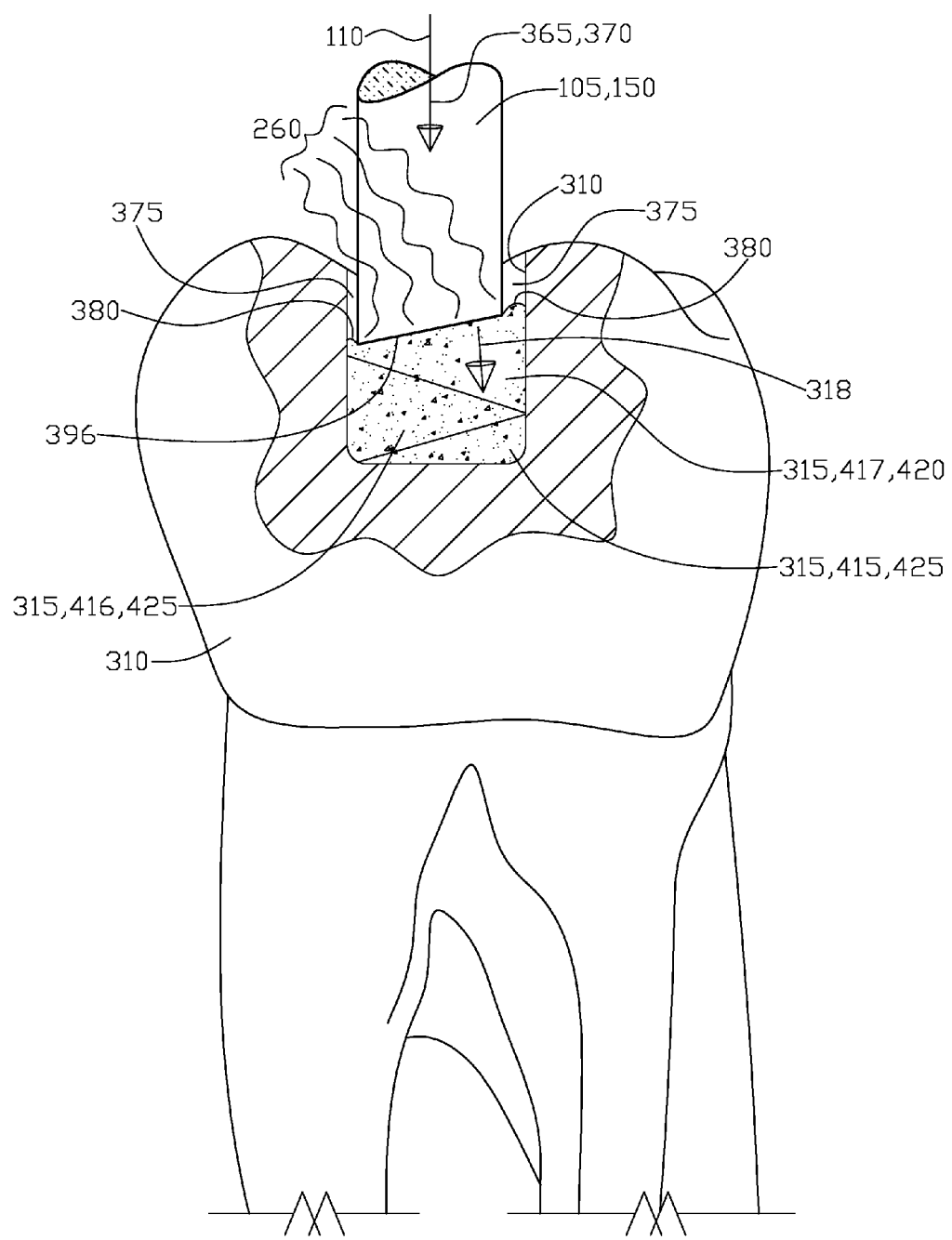
FIG. 42 shows an expanded tooth cross section with the prepared tooth cavity, with a third composite filler material layer in a selected wedge shaped configuration layer added to the initial wedge shaped layer in FIG. 40, and the second wedge shaped layer in FIG. 41, with the present invention dental tool transparent tip that is also in a wedge shaped configuration that is used to condense and compact the third wedge shaped composite filler material layer, wherein the transparent tip maintains a selected amount of pressure upon the third wedge shaped composite layer during the curing process from the light transmission to help compensate for composite shrinkage in the third layer during the curing process to help prevent undesirable voids from forming as between the composite and the parent tooth material or within the composite material itself, as the tool tip is shown slightly depressed into the third composite material layer with an added goal of minimizing a free area of the composite surface that is neither in contact with the parent tooth material or the tool tip such that the composite free area is uncontrolled during composite curing.

Continuing, FIG. 42 shows an expanded tooth cross section with the prepared tooth cavity 310, being a continuation of FIG. 41 for the subsequent composite 315 layering with a third composite filler material layer in a selected wedge shaped configuration layer 417 added to the cured and hardened 425 second wedge shaped composite layer 416 in FIG. 41 and the cured and hardened 425 initial wedge shaped layer 415 in FIG. 41, with the present invention dental tool transparent tip 105 that is also in a wedge shaped configuration 150 that is used to condense and compact the third wedge shaped composite filler material layer 417. Wherein in FIG. 42 the transparent tip 150 maintains a selected amount of pressure 365, 370 as previously described upon the third wedge shaped composite layer 417 during the curing process from the light transmission 260 to help compensate for composite shrinkage 318 in the third layer 417 during the curing process to help prevent undesirable voids 316 from forming as between the composite 315 and the parent tooth material 310 or within the composite material 315 itself. As the tool tip 150 in FIG. 42 is shown slightly depressed into the third composite material layer 417 with an added goal of minimizing a free area 380 of the composite 315 surface that is neither in contact with the parent tooth material 310 or the tool tip 150 such that the composite free area 380 is uncontrolled during composite curing via exposure to the atmosphere 375.

Figure 43:
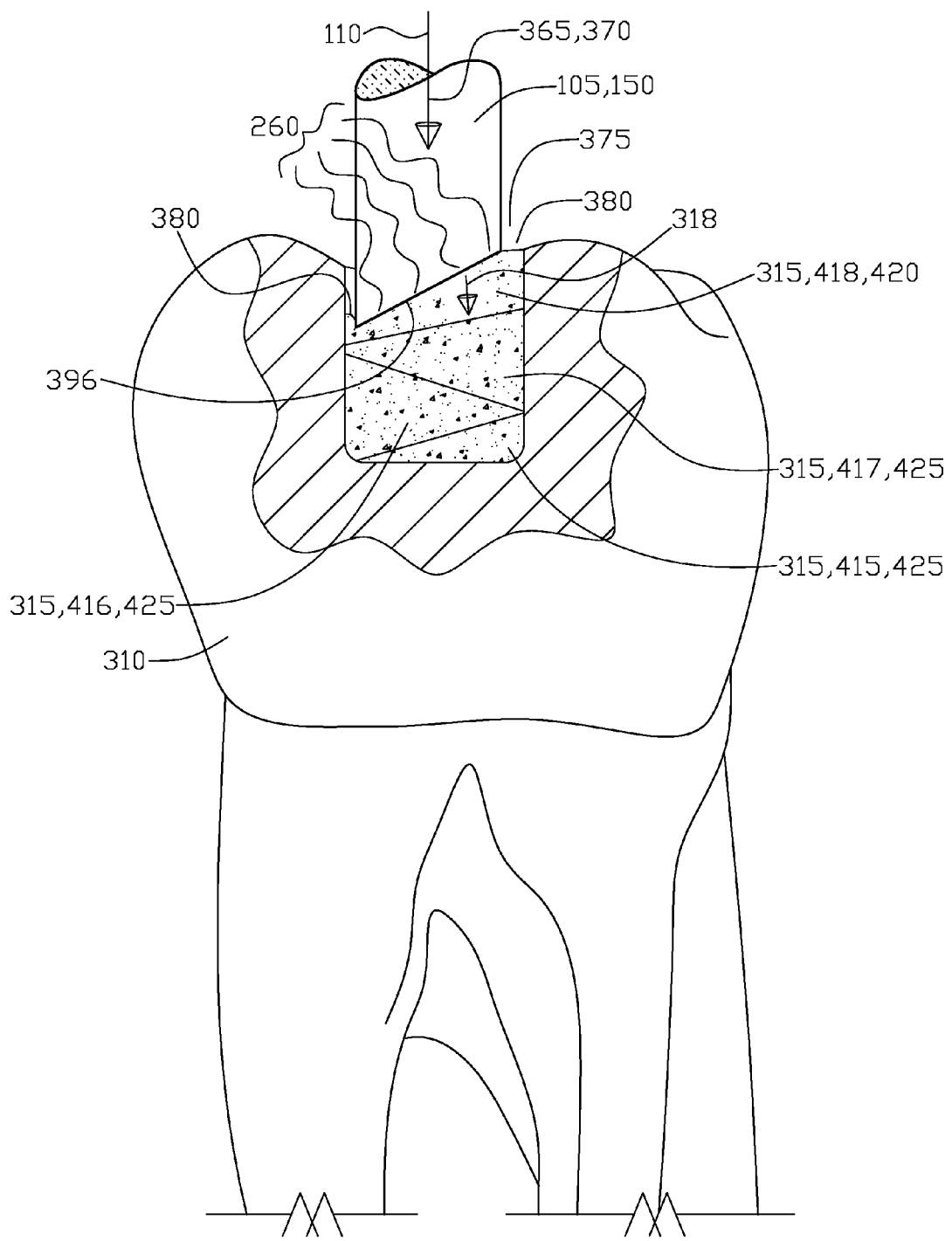
FIG. 43 shows an expanded tooth cross section with the prepared tooth cavity, with a fourth composite filler material layer in a selected wedge shaped configuration layer added to the third wedge shaped layer in FIG. 42, and the second wedge shaped layer in FIG. 41, with the present invention dental tool transparent tip that is also in a wedge shaped configuration that is used to condense and compact the fourth wedge shaped composite filler material layer, wherein the transparent tip maintains a selected amount of pressure upon the fourth wedge shaped composite layer during the curing process from the light transmission to help compensate for composite shrinkage in the fourth layer during the curing process to help prevent undesirable voids from forming as between the composite and the parent tooth material or within the composite material itself, as the tool tip is shown slightly depressed into the fourth composite material layer with an added goal of minimizing a free area of the composite surface that is neither in contact with the parent tooth material or the tool tip such that the composite free area is uncontrolled during composite curing, thus with FIGS. 40, 41, 42, and 43 forming a wedged interlocking composite layers system for tooth cavity filling.

Moving onward, FIG. 43 shows an expanded tooth cross section with the prepared tooth cavity 310, being a continuation of FIG. 42 for the subsequent composite 315 layering, with a fourth composite filler material layer in a selected wedge shaped configuration layer 418 added to the cured and hardened 425 third wedge shaped layer 417 in FIG. 42, and the second wedge shaped layer 416 in FIG. 41. In FIG. 43 shown is the present invention dental tool transparent tip 105 that is also in a wedge shaped configuration 150 that is used to condense and compact the fourth wedge shaped composite filler material layer 418. Wherein the transparent tip 150 in FIG. 43 maintains a selected amount of pressure 365, 370 as previously described upon the fourth wedge shaped composite layer 418 during the curing process from the light transmission 260 to help compensate for composite shrinkage 318 in the fourth layer 418 during the curing process to help prevent undesirable voids 316 from forming as between the composite 315 and the parent tooth material 310 or within the composite material 315 itself. As shown in FIG. 43, the tool tip is 150 shown slightly depressed into the fourth composite material layer 418 with an added goal of minimizing a free area 380 of the composite 315 surface that is neither in contact with the parent tooth material 310 or the tool tip 150 such that the composite free area 380 is uncontrolled during composite curing via being exposed to the atmosphere 375.

Figure 44:
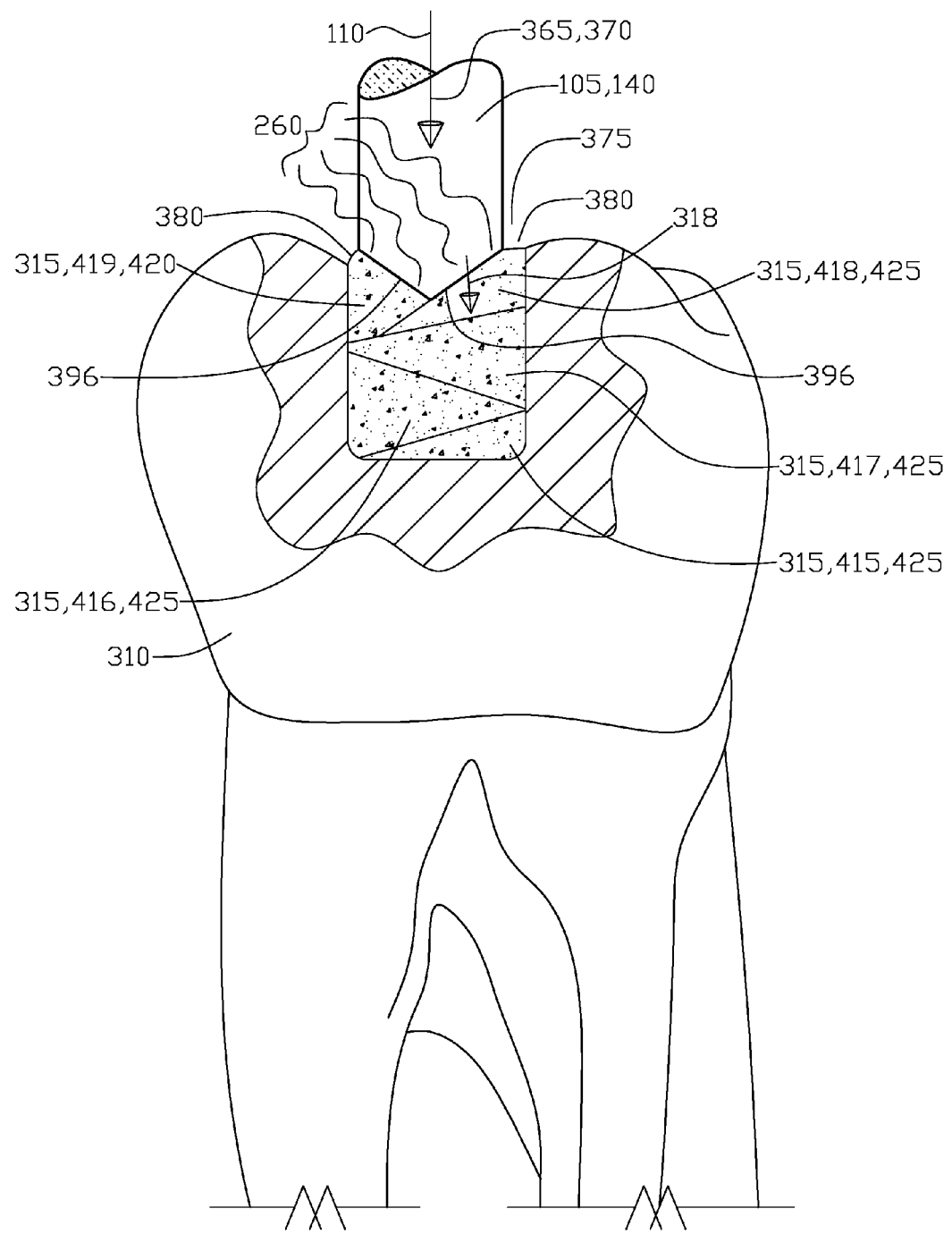
FIG. 44 shows an expanded tooth cross section with the prepared tooth cavity, with a fifth composite filler material layer in a selected wedge shaped configuration using a chisel shaped tip, with the fifth composite layer added to the fourth wedge shaped layer in FIG. 43 that is added to the third wedge shaped layer in FIG. 42, and the second wedge shaped layer in FIG. 41, that was added to the initial layer in FIG. 40 with the present invention dental tool transparent tip that is in a chisel shaped configuration that is used to condense and compact the fifth wedge shaped composite filler material layer, wherein the transparent tip maintains a selected amount of pressure upon the fifth wedge shaped composite layer during the curing process from the light transmission to help compensate for composite shrinkage in the fifth layer during the curing process to help prevent undesirable voids from forming as between the composite and the parent tooth material or within the composite material itself, as the tool tip is shown slightly depressed into the fifth composite material layer with an added goal of minimizing a free area of the composite surface that is neither in contact with the parent tooth material or the tool tip such that the composite free area is uncontrolled during composite curing, thus with FIGS. 40, 41, 42, 43, and 44 forming a wedged interlocking composite layers system for tooth cavity filing.

Further, FIG. 44 shows an expanded tooth cross section with the prepared tooth cavity 310, being a continuation of FIG. 43 for the subsequent composite 315 layering, with a fifth composite filler material 315 forming a wedge shaped fifth layer 419 using a chisel shaped 140 dental tool transparent tip 105 that is added to the fourth composite filler material layer in a selected wedge shaped configuration layer 418 added to the cured and hardened 425 third wedge shaped layer 417 in FIG. 42, and the second wedge shaped layer 416 in FIG. 41. In FIG. 44 shown is the present invention dental tool transparent tip 105 that is also in a chisel shaped configuration 140 that is used to condense and compact the fifth wedge shaped composite filler material layer 419. Wherein the transparent tip 150 in FIG. 44 maintains a selected amount of pressure 365, 370 as previously described upon the fifth wedge shaped composite layer 419 during the curing process from the light transmission 260 to help compensate for composite shrinkage 318 in the fifth layer 419 during the curing process to help prevent undesirable voids 316 from forming as between the composite 315 and the parent tooth material 310 or within the composite material 315 itself. As shown in FIG. 44, the tool tip is 140 shown slightly depressed into the fifth composite material layer 419 with an added goal of minimizing a free area 380 of the composite 315 surface that is neither in contact with the parent tooth material 310 or the tool tip 150 such that the composite free area 380 is uncontrolled during composite curing via being exposed to the atmosphere 375.

Thus with FIGS. 40, 41, 42, 43, and 44 shown is a higher strength wedged interlocking composite 315 layers system for tooth cavity 310 filling process. As the use of the tool tip 105 wedge shape 150 and final fifth later 419 chisel shaped tip 140 or any other tip configuration can facilitate a layer by layer buildup on composite 315, wherein the composite 315 layers are hardened in a subsequent manner having a much reduced chance of undesirable voids 316 forming, wherein some of the problems with voids 316 are but not limited to; voids 316 can cause weaker composite 315 layer to composite 315 layer adhesion and weaker composite 315 to prepared tooth 310 adhesion depending upon the location of the void 316, voids 316 also can be bacteria formation pockets—that can lead to advanced additional tooth decay, voids 316 can cause hot and cold sensitivity for the tooth 310, also voids 316 can structurally weaken the composite 315 filling itself-potentially leading to breaking to the composite 315 filling from the tooth 310 biting down on something hard.

The tool tip 105 of the present invention is somewhat embedded into the non-hardened or uncured composite 315 adding pressure 365, 370 during the curing process to the composite 315 to compensate for composite 315 shrinkage 318 during the curing process via allowing light transmission 260 for curing to harden there-through. With the tool tip 105 is to not only minimize undesirable voids 316 but to control the final form that the composite 315 takes while hardening, via minimizing the undesirable free area 380 which represents the uncontrolled composite 315 area which can end up with an undesirable shape (for integration with a subsequent composite 315 layer) or causing added grinding and polishing for the final composite 315 layer to blend in with the parent tooth material 310, or undesirable added voids 316. Note that once the composite free area 380 is at the fifth layer 419 after curing it will be ground and polished to match the parent tooth material 310 contour on the tooth 310 biting surface opposite of the tooth 310 root structure to complete the tooth 310 cavity filling.

Figure 45:
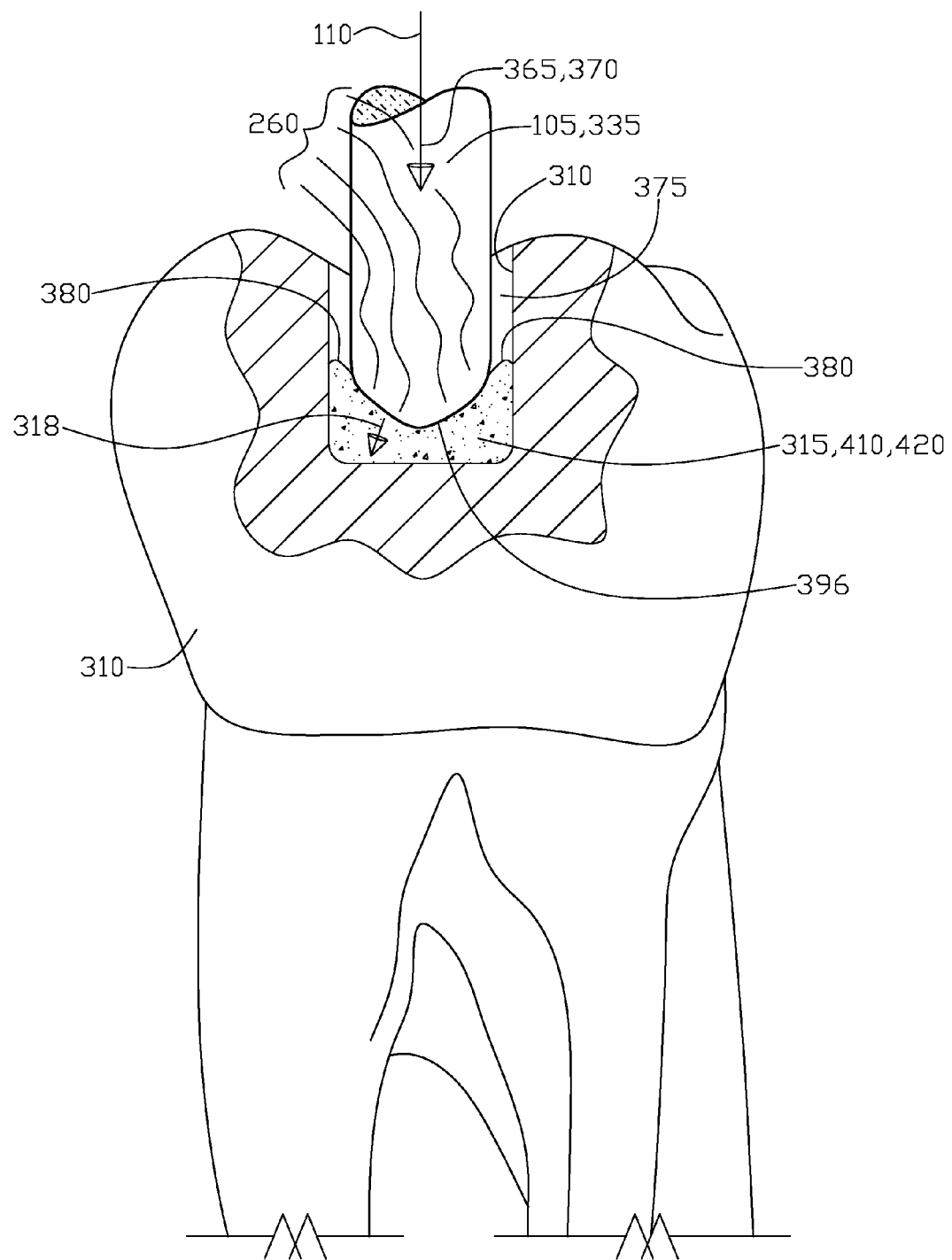
FIG. 45 shows an expanded tooth cross section with the prepared tooth cavity, with the initial layer composite filler material in a selected conical shaped configuration with the present invention dental tool transparent tip that is also in a conical shaped configuration that is used to condense and compact the conical shaped composite filler material layer, wherein the transparent tip maintains a selected amount of pressure upon the composite during the curing process from the light transmission to help compensate for composite shrinkage during the curing process to help prevent undesirable voids from forming as between the composite and the parent tooth material or within the composite material itself, as the tool tip is shown slightly depressed into the composite material with an added goal of minimizing a free area of the composite surface that is neither in contact with the parent tooth material or the tool tip such that the composite free area is uncontrolled during composite curing.

Continuing, FIG. 45 shows an expanded tooth cross section with the prepared tooth cavity 310, with the initial layer composite filler material 315 in a selected conical shaped configuration 410 with the present invention dental tool transparent tip 105 that is also in a conical shaped configuration 335 that is used to condense and compact the conical shaped initial composite filler material layer 410. Wherein the transparent tip 335 maintains a selected amount of pressure 365, 370 as previously described, that is upon the composite 410 during the curing process from the light transmission 260 to help compensate for composite shrinkage 318 during the curing process to help prevent undesirable voids 316 from forming as between the composite 315 and the parent tooth material 310 or within the composite material 315 itself. As is shown in FIG. 45 the tool tip 335 is shown slightly depressed into the composite material 315 with an added goal of minimizing a free area 380 of the composite 315 surface that is neither in contact with the parent tooth material 310 or the tool tip 335 such that the composite free area 380 is uncontrolled during composite curing via exposure to the atmosphere 375.

Figure 46:
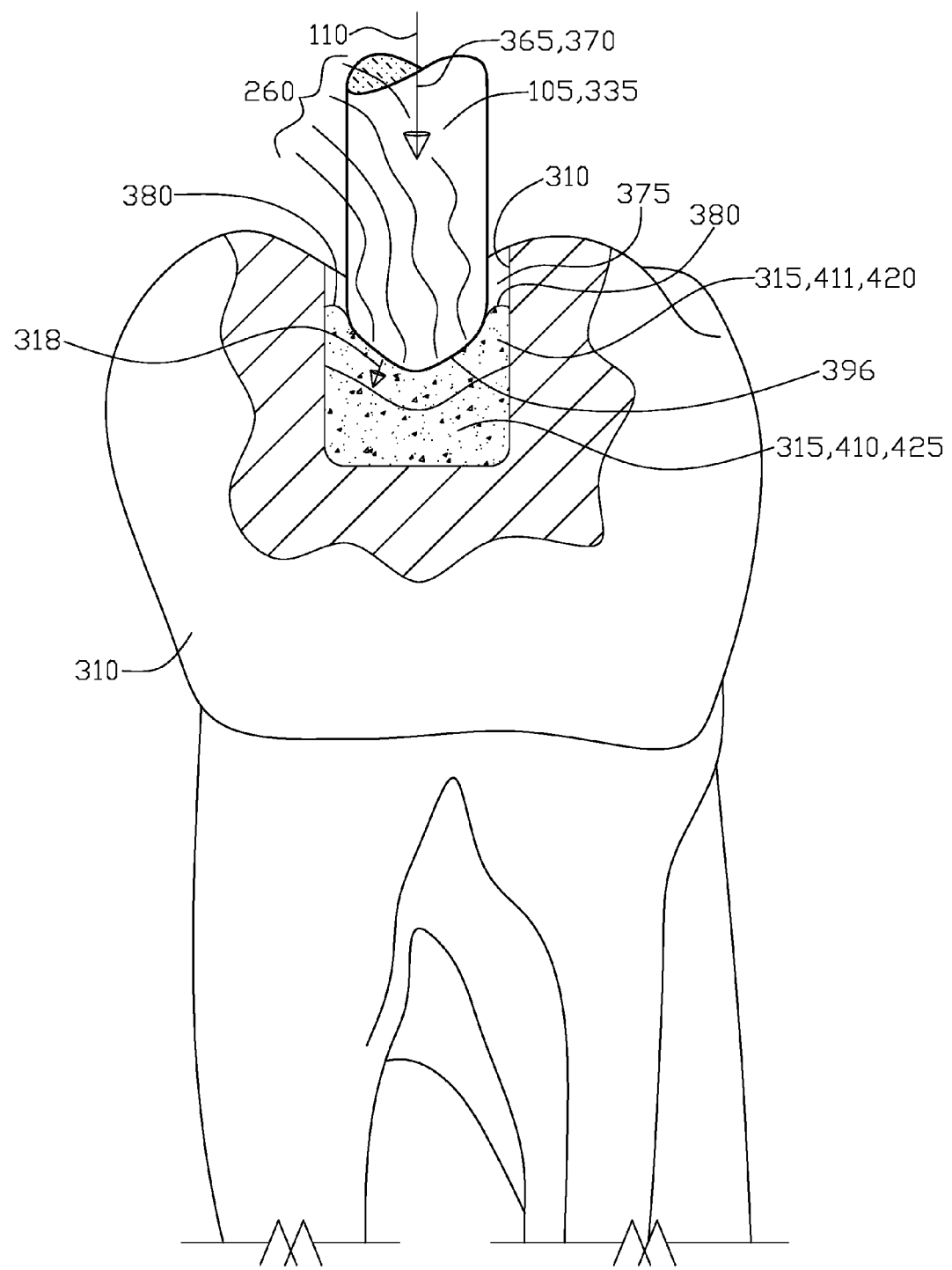
FIG. 46 shows an expanded tooth cross section with the prepared tooth cavity, with the second layer composite filler material in a selected conical shaped configuration with the present invention dental tool transparent tip that is also in a conical shaped configuration that is used to condense and compact the second conical shaped composite filler material layer, wherein the transparent tip maintains a selected amount of pressure upon the composite during the curing process from the light transmission to help compensate for composite shrinkage during the curing process to help prevent undesirable voids from forming as between the composite and the parent tooth material or within the composite material itself, as the tool tip is shown slightly depressed into the composite material with an added goal of minimizing a free area of the composite surface that is neither in contact with the parent tooth material or the tool tip such that the composite free area is uncontrolled during composite curing.

Next, FIG. 46 shows an expanded tooth cross section with the prepared tooth cavity 310, being a continuation of FIG. 45 for the subsequent composite 315 layering, as the initial selected conical composite layer 410 is already cured or hardened 425 with the un-hardened 420 second layer composite filler material in a conical shaped configuration 411 using the present invention dental tool transparent tip 105 that is also in a conical shaped configuration 335 that is used to condense and compact the second conical shaped composite filler material layer 411 during curing or hardening of the composite 315. Wherein in FIG. 46, the transparent tip 335 maintains a selected amount of pressure 365, 370 as previously described upon the composite 315 during the curing process from the light transmission 260 to help compensate for composite shrinkage 318 during the curing process to help prevent undesirable voids 316 from forming as between the composite 315 and the parent tooth material 310 or within the composite material 315 itself. As the tool tip 335 is shown slightly depressed into the composite material 315 with an added goal of minimizing a free area 380 of the composite 315 surface that is neither in contact with the parent tooth material 310 or the tool tip 335 such that the composite free area 380 is uncontrolled during composite 315 curing by being exposed to the atmosphere 375.

Figure 47:
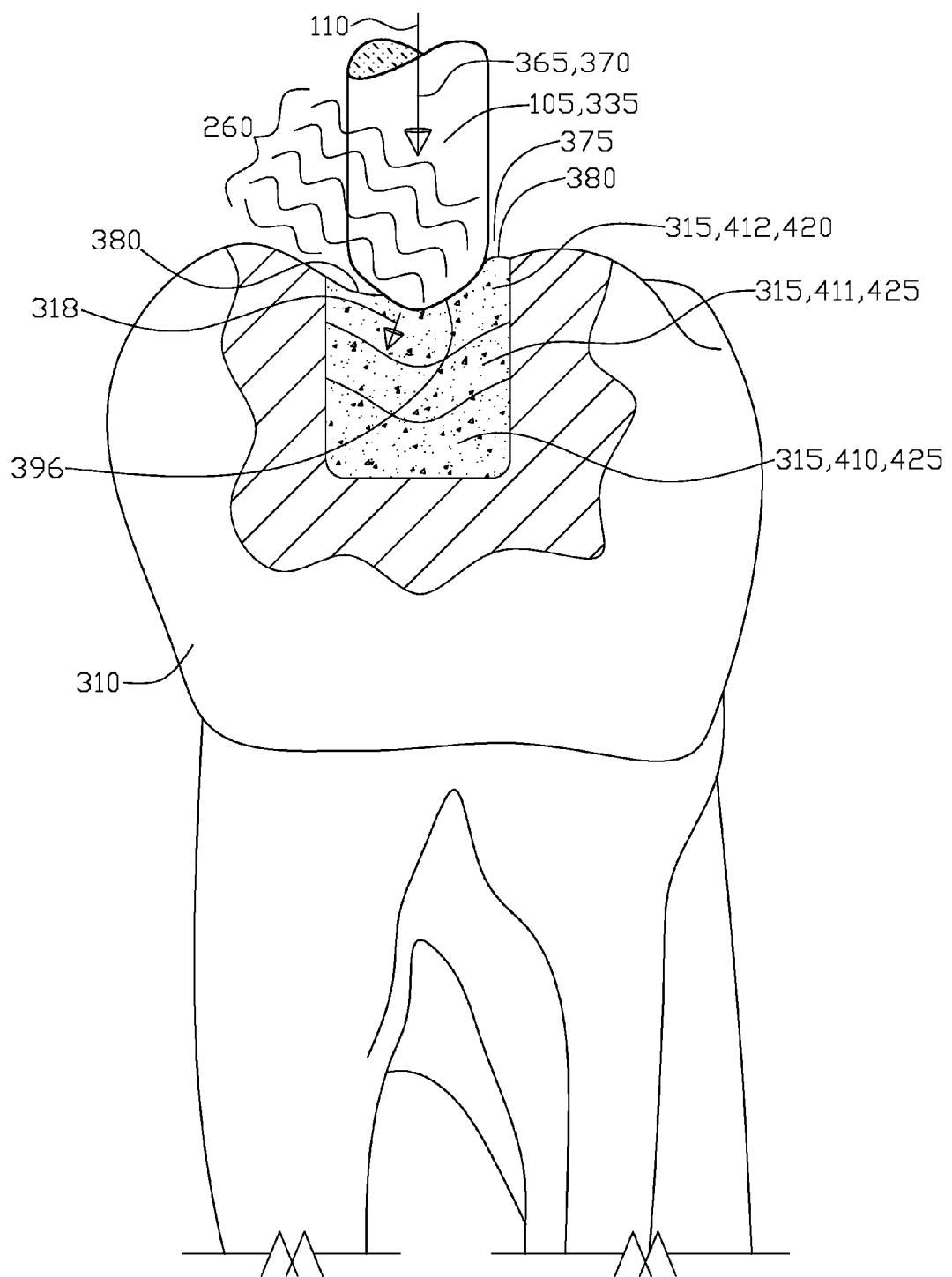
FIG. 47 shows an expanded tooth cross section with the prepared tooth cavity, with the third layer composite filler material in a selected conical shaped configuration with the present invention dental tool transparent tip that is also in a conical shaped configuration that is used to condense and compact the third conical shaped composite filler material layer, wherein the transparent tip maintains a selected amount of pressure upon the composite during the curing process from the light transmission to help compensate for composite shrinkage during the curing process to help prevent undesirable voids from forming as between the composite and the parent tooth material or within the composite material itself, as the tool tip is shown slightly depressed into the composite material with an added goal of minimizing a free area of the composite surface that is neither in contact with the parent tooth material or the tool tip such that the composite free area is uncontrolled during composite curing.

Continuing, FIG. 47 shows an expanded tooth cross section with the prepared tooth cavity 310, being a continuation of FIG. 46 for the subsequent composite 315 layering, as the second conically shaped composite layer 411 is already cured or hardened 425, with the third layer composite filler material in a selected conical shaped configuration 412 with the present invention dental tool transparent tip 105 that is also in a conical shaped configuration 335 that is used to condense and compact the third conical shaped composite filler material layer 412 while in the uncured or pliable state 420.

Wherein the transparent tip 335 maintains a selected amount of pressure 365, 370 as previously described upon the composite 315 during the curing process from the light transmission 260 to help compensate for composite shrinkage 318 during the curing process to help prevent undesirable voids 316 from forming as between the composite 315 and the parent tooth material 310 or within the composite material 315 itself. As the tool tip 335 in FIG. 47 is shown slightly depressed into the composite material 315 with an added goal of minimizing a free area 380 of the composite 315 surface that is neither in contact with the parent tooth material 310 or the tool tip 335 such that the composite free area 380 is uncontrolled during composite curing by being exposed to the atmosphere 375. Note that once the composite free area 380 is at the third layer 412 after curing it will be ground and polished to match the parent tooth material 310 contour on the tooth 310 biting surface opposite of the tooth 310 root structure to complete the tooth 310 cavity filling.

Thus as FIG. 47 shows the multiple conical composite layers 410, 411, and 412, that are interlocked to one another for higher strength for a composite filler 315 buildup to fill the tooth cavity 310 via use on the specially conically shaped transparent tipped tool 335 or any other configuration tool tip can facilitate a composite 315 layer by layer cured hardening in a unique shaped configuration as determined by the prepared cavity 310 shape. Wherein each individual composite 315 layer is cured and hardened while under pressure 365, 370 from the tool tip 335 being embedded into the composite 315 while allowing the curing light transmission 260 to penetrate there-through the tool tip 335 during the curing process to minimize voids and control the configuration of the composite 315 layer as is cures or hardens.

A preferred embodiment of the present invention 50 is illustrated in FIGS. 1-22, 29, 32, 33, and 34. It is to be expressly understood that the descriptive embodiments are provided herein for explanatory purposes only and are not meant to unduly limit the claimed inventions. The exemplary embodiments describe the present invention in terms of dental tools, but it is to be made clear that the claimed invention encompasses other forms of tools where ultraviolet as well as other light sources 250 are used. Also, the claimed invention may be used for tools where anyone or combinations of the high optical transmission rates, the high strength and resistance to fracture or shattering and the ability to shed or prevent adherence of other materials are important.

The present invention provides a tool 50 or 55 that can be used for manipulating and compacting composite fill materials 315 in a cavity 310 of a tooth not only prior to the curing process but also during the actual curing process. The dental tool 50 is used with ultraviolet (light in the range of ten (10) to four hundred (400) nm) as well as visible light (light in the range of three hundred eighty (380) to seven hundred sixty (760) nm) photo curing operations generated from the photo-curing apparatus 250. The tool 50 of the present invention includes at least a portion 107 of the tool 105 that is able to allow ultraviolet rays to pass 260 through without distortion. This allows the tool 50 to be used even while the photo-curing operation is occurring so that the fill material 315 can be evenly compacted to eliminate voids 316 during curing. The fill material 315 may shrink during the photo-curing process, thus causing voids 316 in the fill 315 that can lead to bacteria and other problems. The present invention 50 is able to minimize the occurrence of voids 316 by continuing to compact and manipulate the fill material 315 during the curing process while shrinkage may occur. Previous tools were unable to do this as the ultraviolet rays 260 would be distorted and reflected causing damage to the surrounding tissue.

The translucent tool tip portion 105 not only is able to transmit 260 the ultraviolet rays without distortion, it must also be of sufficient strength to be durable and hard to compact and manipulate the fill material 315 without shattering or causing damage to the patient 300. The tool tip portion 105 of the present invention 50 also has the ability to easily shed or not adhere to the composite fill material 315, due to the tool tip portion 105 having a smooth surface, wherein the composite fill material 315 does not stick to the tool 105 pulling the composite fill material 315 away from the prepared cavity 310 of the tooth. This further minimizes the occurrence of voids 316 in the cavity 310 since the fill material 315 will remain in place once it has been compacted and shaped.

The present invention 50, as set forth in the claims, is directed to dental tools that provide the characteristics, either individually or in combination with one another, of allowing the transmission 260 of visible and ultraviolet wavelengths, durability and strength so that the tool 105 is able to compact the fill material 315 to eliminate voids 316, and to properly shape the fill 315 material, and non-adhesion of the fill material 315 to the tool 105. The claimed invention encompasses not only present materials that meet one or more of these characteristics but materials that may be developed as well that meet one or more of these characteristics.

In a preferred embodiment, discussed in greater detail below, the tool 50 is formed, at least in part, from sapphire for the tip portion 105. It is to be expressly understood that the present invention is not limited to this material, but includes others as well. Sapphire is described herein as one material that meets the scope of the present invention.

Sapphire is an anisotropic, rhombohedral structure of the crystalline form of aluminum oxide ($Al_2O_3$). It occurs naturally but is also able to be synthetically created on an industrial scale. It has a high degree of transmission within the ultraviolet and visible light spectrum while possessing a high degree of strength and toughness as well as chemical resistance and composite fill material does not adhere easily to sapphire. Sapphire is able to transmit wavelengths between two hundred (200) nm to seven hundred sixty (760) nm, and even up to five (5) μm without significant distortion. It also has a compressive strength of 20,000 kg/cm$^2$, with a tensile strength of 7,000 kg/cm$^2$, and a fracture toughness in the range of 2.4-4.5 MPA$\sqrt{}$M (Pascals per square root meters). Sapphire also has the characteristic of being slick, that is, most materials including composite fill materials 315 will not easily stick or adhere to it. It also has a high abrasion resistance so it will not easily scratch which could cause distortion or reflection of wavelengths; see FIG. 31 for a sapphire light transmissibility chart.

This provides a high strength, hard, and durable tool 105 that is capable of allowing ultraviolet rays to transmit 260 through without distortion or reflection. This allows the tool 105 to be used during the photo-curing process so that voids 316 are minimized, the composite fill material 315 can be more precisely shaped-even with composite shrinkage during curing, and the 310 cavity filling process be more efficiently conducted so that the patient 300 spends less time undergoing the process and ending up with a better quality filling that minimizes the loss of structural integrity of the tooth from the filling and provides for an almost visually imperceptible filling. The ability of the tool 105 to be used during the photo-curing process to prevent voids 316 from occurring as the material 315 shrinks, as well as the ability of the tool 105 to shed the fill material 315 so that it remains in place in the cavity 310 increases the efficiency of the process. The sapphire tool is also useful prior to the photo-curing process in placing the fill material 315 in the cavity, compacting the fill material 315 and shaping the fill material 315 since the fill material 315 does not adhere easily to the sapphire tool 105 and the sapphire tool 105 has high strength and durability. The details and features of the tool 105 of the present invention are discussed in greater details below in the description of exemplary embodiments.

A preferred embodiment of the present invention is illustrated in FIGS. 1-22, 29, 32, 33, and 34. An exemplary embodiment of the dental tool 50 is illustrated in FIG. 1 for placing a fill material 315 in tooth cavity 310, manipulating that fill material 315 and compacting the fill material 315 before and during the curing operation as seen in use in FIGS. 5, 11, 13, 15, 17, 27, 28, 30, and 38 through 46. This particular tool 50 is intended to be used for use with a photo-curing application apparatus 250 such as ultraviolet, although other light sources can be used as well. The fill material 315 can be a composite or Ionomer fill material or any other type of fill material that can be cured through photo-polymerization. For descriptive terms only, the fill material 315 is referred to as composite or polymer materials, but it is to be understood that other photo-curable materials are included as well.

The dental tool 50 includes a central gripping member 60 with a first tool end portion 65 and an opposing second tool portion end 70. The central gripping member 60 can be formed of suitable materials, preferably a material that can be easily sterilized and that does not degrade under ultraviolet light. In the preferred embodiment 50, the central gripping member 60 is formed of a high strength plastic with knurled portions for ease of gripping. Alternatively, the gripping member 60 could be formed from stainless steel, aluminum or other suitable materials.

The dental tool 50, of this preferred embodiment, is illustrated with the first tool end portion 65 and the opposing second tool portion end 70. It is to be expressly understood that the tool could also include a single tool 105 end as well. The tool end 65 of this preferred embodiment includes an extended first end 75 with a reduced diameter. This reduced diameter portion 75 includes a first portion 85 that extends outwardly along the longitudinal axis 61 of the gripping member 60 for an extended length then a first extension end portion 95 that angles upwardly for another length. Wherein the longitudinal axis 61 spans therebetween the first end portion 65 and the opposing second end portion 90. The lengths and angle of these two portions are determined by the particulars of the teeth in order to easily access the cavity 310 within a particular tooth while still allowing visibility to the cavity 310. It is to be expressly understood that other lengths, angles and configurations may be used as well within the scope of the invention as claimed.

Rigid dental tool tip portions 105, discussed in greater detail below, are secured to the tool assembly 50. The tool tip portions that are formed as a rigid cantilever beam extension 105 can be formed on the tool assembly 50, permanently affixed to the tool assembly 50, or removably attached to the tool assembly 50. In one preferred embodiment, a collet chuck 185, as seen in FIG. 3, is affixed to the end of the tool end 75. The collet chuck 185 of this preferred embodiment enables the gripping member 60 to be used with a variety of dental tool tips 105 as well as replacement tips 105. Other fastening mechanisms may be used as well in lieu of the collet chuck 185, such as adhesive fasteners 210, as shown in FIG. 4, cam locking mechanisms, or any other fastening mechanism. It is also to be expressly understood that the tool assembly 50 or 55 may use permanently affixed dental tool tips 105 as well instead of a fastening mechanism. Collet chucks 185 are well known for securing tools and typically, as shown in FIG. 3, include an inner sleeve 190 that is radially resilient so it will compress over the dental tool tip 105 as pressure is applied radially against it. An outer sleeve 195 having a radially tapered inner diameter extending axially down its length is slidable relative to the inner sleeve 190. As the inner sleeve 190 is moved upward inside the outer sleeve 195, the radial taper of the inner diameter of the outer sleeve 195 compresses the inner sleeve 190 over the dental tool tip 105. A detent 200 locks the sleeves 190 and 195 in place. The reverse operation will release the dental tool tip 105 from the collet chuck 185.

The opposing end 70 of the gripping member 60 similarly includes reduced diameter end portions 80, 90 that extend from the gripping member 60. These end portions may be identical to the end portions on the opposing end of the gripping member 60 or may be at differing lengths and angles to provide a different function. A collet chuck 185 may be affixed to the first tool end portion 65 and the opposing second tool end portion 70, or the tool tips 105 may be permanently affixed, as shown in FIG. 4. For the permanent affixing, FIG. 4 shows the tip 105 cylindrical portion 130 inserted into and disposed within the second portions 95 and 100 into receiving bore or receiving void 101 forming an interface as shown by adhesive 210 in FIG. 4, leaving an exposed portion 107 of the tip 105, also shown in FIG. 4. Also, positionally the longitudinal axis 61 and the lengthwise axis 110 form an obtuse angle 345 that is adjacent to the tip 105, as shown in FIG. 1. Wherein a preferred radial clearance 205 of about ten-thousandths (0.010) of an inch and a depth 102 to diameter 103 ratio of at least one is preferred of the receiving bore 101 as determined from experimental testing. Noting that the tip 105 typical diameter 106 is in the range of about one (1) to four (4) millimeters (mm), the preferred adhesive 210 is LOCTITE #M31CL medical grade epoxy with ISO certification 10993 or a suitable equivalent. As a further enhancement to the adhesive 210 shown in FIG. 4, the cantilever beam extension 105 that is positioned within the slip fit 205 clearance has a surface area increase via abrading to further increase an adhesive 210 strength of the epoxy. The preferred surface area increase surface treatment 215 is preferably Zirconia dust is applied to the diameter 106 prior to the adding of the adhesive 210 in the clearance or slip fit area 205. The slip fit or clearance 205 as a percentage of the tip portion 105 is determined as follows; with the preferred clearance of 0.010 inches and a typical tip portion 105 diameter 106 being typically 2 millimeters (mm) which equals 0.079 inches, thus 0.010 inches divided by 0.078 inches equals about twelve (12) percent, see FIG. 4.

The combination of the gripping member 60 and the dental tool tips 105 of the present invention are uniquely designed tools that are able to accept a multitude of omnidirectional force 365 loadings related to the lengthwise axis 110, see FIG. 4, to provide a combination of high strength for performing the operations of manually filling, manipulating, placing, forming, condensing, shaping, and compacting the composite fill material 315 being preferably 3M Filltek or equivalent within or outside of the prepared cavity 310 not only prior to the photo-curing operation but during the photo-curing operation as well. Thus, the present invention is not merely a lens for ultraviolet light to pass, but is actually a true dental tool 50 or 55 for working in and on the tooth 310 being embedded into the composite filler material 315 before 420 and after 425 curing.

It is critical that the material 315 be properly compacted to eliminate voids 316 and air bubbles 316 within the fill material 315 to prevent problems from occurring later, see FIGS. 11 and 35 through 47. The dental tool tips 105 of the preferred embodiment 50 are formed from a translucent material that will transmit ultraviolet wavelengths without reflecting or redirecting the light rays 260. The tip 105 material must also be sufficiently durable and hard to enable the compacting and manipulation of the fill material 315. In this preferred embodiment 50, the dental tool tips 105 are formed from sapphire. The sapphire will enable the use of the dental tool 50 during the photo-curing operation without distorting or reflecting the ultraviolet or other light transmission 260 wavelengths. Further, the sapphire tool tip 105 is relatively hard and durable so that there is no danger of shattering under use especially from the omnidirectional forces 365 loading as previously described and will sufficiently compact the fill material 315 when force is applied to eliminate any voids 316 or air bubbles 316 both before 420 and after 425 curing. The sapphire tool tip 105 is also useful prior to the photo-curing process as the composite fill material 315 will not easily adhere to it due to its smooth surface and the composite fill material 315 curing and hardening going from 420 to 425 while in contact with the tool tip 105 both work to prevent the composite filler material 315 from sticking to the tool tip 105. This minimizes voids 316 forming, due to lifting or ripping of the fill material 315 from the cavity 310 due to adhesion of the filler material 315 to the tool tip 105, see FIG. 37.

The sapphire tool tip 105 can be formed into a cylindrical rod 130, see FIGS. 1, 2, 4, and 8, so that it can be engaged into the collet chuck 185, as shown in FIG. 3, or affixed with adhesive 210 as shown in FIG. 4. The tip portion 105 can be further shaped into a particular shape, as discussed in greater detail below, see FIGS. 5 through 22, and 29, 30, 32, 33, and 38 through 46. Alternatively, the tool tip 105 can include an intermediate portion formed from a translucent plastic material that engages in the collet chuck 185 while a sapphire tool tip 105 is affixed to the intermediate portion.

The outer surface finish of the tip 105 is related to light wave length transmission, see FIG. 31, wherein there can be further limits on surface finish imperfections or as termed undulations, see FIG. 4 for what is termed "scratch" and "dig" limits, which are optical material surface polish quality indexes, wherein scratch relates to a width and length of the imperfection and their cumulative size and number, wherein on the present invention the scratch limit is preferably about eighty (80), wherein a dig is related to a diameter of the imperfection and their cumulative size and number, wherein on the present invention the dig limit is preferably about fifty (50). Thus, for the tip 105 or cantilever beam extension 105 has a surface with scratch undulations that preferably do not exceed about three-thousandths (0.003) of an inch in width 350 and no more than about one-fourth (¼) in length 355 of an exposed cantilever beam extension 105 dimension that is perpendicular (such as the diameter 106 in FIG. 4) to the lengthwise axis 110, in total, to operationally preserve the wavelength transmission, as shown in FIGS. 4 and 31. Continuing, for the tip 105 or cantilever beam extension 105 has a surface with dig undulations that preferably do not exceed about twenty-thousandths (0.020) of an inch in diameter 360, wherein a total sum of undulation diameters 360 shall not exceed more than about two times a maximum single diameter 360 undulation, to operationally preserve the wavelength transmission, also as shown in FIGS. 4 and 31, wherein a scratch and dig limit that allowed greater size surface undulations would impair wavelength transmission to be undesirably low.

The sapphire tool tip 105 can be formed into a variety of shapes being about its longitudinal axis 110 and configurations depending on the function to be accomplished and the tooth that is being filled. For example, as shown in FIGS. 8 through 30, 32 through 34, and 38 through 46, different tool tips are illustrated. Particular shapes may be used for different teeth, such as differing shapes for the bicuspids, molars, etc. as well as the locations of the teeth and location of the cavity to be filled. The dental tool tip 105 previously discussed variety of shapes can include specific geometry types that can include partial spheres, wedges, frustroconical shapes, arcuate segments, rectangular parallelepipeds, hoes, and cylinders, as particularly shown in FIGS. 1, 2, 4, 5-12, 14, 16-22, 29, 32, 33, and 38 through 47. It is to be expressly understood that other shapes and configurations may be included within the scope of the claimed inventions.

Method of Manufacture

Referring to FIGS. 1 through 4, 6 through 10, 12 through 22, and 29 through 34, a method for manufacturing the dental tool 50 is disclosed that is for photo-curing a dental tooth cavity filling 310 using a photo-curing composite 315 as a cavity filling material, the dental tool 50 manufacture comprising the steps of; firstly, providing a gripping member 60 having the longitudinal axis 61. The gripping member 60 including a first end portion 65 and the opposing second end portion 70 with the longitudinal axis 61 spanning therebetween, with the first or second extension end portions 95 and 100 respectively having the receiving void 101 disposed therein that is preferably constructed of stainless steel or another suitable material, see in particular FIGS. 1 through 4.

A second step of providing a rigid smooth surface transparent light transmitting tool tip extension in the form of a cantilever beam extension 105 that is preferably constructed of sapphire, wherein the cantilever beam extension 105 has a lengthwise axis 110, wherein the tool tip 105 has a tensile strength of between two hundred seventy five MPa and four hundred MPa. Looking at particular at FIG. 4, a portion of the tool tip 105 has a slip fit relationship 205 with the receiving void 101 forming a radial clearance 205 between the receiving void 101 for about a length 102 along lengthwise axis 110 and the tool tip 105 portion when the tool tip 105 portion is disposed within the receiving void 101.

Continuing to primarily reference FIG. 4, a third step of abrading the portion of tool tip 105 that resides within the slip fit 205 that is adjacent to the radial clearance 205 as an area increasing surface treatment 215 to the tool tip 105 to increase a surface area of the tool tip 105 adjacent to the radial clearance 205, wherein the surface area increase is operational to further increase an affixed attachment strength of the tool tip 105 to the receiving void 101. Also referring to FIG. 4, a fourth step of applying a medical grade epoxy 210 to the abraded portion 215 of tool tip 105 and again referring to FIG. 4, a fifth step of bonding the sapphire tool tip 105 to the stainless steel receiving void 101 by inserting the abraded 215 and epoxy coated 210 tool tip 105 into the receiving void 101 allowing the epoxy 210 to cure and harden. Thus, resulting in a portion of the cantilever beam extension 105 being disposed completely within and affixed to the receiving void 101 forming an interface 210, leaving an exposed portion 107 of the cantilever beam extension 105 to function as the transparent light transmitting tool tip 105. Wherein operationally allowing for omnidirectional forces 365, see FIGS. 4 and 38 through 46, creating loading on the exposed portion 107 of the tool tip 105 from a manual grasping 60 and 320 as shown in FIG. 28, of the gripping member 60 that is reacting at the interface 210 to the forces 365 of manually placing, forming, condensing, and shaping the composite filler material 315 within the prepared tooth cavity 310.

Further, in looking at FIG. 4, the fourth step of abrading 215 is preferably accomplished by applying zirconium to the tool tip 105 via physical vapor deposition. Physical vapor deposition is used primarily with vacuum deposition processes such as evaporation and sputtering. Physical Vapor Deposition or (PVD) is a process by which a thin film of material, being zirconium in the present case, is deposited on a substrate being the abraded area 215 in this case, see FIG. 4, according to the following sequence of steps: 1) the material to be deposited is converted into vapor by physical means; 2) the vapor is transported across a region of low pressure from its source to the substrate; and 3) the vapor undergoes condensation on the substrate to form the thin film. A common method of accomplishing PVD of thin films is by sputtering.

Sputtering is a mechanism by which atoms are dislodged from the surface of a material as a result of collision with high-energy particles. Thus, PVD by sputtering is a term used to refer to a physical vapor deposition (PVD) technique wherein atoms or molecules are ejected from a target material by high-energy particle bombardment so that the ejected atoms or molecules can condense on a substrate as a thin film. Sputtering has become one of the most widely used techniques for depositing various metallic films.

Sputtering as a deposition technique may be described as a sequence of these steps: 1) ions are generated and directed at a target material; 2) the ions sputter atoms from the target; 3) the sputtered atoms get transported to the substrate through a region of reduced pressure; and 4) the sputtered atoms condense on the substrate, forming a thin film, which in the present case acts to increase the surface area at 215, see FIG. 4, to result in an improved bond as between the surface area 215 and the medical grade epoxy 210 adhesive, ultimately resulting in a stronger affixed bond as between the receiving void 101 (gripping member 60) and the tool tip 105 that experiences omnidirectional forces 365 from the dentist or practitioner 320 holding the gripping member 60 and compressing 365 the composite 315 in the prepared tooth 310 during composite 315 curing, see FIGS. 38 through 47.

Method of Use

The tooth is prepared for filling by removing any decay and shaping the cavity 310 to receive the fill material 315. The fill material 315 is applied in thin (approximately one millimeter (mm in thickness) layers 317 by depositing the material 315 in the cavity 310 and then manipulating it as shown in FIGS. 5, 11, 13, 15, 17, 27, 28, 30, and 43 through 47, with the dental tool 50 or 55. A light source 250 is then used to cure the fill material 315. The compaction and manipulation of the fill material 315 in the cavity 310 continues with the use of the dental tool 50 during the curing process, with the photo-curing light 250 as a separate item, see in particular FIG. 28. The ultraviolet rays are transmitted 260 through the tool tip 105 with little or no distortion or reflection so no damage occurs to the surrounding tissue. The continued compaction and manipulation of the fill 315 during the curing process minimizes any voids 316 from occurring due to the shrinking from the curing of the material 315. This provides a much more efficient and reliable process than attempting to later fill voids 316 that have occurred.

The efficiency of the cavity filling process is increased by the use of the tool 50 or 55 and its unique combination of optical transmission 260 so that it can be used during the photo-curing process, the hardness of the tool tip 105 to compact the material 315 to prevent voids 316 from occurring and the ability to shed (not stick to) the fill material 315 so that the fill material 315 remains in place in the cavity 310. The ability of the tool tip 105 to be used during the photo-curing process allows the material 315 to be compacted and shaped as it shrinks to prevent voids 316 from occurring, increases the efficiency over previous tools 390 that could only be used before or independent of the photo-curing process. Voids 316 would occur with these tools as the material 315 shrinks during curing, see FIGS. 36 and 37. These voids 316 would then have to be filled, thus increasing the time of the filling process. The hardness of the tool tip 105 also minimizes voids 316 as the material 315 is thoroughly compacted by the tool tip 105 before and during the curing process. The ability to shed the fill material 315 also decreases the time of the filling process as the material 315 does not easily cling to the tool tip 105 once it has been placed. This allows the Dentist or practitioner 320 to reduce or eliminate the need for "wetting" the tip 105 to help prevent sticking of the composite fill material 315 to the tip 105, as the composite fill material 315 is curing while under manual compacting pressure from the Dentist or practitioner 320 while the light 260 is being applied, thus reducing the time it takes for multiple "wetting" processes, see FIGS. 28 and 37. Thus, the tool tip 105 of the present invention 55 or 55 increases the efficiency of the tooth cavity 310 filling process. Also the wetting of the tool tip 105 introduces wetting substance contamination into the tooth 310 and composite 315 interface or composite 315 layer to composite 315 layer interface, potentially interfering with good adhesion or causing voids 316.

Looking in particular at FIGS. 23 through 27, as the alternative embodiment 55 is shown for the combined dental tool assembly 50 and the photo-curing light apparatus 250 further making this process of composite 315 photo-curing quicker, easier, and more efficient. As it is important to have the photo-curing light transmission 260 as close as possible to the composite material 315 and to minimize the "crowding" in the patient's 300 mouth 305 by having the light transmission 260 from light generating apparatus 250 travel therethrough the tool 55 itself or more specifically through the grip portion 60 allowing a one handed operation for the dentist 320 and more accurate photo-curing positioning. This results in minimizing any chance of voids 316 or porosity 316 in the cured composite 315 for a high quality filling with more structural integrity in the filled tooth, and in addition less time for the patient 300 to have tools in their mouth 305. Note that it is also preferable to have the light apparatus 250 be removably engagable 251 from the tool assembly 55 for sanitizing reasons, having the removable engagement 251 either near the tip 105, as shown in FIGS. 23 and 24, or near the grip 60, proximal end portion 56 as shown in FIGS. 25 and 26.

Thus in referring to FIGS. 23 through 28 and 40 through 47, for additional detail, the method of manually using a dental tool 50 by a dental practitioner 320 for photo-curing a dental tooth cavity 310 is disclosed having a dental tooth filling 315 using a photo-curing composite 315 as a dental tooth cavity filling material 315, the dental tool 50 use comprising the steps of firstly providing a dental tool 50 that includes a manual gripping member 60 having a longitudinal axis 61. The gripping member 60 including a first end portion 65 and the opposing second end portion 70 with the longitudinal axis 61 spanning therebetween. Looking at particular at FIG. 4, the first end portion 70 having a receiving void 101 disposed therein, in addition a rigid smooth surface transparent light transmitting tool tip extension 105 in the form of a cantilever beam extension, having a lengthwise axis 110, a portion of the cantilever beam extension 105 is disposed completely within 102 and affixed 210 to the receiving void 101 forming an interface 210, leaving an exposed portion 107 of the cantilever beam extension 105 to function as the transparent light 260 transmitting tool tip 105.

Referencing FIGS. 1 through 4, the tool tip 105 has a tensile strength of between two hundred seventy five MPa and four hundred MPa, wherein positionally the longitudinal axis 61 and the lengthwise axis 110 form an obtuse angle 345 that is adjacent to the exposed portion 107 of the cantilever beam extension 105. Thus, operationally allowing for omnidirectional forces 365 creating loading on the exposed cantilever beam extension portion 107, the interface 210, and the gripping member 60 in relation to the lengthwise axis 110 from the exposed 107 cantilever beam extension 105 reacting to the forces 365 of manually placing, forming, condensing, and shaping the composite filler material 315 in the dental cavity 310, see FIGS. 1 through 7, 11, 13, 15, 17, 27, 28, 30, and 38 through 47.

Next, a second step of providing a dental tooth cavity preparation tool as is well known in the art, such as drills, files, and various other dental tooth cavity preparation tools that result in a prepared dental tooth cavity 310, as best shown in FIGS. 35 through 47. Further, a third step of providing a dental tooth cavity composite filling photo curing light apparatus 250, again as is known in the art, as best shown in FIGS. 23 through 28. Yet, further a fourth step of preparing the dental tooth by the dental practitioner 320 for cavity filling 310 by removing any decay and selectively shaping the cavity 310 within the dental tooth to receive the composite filler material via the cavity preparation tool as is well known in the art, see in particular FIGS. 35 through 47.

Continuing, a fifth step of applying the composite filler material 315 that is in contact with the dental tool tip 105 extension exposed portion 107 via the dental practitioner 320 manually grasping the manual gripping member 60, see FIG. 28, wherein the composite filler material 315 is in a pliable non-hardened and non-cured state 420 and the composite filler material 315 is applied in a thin layer of about one millimeter in thickness by the dental practitioner 320 manually depositing the pliable 420 composite filler material 315 into the prepared cavity 310 in a selected configuration, see FIGS. 5, 11, 13, 15, 17, 30, and 38 through 47.

Further, a sixth step of condensing the pliable composite filler material 315 within the tooth cavity 310 via the dental practitioner 320 applying a selected force 365, 370 at the manual gripping member 60 resulting in a force 365, 370 at the dental tool tip extension 105 exposed portion 107 that is in pressure contact with the pliable composite filler material 315 to selectively shape, form, and tightly compact the pliable 420 composite filler material 315 as against the tooth cavity 310 and to substantially remove voids 316 within the pliable composite filler material 315, as best shown in FIGS. 36 through 47. However, in looking in particular at FIG. 39, the selected force 365, 370 not being overly excessive such as to cause uncontrolled flowing 385 of the composite filler material 315 in a free area 380 defined as that area 380 is not in contact with the prepared tooth cavity 310 or the dental tool tip extension 105 exposed portion 107. Note that this uncontrolled flowing 385, shown in FIG. 39 of the composite filler material 315, if left as is or it is inadvertently cured or hardened 425 with the flowing 385 will be an unsuitable mating surface for a subsequent composite filler material 315 layer and thus the flowing 385 will have to be manually removed by grinding by the dental practitioner 320 causing unnecessary time and discomfort for the dental patient.

Next, in looking at FIGS. 5, 11, 13, 15, 17, 28, 30, and 36 through 47, a seventh step of the dental practitioner 320 continuing to apply the selected force 365, 370 at the manual gripping member 60 that communicates to the dental tool tip extension 105 exposed portion 107 that is in pressure contact with the pliable 420 composite filler material 315 while simultaneously utilizing the photo curing light apparatus 250 to direct a beam of light 260 toward the pliable 420 composite filler material 315. Wherein a portion of the beam of light 260 is transmitted therethrough the dental tool tip 105 extension exposed portion 107 to enable the beam of light 260 to contact the pliable 420 composite filler material 315 to change the composite filler material 315 from the non-hardened state 420 to the hardened state 425 for a selected amount of time light beam 260 exposure, thus in effect curing 425 the composite filler material 315. However, all the while keeping the dental tool tip 105 extension exposed portion 107 in contact with and applying pressure 365, 370 upon the composite filler material 315 in place throughout the curing process 425 to minimize voids 316 forming from shrinkage 405 within the hardened 425 composite filler material 315 via compensating for curing 425 composite filler material 315 shrinkage 405 by applying pressure 365, 370, see FIGS. 38 and 40 through 47.

Further the pressure 365, 370 must be moderated—i.e. not be excessive to minimize the uncontrolled flowing 385 from hardening 425 of the composite filler material 315, see FIG. 39, and to minimize sticking of the composite filler material 315 to the dental tool tip 105 extension exposed portion 107 interface 395 to reduce pull back 400 of the composite filler material 315 away from the tooth cavity 310, see FIG. 37, thus reducing hardened 425 composite filler material 315 voids 316. Thus, use of the dental tool tip 105 extension exposed portion 107, with the pressure force 365, 370 being in contact with the composite filler material 315 during the hardening process going from 420 to 425 works to maintain a desired configuration of the hardened 425 composite filler material 315 layer when the dental tool 50 is removed by the dental practitioner 320 from a patient's mouth, see FIGS. 38 and 40 through 47.

To further accommodate the layering technique for dental tooth cavity 310 fillings using the composite filler material 315, as best shown in FIGS. 40 through 47, the previously described fifth, sixth, and seventh steps are sequentially repeated for a selected number of subsequent composite filler material 315 layers by the dental practitioner 320 for various selected configurations, see in particular FIGS. 43 and 47 wherein the end result on the final layering technique is shown.

Continuing, in referencing FIGS. 28, 38, and 40 through 47, on the method of manually using the dental tool 50, wherein the sixth step of condensing to create the selected force 365, 370 by the dental practitioner 320 is preferably in the range of about one-half (½) pound of force for the selected force 365, 370 to operationally have just enough force 365, 370 at the dental tool tip 105 extension exposed portion 107 that is in contact with the pliable 420 composite filler material 315 that is being manipulated such that the force 365, 370 is just compensatory to perceived shrinkage 318 to the composite filler material 315 during the curing process 420 to 425.

Thus, being operational to further minimize the voids 316 forming within the hardened 425 composite filler material 315, see FIG. 36 for the effect of shrinkage 318 in the curing composite filler material 315 without compensatory force 365, 370. Also, to minimize the sticking of the composite filler material 315 to the tool tip 105 extension 107 interface 395 to reduce pull back 400 of the composite filler material 315 away from the tooth cavity 310, see FIG. 37, being without the need of an anti-stick wetting agent that is positioned at the interface 395. The reduction in sticking at the interface 395 is due to a smooth surface finish on the exposed portion 107 of the dental tool tip 105 as previously described and holding the dental tool tip 105 exposed portion 107 in place against the composite filler material 315 during curing 420 to 425, as the hardened composite filler material 315 will not stick at the interface 395.

With the wetting agent being to prevent the interface 395 sticking, the wetting agent being especially required with a conventional dental tool made of stainless steel 390, however, being undesirable as keeping the prepared tooth cavity 310 dry enhances adhesion of the composite filler material 315 to the prepared tooth cavity 310, thus the wetting agent can interfere with the adhesion of the composite filler material 315 to the prepared tooth cavity 310. Further, the dental tool tip 105 exposed portion 107 dental practitioner 320 selected force 365, 370 helps to maintain a desired configuration shape of the composite filler material 315 layer during hardening 420 to 425, but not the application of excessive force 356, 370 which would result in the uncontrolled flowing 385 of the composite filler material 315 in the free area 380 just outside of the dental tool tip 105 extension exposed portion 107, see FIG. 39.

Further, in referencing FIGS. 28, 38, and 40 through 47, the method of manually using a dental tool 50 wherein the seventh step of continuing to apply the selected force 365, 370 by the dental practitioner 320 is in the preferred range of about one-half (½) pound of force for the selected force 365, 370. Thus for the selected force 365, 370 to operationally have just enough force 365, 370 at the dental tool tip 105 extension exposed portion 107 that is in contact with the pliable 420 composite filler material 315 that is being manipulated such that the force 365, 370 is just compensatory to actual shrinkage 318 to the composite filler material 315 during the curing process 420 to 425 as to further minimize the voids 316 forming within the hardened 425 composite filler material 315, see FIG. 36 for the effect of shrinkage 318 in the curing composite filler material 315 without compensatory force 365, 370.

In addition, referencing FIGS. 4 through 22, 29, 30, 32, 33, 38, and 40 through 47, for the method of manually using the dental tool 50, wherein the first step of providing of the dental tool 50 further includes the dental practitioner 320 selecting a specific geometry type for the dental tool tip extension 105 exposed portion 107 that is in contact with the pliable 420 composite filler material 315 that is being manipulated such that the specific geometry type forms the specific geometry type configuration shape of the composite filler material 315 layer while in the uncured 420 pliable state and molds the composite filler material 315 into the specific geometry type configuration shape permanently as the composite filler material 315 moves into the cured 425 and hardened state, see in particular FIGS. 40 through 47.

Further, looking at FIG. 39, for the method of manually using a dental tool 50 wherein the first step of providing of the dental tool 50 further includes the dental practitioner 320 selecting a specific size for the dental tool tip 105 extension exposed portion 107 that is in contact with the pliable 420 composite filler material 315 that is being manipulated such that the specific size minimizes the free area 380 of the composite filler material 315 to minimize the uncontrolled flowing 385 of the composite filler material 315. Wherein the uncontrolled flowing 385 could become permanent in the form of hardened 425 composite filler material 315 requiring removal of the hardened 425 uncontrolled flowed 385 composite filler material 315. The flowed 385 material 315 removal would have to be removed either prior to applying the subsequent composite filler material 315 layer or for the finishing composite filler material 315 layer to match the tooth contour, in any case the removal would be time consuming for the dental practitioner 320 and irritating to the patient. As an example, the specific size could be related to the size of the diameter 106 of the exposed 107 dental tool tip 105, see FIG. 4, to again minimize the free area 380 to minimize uncontrolled flowing 385 as shown in FIG. 39.

Referring in particular to FIGS. 40 through 47, an interface 396 is shown as being between the transparent tool tip 105 and the composite filler material 315 that allows the dental practitioner 320, as shown in FIGS. 27 and 28, to visually observe a condition of the composite filler material 315 directly underneath the transparent tool tip 105 that is in contact with the composite filler material 315, thus enhancing the dental practitioner's 320 ability to confirm either a condition of the composite filler material 315 or a potential presence of undesirable voids 316 within the composite filler material 315, with an example of the void 316 shown in FIG. 36. Thus, for the method of manually using the dental tool 50 or 55, can further comprise an optional step subsequent to the fifth step of applying the composite filler material 315, of the dental practitioner 320 visually observing the interface 396 as between the transparent light transmitting tool tip 105 and the photo-curing composite 315 to confirm the selected configuration of the photo-curing composite 315. In addition, for the method of manually using a dental tool 50 or 55, can also further comprise an optional step subsequent to the sixth step of condensing the pliable composite filler material 315, of the dental practitioner 320 visually observing the interface 396 as between the transparent light transmitting tool tip 105 and the photo-curing composite 315 to confirm the substantial removal of voids 316 within the pliable composite filler material 315.

CONCLUSION

Accordingly, the present invention of a dental tool assembly 50 or 55 has been described with some degree of particularity directed to the embodiment(s) of the present invention. It should be appreciated, though; that the present invention is defined by the following claims construed in light of the prior art so modifications or changes may be made to the exemplary embodiment(s) of the present invention without departing from the inventive concepts contained therein.

The invention claimed is:

1. A method of manually using a dental tool by a dental practitioner for photo-curing a dental tooth cavity having a dental tooth filling using a photo-curing composite as a dental tooth cavity filling material, said dental tool use comprising the steps of:
    (a) providing a dental tool that includes a manual gripping member having a longitudinal axis, said gripping member including a first end portion and an opposing second end portion with said longitudinal axis spanning therebetween, said first end portion having a receiving void disposed therein, in addition a rigid smooth surface omnidirectionally transparent light transmitting tool tip extension in the form of a rigid cantilever beam extension, having a lengthwise axis, a portion of said cantilever beam extension is disposed completely within and rigidly permanently affixed to said receiving void forming a permanently affixed interface, leaving an exposed portion of said cantilever beam extension that is permanently affixedly integral with said gripping member, said rigid exposed portion of said cantilever beam extension to function as said transparent light transmitting tool tip, wherein said tool tip has a tensile strength of between two hundred seventy five MPa and four hundred MPa, wherein positionally said longitudinal axis and said lengthwise axis form an obtuse angle that is adjacent to said exposed portion of said cantilever beam extension, operationally allowing for omnidirectional forces creating loading on said exposed cantilever beam extension portion, said interface, and said gripping member in relation to said lengthwise axis from said exposed cantilever beam extension reacting to the forces of manually placing, forming, condensing, and shaping the composite filler material within a prepared tooth cavity;
    (b) providing a dental tooth cavity preparation tool;
    (c) providing a dental tooth cavity composite filling photo curing light apparatus;
    (d) preparing the dental tooth by the dental practitioner for cavity filling by removing any decay and selectively shaping the cavity within the dental tooth to receive the composite filler material via said cavity preparation tool;
    (e) applying the composite filler material that is in contact with said dental tool tip extension exposed portion via the dental practitioner manually grasping said manual gripping member, wherein the composite filler material is in a pliable non-hardened and non-cured state and the composite filler material is applied in a thin layer of about one millimeter in thickness by the dental practitioner manually depositing the pliable composite filler material into the prepared cavity in a selected configuration;
    (f) condensing the pliable composite filler material within the tooth cavity via the dental practitioner applying a selected force at said manual gripping member resulting in a force at said dental tool tip extension exposed portion that is in pressure contact with the pliable composite filler material to selectively shape, form, and tightly compact the pliable composite filler material as against the tooth cavity and to substantially remove voids within the pliable composite filler material with said selected force, wherein said force not being so excessive such as to cause uncontrolled flowing of the composite filler material in a free area that is not in contact with the prepared tooth cavity or said dental tool tip extension exposed portion for helping in prevention of voids in the composite filler material in the tooth cavity; and
    (g) continuing to apply said selected force by the dental practitioner at said manual gripping member that affixedly communicates to said dental tool tip extension exposed portion that is in pressure contact with the pliable composite filler material while simultaneously utilizing the photo curing light apparatus to direct a beam of light toward the pliable composite filler material wherein a portion of the beam of light is transmitted therethrough the dental tool tip extension exposed portion to enable the beam of light to contact the pliable composite filler material to change the composite filler material from the non-hardened state to the hardened state for a selected amount of time for light beam exposure, thus in effect curing and hardening the composite filler material, while simultaneously keeping said dental tool tip extension exposed portion in contact with and applying pressure upon the composite filler material in place throughout the curing process to minimize voids forming from shrinkage within the hardened composite filler material via compensating for curing composite filler material shrinkage by said applying pressure, to minimize said uncontrolled flowing from hardening, and to minimize sticking of the composite filler material to the dental tool tip extension exposed portion to reduce pull back of the composite filler material away from the tooth cavity thus reducing hardened composite filler material voids, and to maintain a desired configuration of the hardened composite filler material layer when said dental tool is removed by the dental practitioner from a patient's mouth, thereby resulting in the hardened and cured composite having minimal voids and the composite filler material in a desired fixed, hardened, and cured composite layer configuration within the tooth.

2. A method of manually using a dental tool according to claim 1 wherein said steps (e), (f), and (g) are sequentially repeated for a selected number of subsequent composite filler material layers by the dental practitioner.

3. A method of manually using a dental tool according to claim 1 wherein said step of condensing to create said selected force by the dental practitioner is in the range of about one-half (½) pound of force applied at said gripping member for said selected force to operationally have just enough force at said dental tool tip extension exposed portion that is in contact with the pliable composite filler material that is being manipulated such that said force is just compensatory to perceived shrinkage of the composite filler material during the curing process to further minimize the voids forming within the hardened composite filler material, to minimize the sticking of the composite filler material to the tool tip to reduce pull back of the composite filler material away from the tooth cavity potentially causing the voids without the need of an anti-stick wetting agent, which can interfere with the composite with the composite and tooth adhesion plus potentially cause voids in the composite and to maintain a desired configuration shape of the composite filler material layer, but not the application of excessive force which would result in the uncontrolled flowing of the composite filler material in the free area just outside of said dental tool tip extension exposed portion for helping in prevention of voids in the composite filler material in the tooth cavity.

4. A method of manually using a dental tool according to claim 1 wherein said step of continuing to apply said selected force by the dental practitioner is in the range of about one-half (½) pound of force applied at said gripping member for said selected force to operationally have just enough force at said dental tool tip extension exposed portion that is in contact with the pliable composite filler material that is being manipulated such that said force is just compensatory to actual shrinkage of the composite filler material during the curing process to further minimize the voids forming within the hardened composite filler material, to minimize the sticking of the composite filler material to the tool tip to reduce pull back of the composite filler material away from the tooth cavity without the need of an anti-stick wetting agent, which can interfere with the composite with the composite and tooth adhesion plus potentially cause voids in the composite and to maintain a desired configuration shape of the composite filler material layer into the cured and hardened state, but not the application of excessive force which would result in the uncontrolled flowing of the composite filler material in the free area just outside of said dental tool tip extension exposed portion prior to the completion of the curing and hardening of the composite filer material for helping in prevention of voids in the composite filler material in the tooth cavity.

5. A method of manually using a dental tool according to claim 1 wherein said step of providing of a dental tool further includes the dental practitioner selecting a specific geometry type for said dental tool tip extension exposed portion that is in contact with the pliable composite filler material that is being manipulated such that said specific geometry type forms said specific geometry type configuration shape of the composite filler material layer while in the uncured pliable state and molds the composite filler material into the specific geometry type configuration shape permanently as the composite filler material moves into the cured and hardened state.

6. A method of manually using a dental tool according to claim 1 wherein said step of providing of a dental tool further includes the dental practitioner selecting a specific size for said dental tool tip extension exposed portion that is in contact with the pliable composite filler material that is being manipulated such that said specific size minimizes the free area of the composite filler material to minimize the uncontrolled flowing of the composite filler material wherein the uncontrolled flowing could become permanent in the form of hardened composite filler material requiring removal of the hardened uncontrolled flowed composite filler material for helping in prevention of voids in the composite filler material in the tooth cavity.

7. A method of manually using a dental tool according to claim 1 further comprising a step subsequent to said step (e) of the dental practitioner visually observing an interface as between said transparent light transmitting tool tip and the photo-curing composite to confirm said selected configuration of the photo-curing composite.

8. A method of manually using a dental tool according to claim 1 further comprising a step subsequent to said step (f) of the dental practitioner visually observing an interface as between said transparent light transmitting tool tip and the photo-curing composite to confirm said substantial removal of voids within the pliable composite filler material.

* * * * *